US012724030B2

(12) United States Patent
Finn et al.

(10) Patent No.: US 12,724,030 B2
(45) Date of Patent: Sep. 1, 2026

(54) COMPOSITIONS AND METHODS FOR THE DETECTION AND TREATMENT OF SARS-CoV-2 VIRUS INFECTION

(71) Applicants: GEORGIA TECH RESEARCH CORPORATION, Atlanta, GA (US); THE USA, AS REPRESENTED BY THE SECRETARY, DEPT. OF HEALTH AND HUMAN SERVICES, Bethesda, MD (US)

(72) Inventors: M.G. Finn, Atlanta, GA (US); Asheley Chapman, Atlanta, GA (US); Jason Goldstein, Atlanta, GA (US); Liangjun Zhao, Atlanta, GA (US); Dennis Anthony Bagarozzi, Jr., Atlanta, GA (US); Asiya Seema Chida, Atlanta, GA (US)

(73) Assignees: Georgia Tech Research Corporation, Atlanta, GA (US); The USA, as Represented by the Secretary, Dept. of Health and Human Services, Bethesda, MD (US)

( * ) Notice: Subject to any disclaimer, the term of this patent is extended or adjusted under 35 U.S.C. 154(b) by 757 days.

(21) Appl. No.: 18/004,534

(22) PCT Filed: Jul. 8, 2021

(86) PCT No.: PCT/US2021/040836

§ 371 (c)(1),
(2) Date: Jan. 6, 2023

(87) PCT Pub. No.: WO2022/011110

PCT Pub. Date: Jan. 13, 2022

(65) Prior Publication Data

US 2023/0242623 A1 Aug. 3, 2023

Related U.S. Application Data

(60) Provisional application No. 63/183,955, filed on May 4, 2021, provisional application No. 63/049,409, filed on Jul. 8, 2020.

(51) Int. Cl.
*A61P 31/14* (2006.01)
*C07K 16/104* (2026.01)
*G01N 33/569* (2006.01)
*A61K 39/00* (2006.01)

(52) U.S. Cl.
CPC ........ *G01N 33/56983* (2013.01); *A61P 31/14* (2018.01); *C07K 16/104* (2026.01); *A61K 2039/505* (2013.01); *G01N 2333/165* (2013.01)

(58) Field of Classification Search
None
See application file for complete search history.

(56) References Cited

U.S. PATENT DOCUMENTS

| | | | |
|---|---|---|---|
| 5,624,821 A | 4/1997 | Winter et al. | |
| 6,005,079 A | 12/1999 | Casterman et al. | |
| 6,194,551 B1 | 2/2001 | Idusogie et al. | |
| 2011/0159001 A1 | 6/2011 | Lanzavecchia | |
| 2020/0392222 A1* | 12/2020 | Pfeifer | C07K 14/54 |

FOREIGN PATENT DOCUMENTS

| | | |
|---|---|---|
| IN | 202041016724 | 6/2020 |
| WO | 94/04678 A1 | 3/1994 |
| WO | 94/25591 A1 | 11/1994 |
| WO | 99/58572 A1 | 11/1999 |
| WO | 2011/025962 A1 | 3/2011 |
| WO | 2020/077190 A1 | 4/2020 |
| WO | 2022/011110 A2 | 1/2022 |

OTHER PUBLICATIONS

Chen, X., et al., “Human monoclonal antibodies block the binding of SARS-CoV-2 spike protein to angiotensin converting enzyme 2 receptor”, cellular & molecular immunology, vol. 17, No. 6, Apr. 2020, pp. 647-649.

Chi, X., et al., “A potent neutralizing human antibody reveals the N-terminal domain of the Spike protein of SARS-CoV-2 as a site of vulnerability”, bioRxiv, May 8, 2020, 23 pages.

Ju, B. et al., “Potent human neutralizing antibodies elicited by SARS-CoV-2 infection,” retrieved from Internet URL: http://www.biorxiv.org/content/10.1101/2020.03.21.990770V2.full.pdf; 42 Pages; Retrieved on Oct. 6, 2020.

Pinto, D. et al., “Structural and functional analysis of a potent sarbecovirus neutralizing antibody,” Retrieved from Internet URL: http://www.biorxiv.org/content/10.1101.2020.04.07.023903v3.full.pdf; 28 pages; Retrieved on Apr. 10, 2020.

Supplementary Partial European Search Report and Search Opinion received for EP Application No. 21838528.4, mailed on Jul. 5, 2024, 17 pages.

Tian, X. et al., “Potent binding of 2019 novel coronavirus spike protein by a SARA coronavirus-specific human monoclonal antibody,” Emerging Microbes & Infections, vol. 9; 4 pages (2020).

Wang, C., et al., “A human monoclonal antibody blocking SARS-CoV-2 infection”, nature communications, vol. 11, No. 1, May 4, 2020, 6 pages.

Wu, Y., et al., “Fully human single-domain antibodies against SARS-CoV-2”, bioRxiv, Mar. 31, 2020, 30 pages.

Angal, S., et al., “A single amino acid substitution abolishes the heterogeneity of chimeric mouse/human (IgG4) antibody,” Immunol., vol. 30, 1993, pp. 105-108.

(Continued)

*Primary Examiner* — Nicole Kinsey White
(74) *Attorney, Agent, or Firm* — Smith Gambrell & Russell LLP

(57) ABSTRACT

Compositions that selectively bind to coronaviruses, including but not limited to SARS-COV-2 and methods of use thereof are provided. The disclosed antibodies and antigen-binding fragments were developed against SARS-CoV-2. The antibodies bind to the spike protein of coronaviruses. The disclosed antibodies are useful for diagnosing, detecting, preventing, and treating coronavirus infections.

20 Claims, 11 Drawing Sheets

Specification includes a Sequence Listing.

(56) References Cited

OTHER PUBLICATIONS

Bachmann, M.F., et al., "Vaccine delivery: a matter of size, geometry, kinetics and molecular patterns," Nat. Rev. Immunol., vol. 10, 2010, pp. 787-796.
Chothia, C., et al., "Canonical structures for the hypervariable regions of immunoglobulins," J. Mol. Biol., vol. 196, 1987 pp. 901-917.
He, Y., et al., "Receptor-binding domain of SARS-CoV spike protein induces highly potent neutralizing antibodies: implication for developing subunit vaccine," Biochemical and Biophysical Research Communications, vol. 324, 2004, pp. 773-778.
International Preliminary Report on Patentability received for PCT Patent Application No. PCT/US21/40836, mailed on Jan. 19, 2023, 10 pages.
International Search Report and Written Opinion received for PCT Patent Application No. PCT/US21/40836, mailed on Dec. 27, 2021, 15 pages.
Konduru, K., et al., "Evaluation of ebolavirus glycoprotein Fc fusion protein as a subunit vaccine (P4417)," The Journal of Immunology, vol. 190, 2013, pp. 205.218.
Levin, D., et al., "Fc fusion as a platform technology: potential for modulating immunogenicity," Trends Biotechnol., vol. 33, 2015, pp. 27-34.
Liu, C. et al., "F(c)gammaRI-targeted fusion proteins result in efficient presentation by human monocytes of antigenic and antagonist T cell epitopes," J. Clin. Invest., vol. 98, 1996, pp. 2001-2007.
Liu, L., et al., "Discovery of a novel coronavirus associated with the recent pneumonia outbreak in humans and its potential bat origin," bioRxiv, 2020, pp. 1-18.
Loureiro, S., et al., "Adjuvant-Free Immunization with Hemagglutinin-Fc Fusion Proteins as an Approach to Influenza Vaccines," Journal of Virology, vol. 85, 2011, pp. 3010-3014.
Lu, L., et al., "A Neonatal Fc Receptor-Targeted Mucosal Vaccine Strategy Effectively Induces HIV-1 Antigen-Specific Immunity to Genital Infection," J. Virol., vol. 85, 2011, pp. 10542-10553.
Mathiowitz, E., et al., "Novel microcapsules for delivery systems", Reactive Polymers, vol. 6, 1987, pp. 275-283.
Mathiowitz, E., et al., "Polyanhydride microspheres as drug carriers I. Hot-melt microencapsulation", Controlled Release, vol. 5, 1987, pp. 13-22.
Mathiowitz, E., et al., "Polyanhydride microspheres as drug carriers. II. Microencapsulation by solvent removal", J. Appl. Polymer Sci., vol. 35, 1988, pp. 755-774.
Mohsen, M.O., et al., "Interaction of Viral Capsid-Derived Virus-Like Particles (VLPs) with the Innate Immune System," Vaccines, vol. 6, No. 37, 2018, 12 pages.
Muyldermans, S., et al., Recognition of antigens by single-domain antibody fragments:the superfluous luxury of paried Trends Biochem. Sci. vol. 26, No. 230, 2001, 6 pages.
Nuttall, S.D., et al., "Immunoglobulin VH Domains and Beyond: Design and Selection of Single-Domain Binding and Reagents," Curr. Pharm. Biotech., vol. 1, No. 253, 2000, 11 pages.
Riechmann, L., et al., "Single domain aintibodies: comparison of camel VH and camelised human VH domainsx," J. Immunol. Meth., vol. 231, No. 25, 1999, 2 pages.
Shang, J., et al., "Structural basis of receptor recognition by SARS-CoV-2," Nature, vol. 581, 2020, pp. 221-224.
Walls, A. C., et al., "Structure, Function, and Antigenicity of the SARS-CoV-2 Spike Glycoprotein," Cell, vol. 181, 2020, pp. 281-292.
Walls, A.C., et al., "Glycan shield and epitope masking of a coronavirus spike protein observed by cryo-electron microscopy," Nat. Struct. Mol. Biol., vol. 23, 2016, pp. 899-905.
Wan, Y., et al., "Molecular Mechanism for Antibody-Dependent Enhancement of Coronavirus Entry," J. Virol., vol. 94, 2020, pp. e2015-e2019.
Wan, Y., et al., "Receptor Recognition by the Novel Coronavirus from Wuhan: an Analysis Based on Decade-Long Structural Studies of SARS Coronavirus," J. Virol., vol. 94, 2020, pp. e00127-e00120.
Wang, Q. H., et al., "Structural and Functional Basis of SARS-CoV-2 Entry by Using Human ACE2," Cell, vol. 181, 2020, pp. 894-904.
Wrapp, D., et al., "Cryo-EM structure of the 2019-nCoV spike in the prefusion conformation," Science, vol. 367, 2020, pp. 1260-1263.
Yang, Z., et al., "Evasion of antibody neutralization in emerging severe acute respiratory syndrome coronaviruses," Proc. Natl. Acad. Sci. U.S.A., vol. 102, 2005, pp. 797-801.
Zhao, L., et al., "Engineering the PP7 Virus Capsid as a Peptide Display Platform," ACS Nano, vol. 13, 2019, pp. 4443-4454.

* cited by examiner

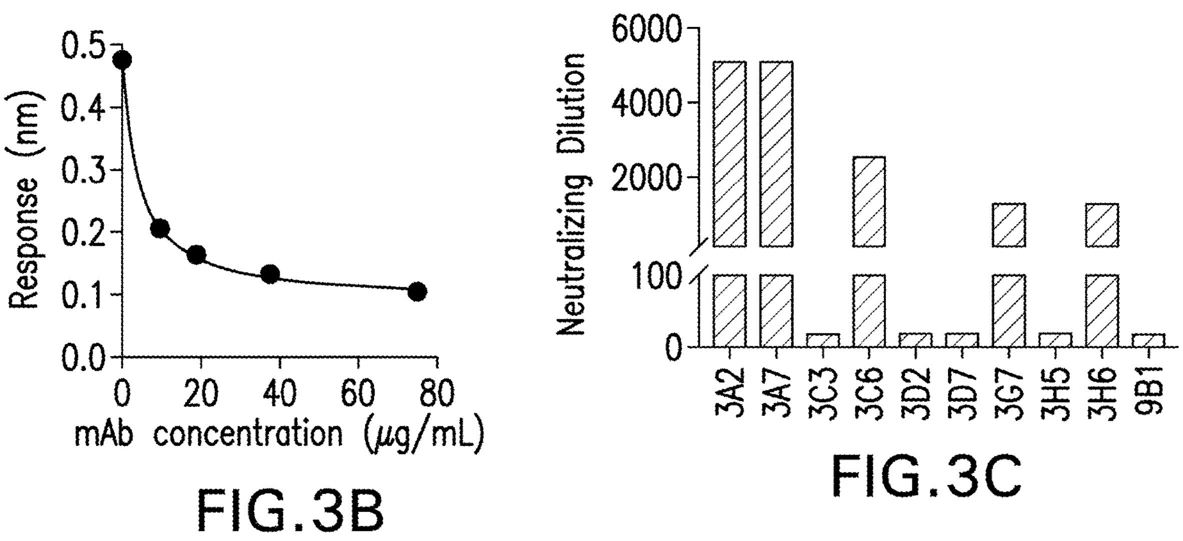
FIG.3B
FIG.3C
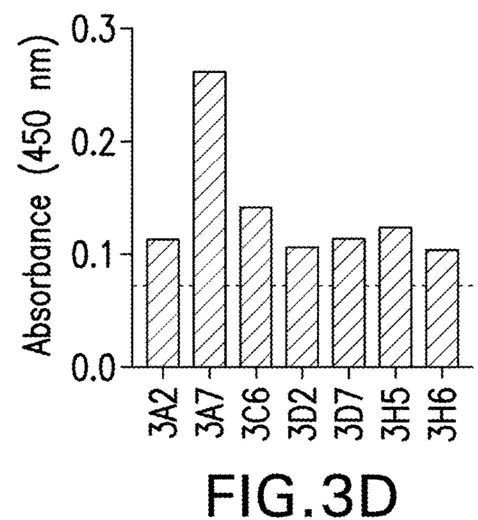
FIG.3D
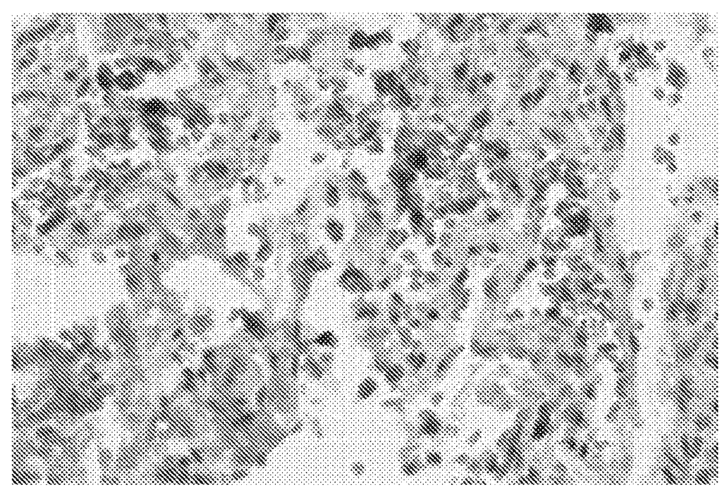
FIG.3E

| Group | | 3A2 * | 3A7 * | 3C6 | 3F5 * | 3G7 | 3H6 | 3D7 | 3F1 | 3D5 | 3H4 | 3F2 * | 3H2 * | 3D2 | 9B1 |
|---|---|---|---|---|---|---|---|---|---|---|---|---|---|---|---|
| Group 1a | 3A2 | −0.001 | −0.019 | −0.008 | −0.056 | 0.009 | −0.006 | 0.303 | 0.257 | 0.318 | 0.344 | 0.367 | 0.274 | 0.176 | 0.079 |
| Group 1a | 3A7 | −0.01 | −0.02 | −0.017 | −0.05 | 0.0033 | −0.021 | 0.272 | 0.268 | 0.282 | 0.275 | 0.359 | 0.27 | 0.164 | 0.058 |
| Group 1a | 3C6 | −0.007 | −0.013 | −0.006 | −0.044 | 0.024 | 0.018 | 0.27 | 0.256 | 0.277 | 0.185 | 0.307 | 0.216 | 0.177 | 0.091 |
| Group 1a | 3F5 | −0.041 | −0.053 | −0.042 | −0.044 | −0.038 | −0.054 | 0.282 | 0.255 | 0.294 | 0.276 | 0.316 | 0.242 | 0.159 | 0.06 |
| Group 1a | 3G7 | −0.003 | −0.016 | −0.01 | −0.026 | 0.008 | 0.256 | 0.265 | 0.314 | 0.291 | 0.238 | 0.302 | 0.201 | 0.198 | 0.059 |
| Group 1b | 3H6 | 0.036 | 0.026 | 0.029 | −0.002 | 0.358 | 0.029 | 0.246 | 0.199 | 0.184 | 0.284 | 0.368 | 0.071 | 0.236 | 0.156 |
| Group 2 | 3D7 | 0.412 | 0.396 | 0.367 | 0.471 | 0.468 | 0.389 | 0.015 | −0.036 | −0.034 | −0.025 | 0.343 | 0.372 | 0.149 | 0.121 |
| Group 2 | 3F1 | 0.31 | 0.244 | 0.242 | 0.29 | 0.325 | 0.203 | −0.047 | −0.04 | −0.034 | −0.043 | 0.324 | 0.287 | 0.186 | 0.101 |
| Group 2 | 3D5 | 0.376 | 0.304 | 0.325 | 0.347 | 0.37 | 0.189 | −0.047 | −0.044 | −0.035 | −0.034 | 0.361 | 0.261 | 0.194 | 0.049 |
| Group 2 | 3H4 | 0.346 | 0.314 | 0.307 | 0.346 | 0.374 | 0.205 | −0.038 | −0.025 | −0.022 | −0.019 | 0.336 | 0.278 | 0.106 | 0.084 |
| Group 3a | 3F2 | 0.315 | 0.245 | 0.26 | 0.223 | 0.369 | 0.338 | 0.325 | 0.315 | 0.312 | 0.245 | −0.035 | −0.065 | 0.249 | 0.066 |
| Group 3b | 3H2 | 0.21 | 0.195 | 0.162 | 0.271 | 0.425 | −0.059 | 0.344 | 0.332 | 0.301 | 0.345 | −0.019 | −0.036 | 0.228 | 0.108 |
| Group 4a | 3D2 | 0.367 | 0.354 | 0.333 | 0.391 | 0.438 | 0.347 | 0.345 | 0.374 | 0.422 | 0.325 | 0.258 | 0.407 | −0.002 | 0.098 |
| Group 4b | 9B1 | 0.316 | 0.323 | 0.292 | 0.291 | 0.409 | 0.332 | 0.367 | 0.372 | 0.261 | 0.312 | 0.275 | 0.309 | 0.239 | 0.005 |

FIG. 4

SEQUENCE LISTING

```
<160> NUMBER OF SEQ ID NOS: 186

<210> SEQ ID NO 1
<211> LENGTH: 119
<212> TYPE: PRT
<213> ORGANISM: Artificial Sequence
<220> FEATURE:
<223> OTHER INFORMATION: Synthetic

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Ser Gly Lys Thr Glu Tyr Asp Pro Asn Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Gly Tyr Asp Val Asn Tyr Glu Leu Asp Tyr Trp Gly Gln Gly
            100                 105                 110

Thr Ser Val Thr Val Ser Ser
        115


<210> SEQ ID NO 2
<211> LENGTH: 107
<212> TYPE: PRT
<213> ORGANISM: Artificial Sequence
<220> FEATURE:
<223> OTHER INFORMATION: Synthetic

<400> SEQUENCE: 2

Asp Ile Gln Met Asn Gln Ser Pro Ser Ser Leu Ser Ala Ser Leu Gly
1               5                   10                  15
```

```
Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105


<210> SEQ ID NO 3
<211> LENGTH: 112
<212> TYPE: PRT
<213> ORGANISM: Artificial Sequence
<220> FEATURE:
<223> OTHER INFORMATION: Synthetic

<400> SEQUENCE: 3

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Ile Ser Leu Phe Val Ile Phe Gly Ser Gly Thr Lys Val Thr Val Leu
            100                 105                 110


<210> SEQ ID NO 4
<211> LENGTH: 113
<212> TYPE: PRT
<213> ORGANISM: Artificial Sequence
<220> FEATURE:
<223> OTHER INFORMATION: Synthetic

<400> SEQUENCE: 4

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
```

```
            100                 105                 110

Lys


<210> SEQ ID NO 5
<211> LENGTH: 116
<212> TYPE: PRT
<213> ORGANISM: Artificial Sequence
<220> FEATURE:
<223> OTHER INFORMATION: Synthetic

<400> SEQUENCE: 5

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Lys Tyr Arg Tyr Asp Ser Phe Ala Tyr Trp Gly Gln Gly Thr Leu Val
            100                 105                 110

Thr Val Ser Ala
        115


<210> SEQ ID NO 6
<211> LENGTH: 111
<212> TYPE: PRT
<213> ORGANISM: Artificial Sequence
<220> FEATURE:
<223> OTHER INFORMATION: Synthetic

<400> SEQUENCE: 6

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met Tyr Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys
            100                 105                 110


<210> SEQ ID NO 7
<211> LENGTH: 117
<212> TYPE: PRT
<213> ORGANISM: Artificial Sequence
<220> FEATURE:
<223> OTHER INFORMATION: Synthetic

<400> SEQUENCE: 7
```

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Asn Lys Asp Asn Ser Lys Ser Gln Val Phe Leu
65                  70                  75                  80

Lys Ile Asn Ser Leu Gln Thr Asp Asp Thr Ala Met Tyr Tyr Cys Gly
                85                  90                  95

Arg Asp Tyr Gly Ile Leu Leu Ile Asp Tyr Trp Gly Gln Gly Thr Thr
            100                 105                 110

Leu Thr Val Ser Ser
        115


<210> SEQ ID NO 8
<211> LENGTH: 106
<212> TYPE: PRT
<213> ORGANISM: Artificial Sequence
<220> FEATURE:
<223> OTHER INFORMATION: Synthetic

<400> SEQUENCE: 8

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile His
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Val Ser Ser Met Glu Ala Glu
65                  70                  75                  80

Asp Val Ala Thr Tyr Tyr Cys Phe Gln Gly Ser Gly Tyr Pro Phe Thr
                85                  90                  95

Phe Gly Ser Gly Thr Lys Leu Glu Ile Lys
            100                 105


<210> SEQ ID NO 9
<211> LENGTH: 122
<212> TYPE: PRT
<213> ORGANISM: Artificial Sequence
<220> FEATURE:
<223> OTHER INFORMATION: Synthetic

<400> SEQUENCE: 9

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Ile Trp Ile Arg Gln Phe Pro Gly Asn Lys Leu Glu Trp
        35                  40                  45

Met Ala Tyr Ile Ser Tyr Ser Gly Thr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80
```

```
Leu Gln Leu Asn Ser Val Thr Thr Glu Asp Thr Ala Thr Tyr Tyr Cys
                85                  90                  95

Ala Gly Arg Arg Gly Ala Tyr Tyr Gly Asn Tyr Glu Glu Asp Tyr Trp
            100                 105                 110

Gly Arg Gly Thr Ser Val Thr Val Ser Ser
        115                 120


<210> SEQ ID NO 10
<211> LENGTH: 106
<212> TYPE: PRT
<213> ORGANISM: Artificial Sequence
<220> FEATURE:
<223> OTHER INFORMATION: Synthetic

<400> SEQUENCE: 10

Gln Ile Val Leu Thr Gln Ser Pro Ala Ile Met Ser Ala Ser Pro Gly
1               5                   10                  15

Glu Lys Val Thr Met Thr Cys Ser Ser Ser Ser Ile Val Asn Tyr Met
            20                  25                  30

Tyr Trp Tyr Gln Gln Lys Pro Gly Ser Ser Pro Arg Leu Leu Ile Tyr
        35                  40                  45

Asp Thr Ser Thr Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Tyr Thr
                85                  90                  95

Phe Gly Gly Gly Thr Lys Leu Glu Ile Lys
            100                 105


<210> SEQ ID NO 11
<211> LENGTH: 122
<212> TYPE: PRT
<213> ORGANISM: Artificial Sequence
<220> FEATURE:
<223> OTHER INFORMATION: Synthetic

<400> SEQUENCE: 11

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Ser Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Ser Tyr Tyr Asp Tyr Asp Gly Gly Gly Cys Phe Asp Tyr Trp
            100                 105                 110

Gly Gln Gly Thr Thr Leu Thr Val Ser Ser
        115                 120


<210> SEQ ID NO 12
<211> LENGTH: 107
<212> TYPE: PRT
```

<213> ORGANISM: Artificial Sequence
<220> FEATURE:
<223> OTHER INFORMATION: Synthetic

<400> SEQUENCE: 12

Arg Ile Val Met Thr Gln Thr Pro Lys Phe Leu Pro Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Pro Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Thr
65                  70                  75                  80

Glu Asp Leu Ala Ile Tyr Phe Cys Gln Gln Gly Tyr Ser Ser Pro Leu
                85                  90                  95

Thr Phe Gly Ala Gly Thr Lys Leu Glu Leu Lys
            100                 105

<210> SEQ ID NO 13
<211> LENGTH: 112
<212> TYPE: PRT
<213> ORGANISM: Artificial Sequence
<220> FEATURE:
<223> OTHER INFORMATION: Synthetic

<400> SEQUENCE: 13

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Asn Thr Ala His
65                  70                  75                  80

Met Glu Leu Leu Ser Leu Thr Ser Glu Asp Ser Ala Val Tyr Tyr Cys
                85                  90                  95

Gly Leu Arg Thr Tyr Trp Gly Gln Gly Thr Leu Val Thr Val Ser Ala
            100                 105                 110

<210> SEQ ID NO 14
<211> LENGTH: 107
<212> TYPE: PRT
<213> ORGANISM: Artificial Sequence
<220> FEATURE:
<223> OTHER INFORMATION: Synthetic

<400> SEQUENCE: 14

Asp Ile Leu Met Thr Gln Ser Pro Ser Ser Met Ser Val Ser Leu Gly
1               5                   10                  15

Asp Thr Val Asn Ile Thr Cys His Ala Ser Gln Asp Ile Asn Asn Asn
            20                  25                  30

Ile Gly Trp Leu Gln Gln Arg Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

```
Ser Gly Ser Gly Thr Asp Tyr Ser Leu Thr Ile Ser Ser Leu Glu Ser
65                  70                  75                  80

Glu Asp Phe Ala Asp Tyr Tyr Cys Val Gln Ser Val Gln Phe Pro Tyr
                85                  90                  95

Thr Phe Gly Gly Gly Thr Lys Leu Glu Ile Lys
            100                 105


<210> SEQ ID NO 15
<211> LENGTH: 121
<212> TYPE: PRT
<213> ORGANISM: Artificial Sequence
<220> FEATURE:
<223> OTHER INFORMATION: Synthetic

<400> SEQUENCE: 15

Glu Val Lys Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asp Thr Lys Tyr Asp Pro Asn Phe
    50                  55                  60

Gln Val Lys Ala Thr Ile Thr Ala Asp Thr Ser Ser Asn Thr Ala Ser
65                  70                  75                  80

Leu Gln Phe Ser Ser Leu Thr Ser Glu Asp Thr Ala Val Tyr Tyr Cys
                85                  90                  95

Ala Arg Ser Tyr Tyr Tyr Gly Thr Thr Ser Trp Phe Ala Ser Trp Gly
            100                 105                 110

Gln Gly Thr Leu Val Thr Val Ser Ala
        115                 120


<210> SEQ ID NO 16
<211> LENGTH: 107
<212> TYPE: PRT
<213> ORGANISM: Artificial Sequence
<220> FEATURE:
<223> OTHER INFORMATION: Synthetic

<400> SEQUENCE: 16

Asp Ile Gln Met Thr Gln Ser Ser Ser Ser Phe Ser Val Ser Leu Gly
1               5                   10                  15

Asp Arg Val Thr Ile Thr Cys Lys Ala Ser Glu Asp Ile Tyr Asn His
            20                  25                  30

Leu Ala Trp Tyr Gln Gln Lys Pro Gly Asn Ala Pro Arg Leu Leu Ile
        35                  40                  45

Ser Gly Ala Pro Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
                85                  90                  95

Thr Phe Gly Gly Gly Thr Lys Leu Glu Ile Lys
            100                 105


<210> SEQ ID NO 17
<211> LENGTH: 122
<212> TYPE: PRT
```

<213> ORGANISM: Artificial Sequence
<220> FEATURE:
<223> OTHER INFORMATION: Synthetic

<400> SEQUENCE: 17

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Ala Ala Asp Thr Ser Ser Asn Thr Ala Tyr
65                  70                  75                  80

Met Gln Leu Ser Ser Leu Thr Ser Glu Asp Thr Ala Val Tyr Tyr Cys
                85                  90                  95

Ala Arg Trp Asp Phe Gly Asn Tyr Val Asp Tyr Ala Met Asp Tyr Trp
            100                 105                 110

Gly Gln Gly Thr Ser Val Thr Val Ser Ser
        115                 120
```

<210> SEQ ID NO 18
<211> LENGTH: 107
<212> TYPE: PRT
<213> ORGANISM: Artificial Sequence
<220> FEATURE:
<223> OTHER INFORMATION: Synthetic

<400> SEQUENCE: 18

```
Asp Ile Lys Met Ile Gln Ser Pro Ser Ser Met Tyr Val Ser Leu Gly
1               5                   10                  15

Glu Arg Val Thr Ile Thr Cys Lys Ala Ser Gln Asp Leu Tyr Ser Phe
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Ala Phe Pro Trp
                85                  90                  95

Thr Phe Gly Gly Gly Thr Lys Leu Glu Ile Lys
            100                 105
```

<210> SEQ ID NO 19
<211> LENGTH: 123
<212> TYPE: PRT
<213> ORGANISM: Artificial Sequence
<220> FEATURE:
<223> OTHER INFORMATION: Synthetic

<400> SEQUENCE: 19

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45
```

```
Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Ser Gln Val
65                  70                  75                  80

Phe Leu Lys Ile Thr Ser Val Asp Thr Val Asp Thr Ala Thr Tyr Tyr
                85                  90                  95

Cys Ala Arg Arg Gly Pro Leu Ile Thr Thr Asp Gly Thr Phe Asp Val
            100                 105                 110

Trp Gly Ala Gly Thr Thr Val Thr Val Ser Ser
        115                 120


<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

Asp Ile Val Met Thr Gln Ser Arg Lys Phe Met Ser Thr Ser Val Gly
1               5                   10                  15

Asp Arg Val Ser Ile Thr Cys Lys Ala Ser Gln Asp Val Gly Thr Ser
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Asn Ser Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Met Lys
            100                 105


<210> SEQ ID NO 21
<211> LENGTH: 123
<212> TYPE: PRT
<213> ORGANISM: Artificial Sequence
<220> FEATURE:
<223> OTHER INFORMATION: Synthetic

<400> SEQUENCE: 21

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Ile Ser Val Asp Thr Val Asp Thr Ala Thr Tyr Tyr
                85                  90                  95

Cys Ala Arg Arg Gly Pro Leu Ile Thr Thr Asp Gly Thr Phe Asp Val
            100                 105                 110

Trp Gly Ala Gly Thr Thr Val Thr Val Ser Ser
```

```
        115                 120


<210> SEQ ID NO 22
<211> LENGTH: 107
<212> TYPE: PRT
<213> ORGANISM: Artificial Sequence
<220> FEATURE:
<223> OTHER INFORMATION: Synthetic

<400> SEQUENCE: 22

Asp Ile Val Met Thr Gln Ser His Lys Phe Leu Ser Thr Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Ile Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Asp Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Glu
            100                 105


<210> SEQ ID NO 23
<211> LENGTH: 122
<212> TYPE: PRT
<213> ORGANISM: Artificial Sequence
<220> FEATURE:
<223> OTHER INFORMATION: Synthetic

<400> SEQUENCE: 23

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Ser Thr Ala His
65                  70                  75                  80

Met Glu Leu Leu Ser Leu Thr Ser Glu Asp Ser Ala Val Tyr Tyr Cys
                85                  90                  95

Gly Arg Gly Leu Tyr Gly Lys Gly Tyr Tyr Tyr Ala Met Asp Tyr Trp
            100                 105                 110

Gly Gln Gly Thr Ser Val Thr Val Ser Ser
        115                 120


<210> SEQ ID NO 24
<211> LENGTH: 119
<212> TYPE: PRT
<213> ORGANISM: Artificial Sequence
<220> FEATURE:
<223> OTHER INFORMATION: Synthetic

<400> SEQUENCE: 24

Gln Val Gln Leu Gln Gln Pro Gly Thr Glu Leu Val Arg Pro Gly Ala
1               5                   10                  15
```

```
Ser Val Lys Leu Ser Cys Lys Ala Ser Gly Tyr Ser Phe Thr Ser Tyr
            20                  25                  30

Trp Met Asn Trp Val Lys Gln Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Ser Ser Gly Tyr Asp Trp Tyr Phe Asp Val Trp Gly Ala Gly
            100                 105                 110

Thr Thr Val Thr Val Ser Ser
        115


<210> SEQ ID NO 25
<211> LENGTH: 111
<212> TYPE: PRT
<213> ORGANISM: Artificial Sequence
<220> FEATURE:
<223> OTHER INFORMATION: Synthetic

<400> SEQUENCE: 25

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp His Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110


<210> SEQ ID NO 26
<211> LENGTH: 119
<212> TYPE: PRT
<213> ORGANISM: Artificial Sequence
<220> FEATURE:
<223> OTHER INFORMATION: Synthetic

<400> SEQUENCE: 26

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ala Phe Thr Ser Tyr
            20                  25                  30

Trp Met Glu Trp Val Lys Gln Arg Pro Gly Gln Gly Leu Glu Trp Ile
        35                  40                  45

Gly Ser Ile Tyr Pro Gly Asp Gly Ala Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Glu Phe Ser Ser Leu Ala Ser Glu Asp Ser Ala Val Tyr Phe Cys
```

```
                85                  90                  95

Ala Arg Ser Gly Gly Tyr Asp Trp Tyr Phe Asp Val Trp Gly Ala Gly
            100                 105                 110

Thr Thr Val Thr Val Ser Ser
        115


<210> SEQ ID NO 27
<211> LENGTH: 111
<212> TYPE: PRT
<213> ORGANISM: Artificial Sequence
<220> FEATURE:
<223> OTHER INFORMATION: Synthetic

<400> SEQUENCE: 27

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Thr Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110


<210> SEQ ID NO 28
<211> LENGTH: 120
<212> TYPE: PRT
<213> ORGANISM: Artificial Sequence
<220> FEATURE:
<223> OTHER INFORMATION: Synthetic

<400> SEQUENCE: 28

Glu Val Gln Leu Gln Gln Ser Gly Ala Glu Leu Val Lys Pro Gly Ala
1               5                   10                  15

Ser Val Thr Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Tyr Tyr Tyr Gly Ser Ser Gly Phe Phe Asp Val Trp Gly Ala
            100                 105                 110

Gly Thr Thr Val Thr Val Ser Ser
        115                 120


<210> SEQ ID NO 29
<211> LENGTH: 106
<212> TYPE: PRT
<213> ORGANISM: Artificial Sequence
<220> FEATURE:
```

<223> OTHER INFORMATION: Synthetic

<400> SEQUENCE: 29

Ser Ile Val Met Thr Gln Thr Pro Lys Phe Leu Leu Val Ser Ala Gly
1 5 10 15

Asp Arg Val Thr Ile Thr Cys Lys Ala Ser Gln Ser Val Ser Asn Asp
20 25 30

Val Ala Trp Tyr Gln Gln Lys Pro Gly Gln Ser Pro Lys Val Leu Ile
35 40 45

Tyr Tyr Ala Ser Asn Arg Tyr Thr Gly Val Pro Asp Arg Phe Thr Gly
50 55 60

Ser Gly Tyr Gly Thr Asp Phe Thr Phe Thr Ile Ser Thr Val Gln Ala
65 70 75 80

Glu Asp Leu Ala Val Tyr Phe Cys Gln Gln Asp Tyr Ser Ser Pro Thr
85 90 95

Phe Gly Ala Gly Thr Lys Leu Glu Leu Lys
100 105

<210> SEQ ID NO 30
<211> LENGTH: 120
<212> TYPE: PRT
<213> ORGANISM: Artificial Sequence
<220> FEATURE:
<223> OTHER INFORMATION: Synthetic

<400> SEQUENCE: 30

Glu Val Gln Leu Gln Gln Ser Gly Ala Glu Leu Val Lys Ser Gly Ala
1 5 10 15

Ser Val Lys Leu Ser Cys Thr Ala Ser Gly Phe Asn Ile Lys Asp Thr
20 25 30

Tyr Met His Trp Val Lys Gln Arg Pro Glu Gln Gly Leu Glu Trp Ile
35 40 45

Gly Arg Ile Asp Pro Ala Ser Gly Asn Thr Lys Tyr Asp Pro Lys Phe
50 55 60

Gln Gly Lys Ala Thr Ile Thr Ser Asp Thr Ser Ser Asn Thr Ala Tyr
65 70 75 80

Leu Gln Leu Ser Ser Leu Thr Ser Glu Asp Thr Ala Val Tyr Phe Cys
85 90 95

Ala Arg Ser Tyr Tyr Thr Tyr Asp Gly Phe Phe Asp Val Trp Gly Ala
100 105 110

Gly Thr Thr Ala Thr Val Ser Ser
115 120

<210> SEQ ID NO 31
<211> LENGTH: 107
<212> TYPE: PRT
<213> ORGANISM: Artificial Sequence
<220> FEATURE:
<223> OTHER INFORMATION: Synthetic

<400> SEQUENCE: 31

Asn Ile Val Met Thr Gln Thr Pro Lys Phe Leu Leu Val Ser Ala Gly
1 5 10 15

Asp Arg Val Thr Ile Thr Cys Lys Ala Ser Gln Ser Val Ser Asn Asp
20 25 30

Val Ala Trp Tyr Gln Gln Lys Pro Gly Gln Ser Pro Lys Leu Leu Ile
35 40 45

Tyr Tyr Ala Ser Asn Arg Tyr Thr Gly Val Pro Asp Arg Phe Thr Gly

```
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Pro
                85                  90                  95

Thr Phe Gly Gly Gly Thr Lys Leu Glu Ile Lys
            100                 105


<210> SEQ ID NO 32
<211> LENGTH: 122
<212> TYPE: PRT
<213> ORGANISM: Artificial Sequence
<220> FEATURE:
<223> OTHER INFORMATION: Synthetic

<400> SEQUENCE: 32

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Trp Ile
        35                  40                  45

Gly Met Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Arg Ser Leu Thr Ser Glu Asp Thr Ala Val Tyr Tyr Cys
                85                  90                  95

Ala Arg Thr Tyr Tyr Tyr Gly Ser Ser Tyr Glu Ala Met Asp Tyr Trp
            100                 105                 110

Gly Gln Gly Thr Ser Val Thr Val Ser Ser
        115                 120


<210> SEQ ID NO 33
<211> LENGTH: 106
<212> TYPE: PRT
<213> ORGANISM: Artificial Sequence
<220> FEATURE:
<223> OTHER INFORMATION: Synthetic

<400> SEQUENCE: 33

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Thr
                85                  90                  95

Phe Gly Gly Gly Thr Lys Leu Glu Ile Lys
            100                 105


<210> SEQ ID NO 34
<211> LENGTH: 119
```

```
<212> TYPE: PRT
<213> ORGANISM: Artificial Sequence
<220> FEATURE:
<223> OTHER INFORMATION: Synthetic

<400> SEQUENCE: 34

Asp Val Gln Leu Gln Glu Ser Gly Pro Asp Leu Val Lys Pro Ser Gln
1               5                   10                  15

Ser Pro Ser Leu Thr Cys Thr Val Thr Gly Tyr Ser Ile Thr Gly Asp
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Ala Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Arg Trp Gly Asn Gly Lys Asn Ala Met Asp Tyr Trp Gly Gln Gly
            100                 105                 110

Thr Ser Val Thr Val Ser Ser
        115


<210> SEQ ID NO 35
<211> LENGTH: 107
<212> TYPE: PRT
<213> ORGANISM: Artificial Sequence
<220> FEATURE:
<223> OTHER INFORMATION: Synthetic

<400> SEQUENCE: 35

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Thr Lys Thr Leu Ala Glu Gly Val Pro Ser Arg Phe Ser Gly
    50                  55                  60

Ser Gly Ser Asp Thr Gln Phe Ser Leu Lys Ile Asn Ser Leu Gln Pro
65                  70                  75                  80

Glu Asp Phe Gly Tyr Tyr Tyr Cys Gln His His Tyr Gly Ser Pro Pro
                85                  90                  95

Thr Phe Gly Gly Gly Thr Lys Leu Glu Ile Lys
            100                 105


<210> SEQ ID NO 36
<211> LENGTH: 120
<212> TYPE: PRT
<213> ORGANISM: Artificial Sequence
<220> FEATURE:
<223> OTHER INFORMATION: Synthetic

<400> SEQUENCE: 36

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
```

```
        35                  40                  45

Met Gly Tyr Ile Ile Tyr Asp Gly Thr Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Ser Glu Asp Thr Ala Thr Tyr Tyr Cys
                85                  90                  95

Ala Arg Val Asp Tyr Asp Val Gly His Trp Phe Ala Tyr Trp Gly Gln
            100                 105                 110

Gly Thr Leu Val Thr Val Ser Ala
        115                 120


<210> SEQ ID NO 37
<211> LENGTH: 106
<212> TYPE: PRT
<213> ORGANISM: Artificial Sequence
<220> FEATURE:
<223> OTHER INFORMATION: Synthetic

<400> SEQUENCE: 37

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys His Gln Phe Thr Thr Ser Pro Trp Thr
                85                  90                  95

Phe Gly Gly Gly Thr Lys Leu Glu Ile Lys
            100                 105


<210> SEQ ID NO 38
<211> LENGTH: 119
<212> TYPE: PRT
<213> ORGANISM: Artificial Sequence
<220> FEATURE:
<223> OTHER INFORMATION: Synthetic

<400> SEQUENCE: 38

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Gln Asp Gly Asn Tyr Trp Phe Ala Tyr Trp Gly Gln Gly
            100                 105                 110
```

```
Thr Leu Val Thr Val Ser Ala
        115


<210> SEQ ID NO 39
<211> LENGTH: 109
<212> TYPE: PRT
<213> ORGANISM: Artificial Sequence
<220> FEATURE:
<223> OTHER INFORMATION: Synthetic

<400> SEQUENCE: 39

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Arg Ile Thr Phe Gly Ala Gly Thr Lys Leu Glu Leu Lys
            100                 105


<210> SEQ ID NO 40
<211> LENGTH: 120
<212> TYPE: PRT
<213> ORGANISM: Artificial Sequence
<220> FEATURE:
<223> OTHER INFORMATION: Synthetic

<400> SEQUENCE: 40

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Ser Thr Tyr
            20                  25                  30

Trp Ile His Trp Val Gln Gln Arg Pro Gly Gln Gly Leu Glu Trp Ile
        35                  40                  45

Gly Tyr Ile Asn Pro Tyr Thr Asp Tyr Thr Glu Tyr Asn Gln Lys Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Tyr Gly Asn Tyr Asp Ala Trp Phe Thr Tyr Trp Gly Gln
            100                 105                 110

Gly Thr Leu Val Thr Val Ser Ala
        115                 120


<210> SEQ ID NO 41
<211> LENGTH: 103
<212> TYPE: PRT
<213> ORGANISM: Artificial Sequence
<220> FEATURE:
<223> OTHER INFORMATION: Synthetic

<400> SEQUENCE: 41

Asp Ile Val Met Thr Gln Ser His Lys Phe Met Ser Thr Ser Val Gly
```

```
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Val Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Arg Thr Phe Gly Gly
                85                  90                  95

Gly Thr Lys Leu Glu Ile Lys
            100


<210> SEQ ID NO 42
<211> LENGTH: 123
<212> TYPE: PRT
<213> ORGANISM: Artificial Sequence
<220> FEATURE:
<223> OTHER INFORMATION: Synthetic

<400> SEQUENCE: 42

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Lys Asp Lys Ala Ile Ile Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Val Ser Gly Tyr Tyr Tyr Tyr Gly Ser Pro Tyr Gly Ala Met Asp Tyr
            100                 105                 110

Trp Gly Gln Gly Thr Ser Val Thr Val Ser Ser
        115                 120


<210> SEQ ID NO 43
<211> LENGTH: 106
<212> TYPE: PRT
<213> ORGANISM: Artificial Sequence
<220> FEATURE:
<223> OTHER INFORMATION: Synthetic

<400> SEQUENCE: 43

Gln Ile Val Leu Thr Gln Ser Pro Ala Ile Met Ser Ala Ser Pro Gly
1               5                   10                  15

Glu Lys Val Thr Ile Ser Cys Ser Ala Thr Ser Ser Val Ser Tyr Met
            20                  25                  30

Tyr Trp Tyr Gln Gln Lys Pro Gly Ser Ser Pro Lys Pro Trp Ile Tyr
        35                  40                  45

His Thr Ser Asn Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80
```

```
Asp Ala Ala Thr Tyr Tyr Cys Gln Gln Tyr His Gly Tyr Pro Leu Thr
                85                  90                  95

Phe Gly Ala Gly Thr Lys Leu Glu Leu Lys
            100                 105


<210> SEQ ID NO 44
<211> LENGTH: 117
<212> TYPE: PRT
<213> ORGANISM: Artificial Sequence
<220> FEATURE:
<223> OTHER INFORMATION: Synthetic

<400> SEQUENCE: 44

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Ser Leu His Trp Val Lys Gln Thr Pro Gly Gln Gly Leu Glu Trp Ile
        35                  40                  45

Gly Ala Val Tyr Pro Gly Asn Asp Asp Thr Ser Tyr Asn Gln Asn Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Tyr Phe Ala Met Asp Tyr Trp Gly Gln Gly Thr Ser
            100                 105                 110

Val Thr Val Ser Ser
        115


<210> SEQ ID NO 45
<211> LENGTH: 113
<212> TYPE: PRT
<213> ORGANISM: Artificial Sequence
<220> FEATURE:
<223> OTHER INFORMATION: Synthetic

<400> SEQUENCE: 45

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Thr Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys His Gln
                85                  90                  95

Tyr Tyr Ser Tyr Pro Trp Thr Phe Gly Gly Gly Thr Lys Leu Glu Ile
            100                 105                 110

Lys


<210> SEQ ID NO 46
<211> LENGTH: 119
<212> TYPE: PRT
<213> ORGANISM: Artificial Sequence
<220> FEATURE:
```

<223> OTHER INFORMATION: Synthetic

<400> SEQUENCE: 46

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Asp Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Thr Arg Tyr Tyr Asp Tyr Val Tyr Ala Met Asp Tyr Trp Gly Gln Gly
            100                 105                 110

Thr Ser Val Thr Val Ser Ser
        115
```

<210> SEQ ID NO 47
<211> LENGTH: 107
<212> TYPE: PRT
<213> ORGANISM: Artificial Sequence
<220> FEATURE:
<223> OTHER INFORMATION: Synthetic

<400> SEQUENCE: 47

```
Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Arg Ile Ser Ser Leu Gln Ala
65                  70                  75                  80

Glu Asp Phe Val Ser Tyr Tyr Cys Gln Gln Leu Tyr Ser Thr Pro Leu
                85                  90                  95

Thr Phe Gly Gly Gly Thr Lys Leu Glu Ile Lys
            100                 105
```

<210> SEQ ID NO 48
<211> LENGTH: 117
<212> TYPE: PRT
<213> ORGANISM: Artificial Sequence
<220> FEATURE:
<223> OTHER INFORMATION: Synthetic

<400> SEQUENCE: 48

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Asn Pro Asn Asn Gly Asp Thr Phe Tyr Asn Gln Lys Phe
```

```
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Gly Tyr Tyr Arg Phe Ala Tyr Trp Gly Gln Gly Thr Leu
            100                 105                 110

Val Thr Val Ser Ala
        115


<210> SEQ ID NO 49
<211> LENGTH: 113
<212> TYPE: PRT
<213> ORGANISM: Artificial Sequence
<220> FEATURE:
<223> OTHER INFORMATION: Synthetic

<400> SEQUENCE: 49

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys


<210> SEQ ID NO 50
<211> LENGTH: 122
<212> TYPE: PRT
<213> ORGANISM: Artificial Sequence
<220> FEATURE:
<223> OTHER INFORMATION: Synthetic

<400> SEQUENCE: 50

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Asn Met His Trp Val Lys Gln Arg Pro Glu Gln Gly Leu Glu Trp Ile
        35                  40                  45

Gly Arg Ile Asp Pro Ala Asn Gly Asp Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Leu Asn Tyr Asp Gly Tyr Tyr Asp Tyr Ala Met Asp Tyr Trp
            100                 105                 110

Gly Gln Gly Thr Ser Val Thr Val Ser Ser
```

```
        115                 120


<210> SEQ ID NO 51
<211> LENGTH: 107
<212> TYPE: PRT
<213> ORGANISM: Artificial Sequence
<220> FEATURE:
<223> OTHER INFORMATION: Synthetic

<400> SEQUENCE: 51

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Phe
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Phe
                85                  90                  95

Thr Phe Gly Ser Gly Thr Lys Leu Glu Ile Lys
            100                 105


<210> SEQ ID NO 52
<211> LENGTH: 118
<212> TYPE: PRT
<213> ORGANISM: Artificial Sequence
<220> FEATURE:
<223> OTHER INFORMATION: Synthetic

<400> SEQUENCE: 52

Gln Val Gln Leu Gln Gln Ser Gly Ala Glu Leu Met Lys Pro Gly Ala
1               5                   10                  15

Ser Val Lys Ile Ser Cys Lys Ala Thr Gly Asn Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Asp Ser Thr Asn Tyr Asn Glu Lys Phe
    50                  55                  60

Lys Gly Lys Ala Thr Phe Thr Ala Asp Thr Ser Ser Lys Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Arg Phe Tyr Trp Tyr Phe Asp Val Trp Gly Ala Gly Thr
            100                 105                 110

Thr Val Thr Val Ser Ser
        115


<210> SEQ ID NO 53
<211> LENGTH: 112
<212> TYPE: PRT
<213> ORGANISM: Artificial Sequence
<220> FEATURE:
<223> OTHER INFORMATION: Synthetic

<400> SEQUENCE: 53

Asp Val Val Met Thr Gln Thr Pro Leu Ser Leu Pro Val Ser Leu Gly
1               5                   10                  15
```

```
Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Val Pro Trp Thr Phe Gly Gly Gly Thr Lys Leu Glu Ile Lys
            100                 105                 110


<210> SEQ ID NO 54
<211> LENGTH: 122
<212> TYPE: PRT
<213> ORGANISM: Artificial Sequence
<220> FEATURE:
<223> OTHER INFORMATION: Synthetic

<400> SEQUENCE: 54

Glu Val Gln Leu Gln Gln Ser Gly Ala Glu Leu Val Lys Pro Gly Ala
1               5                   10                  15

Ser Ile Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Ser Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Ser Tyr Tyr Asp Tyr Asp Gly Gly Gly Cys Phe Asp Tyr Trp
            100                 105                 110

Gly Gln Gly Thr Thr Leu Thr Val Ser Ser
        115                 120


<210> SEQ ID NO 55
<211> LENGTH: 107
<212> TYPE: PRT
<213> ORGANISM: Artificial Sequence
<220> FEATURE:
<223> OTHER INFORMATION: Synthetic

<400> SEQUENCE: 55

Arg Ile Val Met Thr Gln Thr Pro Lys Phe Leu Pro Val Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Pro Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Thr
65                  70                  75                  80

Glu Asp Leu Ala Ile Tyr Phe Cys Gln Gln Gly Tyr Ser Ser Pro Leu
```

```
                85                  90                  95

Thr Phe Gly Ala Gly Thr Lys Leu Glu Leu Lys
            100                 105


<210> SEQ ID NO 56
<211> LENGTH: 121
<212> TYPE: PRT
<213> ORGANISM: Artificial Sequence
<220> FEATURE:
<223> OTHER INFORMATION: Synthetic

<400> SEQUENCE: 56

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asp Asn Phe Ala Met Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Ser Asn Leu Lys Thr Glu Asp Thr Ala Met Tyr
                85                  90                  95

Tyr Cys Ala Ser Tyr Asp Gly Tyr Arg Ala Trp Phe Ala Tyr Trp Gly
            100                 105                 110

Gln Gly Thr Leu Val Thr Val Ser Ala
        115                 120


<210> SEQ ID NO 57
<211> LENGTH: 112
<212> TYPE: PRT
<213> ORGANISM: Artificial Sequence
<220> FEATURE:
<223> OTHER INFORMATION: Synthetic

<400> SEQUENCE: 57

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110


<210> SEQ ID NO 58
<211> LENGTH: 114
<212> TYPE: PRT
<213> ORGANISM: Artificial Sequence
<220> FEATURE:
<223> OTHER INFORMATION: Synthetic

<400> SEQUENCE: 58
```

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Ser Arg Ala Tyr Trp Gly Gln Gly Thr Leu Val Thr Val
            100                 105                 110

Ser Ala


<210> SEQ ID NO 59
<211> LENGTH: 107
<212> TYPE: PRT
<213> ORGANISM: Artificial Sequence
<220> FEATURE:
<223> OTHER INFORMATION: Synthetic

<400> SEQUENCE: 59

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105


<210> SEQ ID NO 60
<211> LENGTH: 121
<212> TYPE: PRT
<213> ORGANISM: Artificial Sequence
<220> FEATURE:
<223> OTHER INFORMATION: Synthetic

<400> SEQUENCE: 60

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Ser Asn Tyr Asn Glu Lys Phe
    50                  55                  60

Lys Ser Lys Ala Thr Leu Thr Val Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Arg Gly Asp Tyr Asp Gly Ser Tyr Trp Tyr Phe Asp Val Trp Gly
            100                 105                 110

Ala Gly Thr Thr Val Thr Val Ser Ser
        115                 120


<210> SEQ ID NO 61
<211> LENGTH: 111
<212> TYPE: PRT
<213> ORGANISM: Artificial Sequence
<220> FEATURE:
<223> OTHER INFORMATION: Synthetic

<400> SEQUENCE: 61

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys
            100                 105                 110


<210> SEQ ID NO 62
<211> LENGTH: 122
<212> TYPE: PRT
<213> ORGANISM: Artificial Sequence
<220> FEATURE:
<223> OTHER INFORMATION: Synthetic

<400> SEQUENCE: 62

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Ile His Trp Val Lys Gln Thr Pro Glu Gln Gly Leu Glu Trp Ile
        35                  40                  45

Gly Ala Ile Tyr Pro Glu Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Asp Gly Tyr Asp Gly Gly Ala His Tyr Gly Leu Asp Tyr Trp
            100                 105                 110

Gly Gln Gly Thr Ser Val Thr Val Ser Ser
        115                 120


<210> SEQ ID NO 63
<211> LENGTH: 111
<212> TYPE: PRT
```

<213> ORGANISM: Artificial Sequence
<220> FEATURE:
<223> OTHER INFORMATION: Synthetic

<400> SEQUENCE: 63

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Phe Ile His Trp Tyr Gln Gln Lys Pro Arg Gln Pro Pro
        35                  40                  45

Lys Phe Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys His His Thr Arg
                85                  90                  95

Glu Leu Pro Trp Thr Phe Gly Gly Gly Thr Lys Leu Glu Ile Lys
            100                 105                 110
```

<210> SEQ ID NO 64
<211> LENGTH: 117
<212> TYPE: PRT
<213> ORGANISM: Artificial Sequence
<220> FEATURE:
<223> OTHER INFORMATION: Synthetic

<400> SEQUENCE: 64

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Ile Tyr Trp Val Lys Gln Ser His Gly Lys Ser Leu Glu Trp Ile
        35                  40                  45

Gly Gly Ile Asn Pro Asn Asn Gly Asp Thr Ile Tyr Asn Gln Asn Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Asp Tyr Gly Gly Ile Ala Tyr Trp Gly Gln Gly Thr Ser
            100                 105                 110

Val Thr Val Ser Ser
        115
```

<210> SEQ ID NO 65
<211> LENGTH: 113
<212> TYPE: PRT
<213> ORGANISM: Artificial Sequence
<220> FEATURE:
<223> OTHER INFORMATION: Synthetic

<400> SEQUENCE: 65

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Phe Gln Gln Lys Pro Gly Gln
        35                  40                  45
```

```
Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Arg Tyr Pro Leu Thr Phe Gly Gly Gly Thr Lys Leu Glu Ile
            100                 105                 110

Lys


<210> SEQ ID NO 66
<211> LENGTH: 120
<212> TYPE: PRT
<213> ORGANISM: Artificial Sequence
<220> FEATURE:
<223> OTHER INFORMATION: Synthetic

<400> SEQUENCE: 66

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Leu Ser Asn Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Ser Ile Tyr Tyr Leu Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ile Leu Arg Ser Gly Asp Thr Ala Met Tyr Tyr Cys Val
                85                  90                  95

Ser Gly Ser Gly Asn Tyr Val Asp Ser Pro Met Asp Tyr Trp Gly Gln
            100                 105                 110

Gly Thr Ser Val Thr Val Ser Ser
        115                 120


<210> SEQ ID NO 67
<211> LENGTH: 104
<212> TYPE: PRT
<213> ORGANISM: Artificial Sequence
<220> FEATURE:
<223> OTHER INFORMATION: Synthetic

<400> SEQUENCE: 67

Gln Val Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
            20                  25                  30

Asn Trp Tyr Gln Gln Lys Ser Gly Thr Ser Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Phe Tyr Cys His Gln Trp Ser Ser Trp Thr Phe Gly
                85                  90                  95

Gly Gly Thr Lys Leu Glu Ile Lys
            100
```

<210> SEQ ID NO 68
<211> LENGTH: 113
<212> TYPE: PRT
<213> ORGANISM: Artificial Sequence
<220> FEATURE:
<223> OTHER INFORMATION: Synthetic

<400> SEQUENCE: 68

```
Glu Val Gln Leu Gln Gln Ser Gly Ala Glu Leu Val Arg Ser Gly Ala
1               5                   10                  15

Ser Val Lys Leu Ser Cys Thr Ala Ser Gly Leu Asn Phe Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Asp Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
                85                  90                  95

Asn Ala Ala Leu Gly Tyr Trp Gly Gln Gly Thr Thr Leu Thr Val Ser
            100                 105                 110

Ser
```

<210> SEQ ID NO 69
<211> LENGTH: 112
<212> TYPE: PRT
<213> ORGANISM: Artificial Sequence
<220> FEATURE:
<223> OTHER INFORMATION: Synthetic

<400> SEQUENCE: 69

```
Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Val
                85                  90                  95

Thr His Val Pro Tyr Thr Phe Gly Gly Gly Thr Lys Leu Glu Ile Lys
            100                 105                 110
```

<210> SEQ ID NO 70
<211> LENGTH: 121
<212> TYPE: PRT
<213> ORGANISM: Artificial Sequence
<220> FEATURE:
<223> OTHER INFORMATION: Synthetic

<400> SEQUENCE: 70

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
```

```
            20                  25                  30

Ser Ile His Trp Val Lys Gln Ala Pro Gly Lys Gly Leu Lys Trp Met
        35                  40                  45

Gly Trp Ile Asn Thr Glu Thr Gly Glu Pro Thr Cys Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ser Thr Tyr Phe Cys
                85                  90                  95

Leu Arg Tyr Trp Gly Ile Tyr Val Glu Trp Tyr Phe Asp Leu Trp Gly
            100                 105                 110

Ala Gly Thr Thr Val Thr Val Ser Ser
        115                 120


<210> SEQ ID NO 71
<211> LENGTH: 112
<212> TYPE: PRT
<213> ORGANISM: Artificial Sequence
<220> FEATURE:
<223> OTHER INFORMATION: Synthetic

<400> SEQUENCE: 71

Asp Val Leu Met Thr Gln Thr Pro Leu Ser Leu Pro Val Arg Leu Gly
1               5                   10                  15

Asp Gln Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Phe
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ser Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110


<210> SEQ ID NO 72
<211> LENGTH: 123
<212> TYPE: PRT
<213> ORGANISM: Artificial Sequence
<220> FEATURE:
<223> OTHER INFORMATION: Synthetic

<400> SEQUENCE: 72

Gln Val Gln Leu Gln Gln Pro Gly Ala Glu Leu Val Arg Pro Gly Ala
1               5                   10                  15

Ser Val Asn Leu Ser Cys Lys Ala Ser Gly Tyr Thr Phe Thr Asn Tyr
            20                  25                  30

Trp Ile Asn Trp Val Arg Gln Arg Pro Gly Gln Gly Leu Glu Trp Ile
        35                  40                  45

Gly Asn Ile Tyr Pro Ser Asp Val Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Asp Asp Ser Ala Val Tyr Tyr Cys
                85                  90                  95
```

```
Thr Arg Ile Tyr Tyr Tyr Ile Ser Ser Tyr Ala Gly Ala Met Asp Tyr
            100                 105                 110

Trp Gly Gln Gly Thr Ser Val Thr Val Ser Ser
        115                 120


<210> SEQ ID NO 73
<211> LENGTH: 107
<212> TYPE: PRT
<213> ORGANISM: Artificial Sequence
<220> FEATURE:
<223> OTHER INFORMATION: Synthetic

<400> SEQUENCE: 73

Asn Ile Val Leu Thr Gln Ser Pro Arg Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Ser Leu Thr Ile Ser Ser Val Gln Ala
65                  70                  75                  80

Glu Asp Leu Ala Asp Tyr His Cys Gly Gln Ser Phe Ser Tyr Pro Leu
                85                  90                  95

Thr Phe Gly Ala Gly Thr Lys Leu Glu Leu Lys
            100                 105


<210> SEQ ID NO 74
<211> LENGTH: 120
<212> TYPE: PRT
<213> ORGANISM: Artificial Sequence
<220> FEATURE:
<223> OTHER INFORMATION: Synthetic

<400> SEQUENCE: 74

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met Gln Trp Val Lys Gln Ala Pro Gly Lys Gly Leu Lys Trp Met
        35                  40                  45

Gly Trp Ile Asn Thr Glu Thr Gly Glu Pro Thr Tyr Thr Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Ile Leu Lys Asn Glu Asp Thr Ala Thr Tyr Phe Cys
                85                  90                  95

Ala Arg Pro His Tyr Asp Tyr Tyr Trp Tyr Phe Asp Val Trp Gly Ala
            100                 105                 110

Gly Thr Thr Val Thr Val Ser Ser
        115                 120


<210> SEQ ID NO 75
<211> LENGTH: 112
<212> TYPE: PRT
<213> ORGANISM: Artificial Sequence
<220> FEATURE:
<223> OTHER INFORMATION: Synthetic
```

<400> SEQUENCE: 75

```
Asp Val Leu Met Thr Gln Ile Pro Leu Ser Leu Pro Val Ser Leu Gly
1               5                   10                  15

Asn Gln Ala Ser Ile Ser Cys Arg Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Lys Ile Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ala Pro Pro Thr Phe Gly Ala Gly Thr Lys Leu Glu Leu Lys
            100                 105                 110
```

<210> SEQ ID NO 76
<211> LENGTH: 113
<212> TYPE: PRT
<213> ORGANISM: Artificial Sequence
<220> FEATURE:
<223> OTHER INFORMATION: Synthetic

<400> SEQUENCE: 76

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Thr
            20                  25                  30

Trp Met His Trp Val Lys Gln Arg Pro Gly Gln Gly Leu Glu Trp Ile
        35                  40                  45

Gly Thr Ile Asp Pro Ser Asp Ser Tyr Ala Ser Tyr Asn Gln Lys Phe
    50                  55                  60

Lys Gly Lys Ala Thr Leu Thr Val His Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ala Asn Leu Asp Tyr Trp Gly Gln Gly Thr Thr Leu Thr Val Ser
            100                 105                 110

Ser
```

<210> SEQ ID NO 77
<211> LENGTH: 112
<212> TYPE: PRT
<213> ORGANISM: Artificial Sequence
<220> FEATURE:
<223> OTHER INFORMATION: Synthetic

<400> SEQUENCE: 77

```
Asp Val Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Asn Ser
            20                  25                  30

Tyr Gly Asn Thr Tyr Leu Ser Trp Tyr Leu His Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
```

```
65                  70                  75                  80

Ser Thr Ile Lys Pro Glu Asp Leu Gly Met Tyr Tyr Cys Leu Gln Gly
                85                  90                  95

Thr His Gln Pro Tyr Thr Phe Gly Gly Gly Thr Lys Leu Glu Ile Lys
            100                 105                 110


<210> SEQ ID NO 78
<211> LENGTH: 120
<212> TYPE: PRT
<213> ORGANISM: Artificial Sequence
<220> FEATURE:
<223> OTHER INFORMATION: Synthetic

<400> SEQUENCE: 78

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Ala Ile Asn Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Ala Arg His Pro Leu Gly Leu Pro Ser Trp Phe Ala Tyr Trp Gly Gln
            100                 105                 110

Gly Thr Leu Val Thr Val Ser Ala
        115                 120


<210> SEQ ID NO 79
<211> LENGTH: 107
<212> TYPE: PRT
<213> ORGANISM: Artificial Sequence
<220> FEATURE:
<223> OTHER INFORMATION: Synthetic

<400> SEQUENCE: 79

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Arg
                85                  90                  95

Thr Phe Gly Gly Gly Thr Lys Leu Glu Ile Lys
            100                 105


<210> SEQ ID NO 80
<211> LENGTH: 123
<212> TYPE: PRT
<213> ORGANISM: Artificial Sequence
<220> FEATURE:
```

<223> OTHER INFORMATION: Synthetic

<400> SEQUENCE: 80

Gln Val Gln Leu Gln Gln Ser Gly Pro Glu Leu Val Lys Pro Gly Ala
1 5 10 15

Ser Val Arg Ile Ser Cys Lys Ala Ser Gly Tyr Thr Phe Thr Ser Tyr
20 25 30

Tyr Ile His Trp Val Lys Gln Arg Pro Gly Gln Gly Leu Glu Trp Ile
35 40 45

Gly Trp Ile Tyr Pro Gly Asn Val Asn Thr Lys Tyr Asn Glu Lys Phe
50 55 60

Lys Gly Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Phe Cys
85 90 95

Ala Arg Arg Gly Ile Tyr Tyr Arg Tyr Asp Asp Tyr Ala Met Asp Tyr
100 105 110

Trp Gly Gln Gly Thr Ser Val Thr Val Ser Ser
115 120

<210> SEQ ID NO 81
<211> LENGTH: 111
<212> TYPE: PRT
<213> ORGANISM: Artificial Sequence
<220> FEATURE:
<223> OTHER INFORMATION: Synthetic

<400> SEQUENCE: 81

Asn Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Asp Ser Tyr
20 25 30

Gly Asn Ser Phe Met His Trp Tyr Gln Gln Lys Pro Gly Gln Pro Pro
35 40 45

Lys Leu Leu Ile Tyr Leu Ala Ser Asn Leu Glu Ser Gly Val Pro Ala
50 55 60

Arg Phe Ser Gly Ser Gly Ser Arg Thr Asp Phe Thr Leu Thr Ile Asp
65 70 75 80

Pro Val Glu Ala Asp Asp Ala Ala Thr Tyr Tyr Cys Gln Gln Asn Asn
85 90 95

Glu Asp Pro Trp Thr Phe Gly Gly Gly Thr Lys Leu Glu Ile Lys
100 105 110

<210> SEQ ID NO 82
<211> LENGTH: 122
<212> TYPE: PRT
<213> ORGANISM: Artificial Sequence
<220> FEATURE:
<223> OTHER INFORMATION: Synthetic

<400> SEQUENCE: 82

Glu Val Gln Leu Gln Gln Ser Gly Ala Glu Leu Val Lys Pro Gly Ala
1 5 10 15

Ser Val Lys Leu Ser Cys Thr Ala Ser Gly Phe Asn Ile Lys Asp Ala
20 25 30

Tyr Met His Trp Met Lys Gln Arg Pro Glu Gln Gly Leu Glu Trp Ile
35 40 45

Gly Arg Ile Asp Pro Ala Asn Gly Asn Thr Lys Tyr Asp Pro Lys Phe

```
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Lys Gly Gly Tyr Tyr Leu Tyr Tyr His Ala Met Asp Cys Trp
            100                 105                 110

Gly Gln Gly Thr Ser Val Thr Val Ser Ser
        115                 120


<210> SEQ ID NO 83
<211> LENGTH: 111
<212> TYPE: PRT
<213> ORGANISM: Artificial Sequence
<220> FEATURE:
<223> OTHER INFORMATION: Synthetic

<400> SEQUENCE: 83

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Phe Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Pro Thr Phe Gly Ser Gly Thr Lys Leu Glu Ile Lys
            100                 105                 110


<210> SEQ ID NO 84
<211> LENGTH: 119
<212> TYPE: PRT
<213> ORGANISM: Artificial Sequence
<220> FEATURE:
<223> OTHER INFORMATION: Synthetic

<400> SEQUENCE: 84

Gln Val Gln Ile Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ile Tyr
            20                  25                  30

Trp Met Gln Trp Val Lys Gln Arg Pro Gly Gln Gly Leu Glu Trp Ile
        35                  40                  45

Gly Ser Ile Tyr Pro Gly Asp Gly Asn Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Tyr Cys
                85                  90                  95

Ala Arg Ser Val Thr Tyr Asp Trp Tyr Phe Asp Val Trp Gly Ala Gly
            100                 105                 110

Thr Thr Val Thr Val Ser Ser
        115
```

<210> SEQ ID NO 85
<211> LENGTH: 111
<212> TYPE: PRT
<213> ORGANISM: Artificial Sequence
<220> FEATURE:
<223> OTHER INFORMATION: Synthetic

<400> SEQUENCE: 85

```
Asp Ile Val Val Thr His Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Val Pro Trp Thr Phe Gly Gly Gly Thr Lys Leu Glu Ile Lys
            100                 105                 110
```

<210> SEQ ID NO 86
<211> LENGTH: 122
<212> TYPE: PRT
<213> ORGANISM: Artificial Sequence
<220> FEATURE:
<223> OTHER INFORMATION: Synthetic

<400> SEQUENCE: 86

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Tyr Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Thr Arg Trp Asp Tyr Asp Gly Tyr Tyr Glu Asn Thr Met Asp Tyr Trp
            100                 105                 110

Gly Gln Gly Thr Ser Val Thr Val Ser Ser
        115                 120
```

<210> SEQ ID NO 87
<211> LENGTH: 107
<212> TYPE: PRT
<213> ORGANISM: Artificial Sequence
<220> FEATURE:
<223> OTHER INFORMATION: Synthetic

<400> SEQUENCE: 87

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
```

```
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105


<210> SEQ ID NO 88
<211> LENGTH: 120
<212> TYPE: PRT
<213> ORGANISM: Artificial Sequence
<220> FEATURE:
<223> OTHER INFORMATION: Synthetic

<400> SEQUENCE: 88

Asp Val Gln Leu Val Ala Ser Gly Gly Gly Leu Val Gln Pro Gly Gly
1               5                   10                  15

Ser Arg Lys Leu Ser Cys Ala Ala Ser Gly Phe Thr Phe Ser Asn Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Thr Asp Thr Leu
    50                  55                  60

Lys Gly Arg Phe Thr Ile Ser Arg Asp Asn Pro Lys Asn Thr Leu Phe
65                  70                  75                  80

Leu His Met Thr Ser Leu Thr Ser Glu Asp Thr Ala Met Tyr Tyr Cys
                85                  90                  95

Val Arg Ser Ala His Gly Tyr Tyr Gly Trp Phe Ala Tyr Trp Gly Gln
            100                 105                 110

Gly Thr Leu Val Thr Val Ser Ala
        115                 120


<210> SEQ ID NO 89
<211> LENGTH: 113
<212> TYPE: PRT
<213> ORGANISM: Artificial Sequence
<220> FEATURE:
<223> OTHER INFORMATION: Synthetic

<400> SEQUENCE: 89

Asp Ile Val Met Ser Gln Ser Pro Ser Ser Leu Ala Val Ser Val Gly
1               5                   10                  15

Glu Lys Val Thr Met Ser Cys Met Ser Ser Gln Ser Leu Leu Tyr Ser
            20                  25                  30

Thr Asp Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95
```

```
Tyr Tyr Ser Tyr Pro Trp Thr Phe Gly Gly Gly Thr Lys Leu Glu Ile
            100                 105                 110

Lys


<210> SEQ ID NO 90
<211> LENGTH: 117
<212> TYPE: PRT
<213> ORGANISM: Artificial Sequence
<220> FEATURE:
<223> OTHER INFORMATION: Synthetic

<400> SEQUENCE: 90

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Ile
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Lys Thr Lys Tyr Asp Pro Lys Phe
    50                  55                  60

Gln Gly Lys Ala Thr Ile Ile Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Thr Pro Asp Tyr Tyr Gly Ser Tyr Trp Gly Gln Gly Thr Leu
            100                 105                 110

Val Thr Val Ser Ala
        115


<210> SEQ ID NO 91
<211> LENGTH: 111
<212> TYPE: PRT
<213> ORGANISM: Artificial Sequence
<220> FEATURE:
<223> OTHER INFORMATION: Synthetic

<400> SEQUENCE: 91

Asp Ile Val Leu Thr Gln Ser Pro Ala Ser Leu Ala Val Ser Leu Gly
1               5                   10                  15

Gln Arg Ala Thr Ile Phe Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Arg Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu Ile Arg
            100                 105                 110


<210> SEQ ID NO 92
<211> LENGTH: 118
<212> TYPE: PRT
<213> ORGANISM: Artificial Sequence
<220> FEATURE:
<223> OTHER INFORMATION: Synthetic

<400> SEQUENCE: 92
```

```
Glu Val Gln Leu Gln Gln Ser Gly Pro Glu Leu Val Lys Pro Gly Ser
1               5                   10                  15

Ser Val Lys Ile Ser Cys Lys Thr Ser Gly Tyr Ile Phe Thr Glu Tyr
            20                  25                  30

Thr Met Tyr Trp Val Lys Gln Ser His Gly Lys Ser Leu Glu Trp Ile
        35                  40                  45

Gly Gly Asn Asn Pro Asn Thr Gly Asp Thr Thr Tyr Asn Gln Lys Phe
    50                  55                  60

Lys Gly Lys Ala Thr Leu Thr Val Asp Lys Ser Ser Gly Thr Ala Tyr
65                  70                  75                  80

Leu Glu Leu Arg Ser Leu Thr Ser Glu Asp Ser Ala Val Tyr Tyr Cys
                85                  90                  95

Ala Arg Asp Arg Tyr Asp Arg Ala Met Asp Tyr Trp Gly Gln Gly Thr
            100                 105                 110

Ser Val Thr Val Ser Ser
        115


<210> SEQ ID NO 93
<211> LENGTH: 107
<212> TYPE: PRT
<213> ORGANISM: Artificial Sequence
<220> FEATURE:
<223> OTHER INFORMATION: Synthetic

<400> SEQUENCE: 93

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Asn Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
                85                  90                  95

Thr Phe Gly Ala Gly Thr Lys Leu Glu Leu Lys
            100                 105


<210> SEQ ID NO 94
<211> LENGTH: 122
<212> TYPE: PRT
<213> ORGANISM: Artificial Sequence
<220> FEATURE:
<223> OTHER INFORMATION: Synthetic

<400> SEQUENCE: 94

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Met Tyr Trp Asp Asp Asp Lys Arg Tyr Asn Pro Ser
    50                  55                  60

Leu Lys Ser Arg Leu Thr Ile Ser Lys Ser Thr Ser Ser Asn Gln Val
```

```
65                  70                  75                  80

Phe Leu Lys Ile Thr Ser Val Asp Thr Ala Asp Thr Ala Thr Tyr Tyr
                85                  90                  95

Cys Ala Arg Arg Glu Ile His Asp Phe Asp Gly Trp Phe Ala Tyr Trp
            100                 105                 110

Gly Gln Gly Thr Leu Val Thr Val Ser Ala
        115                 120


<210> SEQ ID NO 95
<211> LENGTH: 107
<212> TYPE: PRT
<213> ORGANISM: Artificial Sequence
<220> FEATURE:
<223> OTHER INFORMATION: Synthetic

<400> SEQUENCE: 95

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Ser Ser
            20                  25                  30

Val Ala Trp Tyr Gln Gln Lys Pro Gly Gln Ser Pro Lys Ala Leu Val
        35                  40                  45

Tyr Ser Ala Ser Ser Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys
            100                 105


<210> SEQ ID NO 96
<211> LENGTH: 120
<212> TYPE: PRT
<213> ORGANISM: Artificial Sequence
<220> FEATURE:
<223> OTHER INFORMATION: Synthetic

<400> SEQUENCE: 96

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Arg Tyr Asn Asp Gly Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Asp Tyr Gly Tyr Asp Tyr Thr Met Asp Tyr Trp Gly Gln
            100                 105                 110

Gly Thr Ser Val Thr Val Ser Ser
        115                 120


<210> SEQ ID NO 97
<211> LENGTH: 111
```

```
<212> TYPE: PRT
<213> ORGANISM: Artificial Sequence
<220> FEATURE:
<223> OTHER INFORMATION: Synthetic

<400> SEQUENCE: 97

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Thr Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Ala Ala Met Tyr Phe Cys Gln Gln Thr Lys
                85                  90                  95

Glu Val Pro Tyr Thr Phe Gly Gly Gly Thr Lys Leu Glu Ile Lys
            100                 105                 110


<210> SEQ ID NO 98
<211> LENGTH: 118
<212> TYPE: PRT
<213> ORGANISM: Artificial Sequence
<220> FEATURE:
<223> OTHER INFORMATION: Synthetic

<400> SEQUENCE: 98

Glu Val Gln Leu Gln Gln Ser Gly Ala Glu Leu Val Arg Pro Gly Ala
1               5                   10                  15

Leu Val Lys Leu Ser Cys Asn Ala Ser Gly Phe Asn Ile Lys Asp Tyr
            20                  25                  30

Phe Met Asn Trp Val Lys Gln Arg Pro Glu Gln Gly Leu Glu Trp Ile
        35                  40                  45

Gly Trp Ile Asp Pro Glu Asn Gly Asn Ser Ile Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Thr Arg Asp Gly Gly Ala Trp Phe Ala Tyr Trp Gly Gln Gly Thr
            100                 105                 110

Leu Val Thr Val Ser Ala
        115


<210> SEQ ID NO 99
<211> LENGTH: 107
<212> TYPE: PRT
<213> ORGANISM: Artificial Sequence
<220> FEATURE:
<223> OTHER INFORMATION: Synthetic

<400> SEQUENCE: 99

Gly Ile Val Met Thr Gln Ser Gln Lys Phe Met Ser Ala Ser Val Gly
1               5                   10                  15

Asp Arg Val Ser Val Thr Cys Lys Ala Ser Gln Asn Val Val Thr Asn
            20                  25                  30

Val Ala Trp Tyr Gln Gln Lys Pro Gly Gln Ser Pro Lys Ala Leu Ile
```

```
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ser Gly Thr Asn Leu Glu Ile Lys
            100                 105


<210> SEQ ID NO 100
<211> LENGTH: 119
<212> TYPE: PRT
<213> ORGANISM: Artificial Sequence
<220> FEATURE:
<223> OTHER INFORMATION: Synthetic

<400> SEQUENCE: 100

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Ile His Trp Val Lys Gln Thr Pro Gly Gln Gly Leu Glu Trp Ile
        35                  40                  45

Gly Ala Ile Tyr Pro Gly Asn Gly Asp Ile Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Asp Gly Asp Tyr Val Arg Gly Phe Ala Tyr Trp Gly Gln Gly
            100                 105                 110

Thr Leu Val Thr Val Ser Ala
        115


<210> SEQ ID NO 101
<211> LENGTH: 111
<212> TYPE: PRT
<213> ORGANISM: Artificial Sequence
<220> FEATURE:
<223> OTHER INFORMATION: Synthetic

<400> SEQUENCE: 101

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Tyr Ser Phe Met His Trp Tyr Leu Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Glu
65                  70                  75                  80

Pro Val Glu Ala Asp Asp Ala Ala Thr Tyr Tyr Cys Gln Gln Asn Asn
                85                  90                  95

Glu Asp Pro Trp Thr Leu Gly Gly Gly Thr Lys Leu Glu Ile Lys
            100                 105                 110
```

<210> SEQ ID NO 102
<211> LENGTH: 116
<212> TYPE: PRT
<213> ORGANISM: Artificial Sequence
<220> FEATURE:
<223> OTHER INFORMATION: Synthetic

<400> SEQUENCE: 102

```
Asp Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Ile Pro Glu Lys Arg Leu Glu Trp Val
        35                  40                  45

Ala Tyr Ile Ser Ser Gly Gly Gly Ser Thr Asp Tyr Leu Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Asn Trp Asp Phe Asp Tyr Trp Gly Gln Gly Thr Pro Leu
            100                 105                 110

Thr Val Ser Ser
        115
```

<210> SEQ ID NO 103
<211> LENGTH: 107
<212> TYPE: PRT
<213> ORGANISM: Artificial Sequence
<220> FEATURE:
<223> OTHER INFORMATION: Synthetic

<400> SEQUENCE: 103

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ser Ala
            20                  25                  30

Val Ala Trp Tyr Gln Gln Lys Ala Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Ser Gly Thr Pro Leu
                85                  90                  95

Thr Phe Gly Ala Gly Thr Lys Leu Glu Leu Lys
            100                 105
```

<210> SEQ ID NO 104
<211> LENGTH: 119
<212> TYPE: PRT
<213> ORGANISM: Artificial Sequence
<220> FEATURE:
<223> OTHER INFORMATION: Synthetic

<400> SEQUENCE: 104

```
Gln Val Gln Leu Gln Gln Ser Gly Pro Glu Leu Val Lys Pro Gly Ala
1               5                   10                  15

Ser Val Lys Ile Ser Cys Gly Ala Ser Gly Tyr Thr Phe Thr Asn Tyr
```

```
            20                  25                  30

Phe Ile His Trp Val Arg Gln Arg Pro Gly Gln Gly Leu Glu Trp Ile
        35                  40                  45

Gly Trp Ile Tyr Pro Gly Asp Val Asn Thr Gln Tyr Asn Glu Arg Phe
    50                  55                  60

Lys Asp Lys Ala Ile Leu Thr Ala Asp Lys Ser Ser Thr Thr Ala Tyr
65                  70                  75                  80

Met Gln Leu Thr Ser Leu Thr Ser Glu Asp Ser Ala Val Tyr Phe Cys
                85                  90                  95

Thr Arg Arg Gln Asn Phe Gly Ser Phe Phe Asp Tyr Trp Gly Gln Gly
            100                 105                 110

Thr Thr Leu Thr Val Ser Ser
        115


<210> SEQ ID NO 105
<211> LENGTH: 107
<212> TYPE: PRT
<213> ORGANISM: Artificial Sequence
<220> FEATURE:
<223> OTHER INFORMATION: Synthetic

<400> SEQUENCE: 105

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Ala Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr His Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Asn Leu Glu Ile Lys
            100                 105


<210> SEQ ID NO 106
<211> LENGTH: 119
<212> TYPE: PRT
<213> ORGANISM: Artificial Sequence
<220> FEATURE:
<223> OTHER INFORMATION: Synthetic

<400> SEQUENCE: 106

Gln Val Gln Leu Glu Gln Ser Gly Pro Glu Leu Val Arg Pro Gly Thr
1               5                   10                  15

Ser Val Lys Met Ser Cys Lys Ala Ser Gly Tyr Ala Phe Thr Ser Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Ile Lys Asp Asn Glu Lys Phe
    50                  55                  60

Arg Gly Lys Ala Thr Leu Thr Ala Asp Lys Ser Ser Asn Thr Ala Phe
65                  70                  75                  80

Leu Gln Leu Ser Ser Leu Thr Ser Asp Asp Ser Ala Leu Tyr Phe Cys
                85                  90                  95
```

```
Thr Arg Asn Leu Pro Gly Ser Gly Tyr Phe Asp Val Trp Gly Ala Gly
            100                 105                 110

Thr Thr Val Thr Val Ser Ser
        115


<210> SEQ ID NO 107
<211> LENGTH: 106
<212> TYPE: PRT
<213> ORGANISM: Artificial Sequence
<220> FEATURE:
<223> OTHER INFORMATION: Synthetic

<400> SEQUENCE: 107

Glu Ile Leu Leu Thr Gln Ser Pro Ala Ile Ile Ala Ala Ser Pro Gly
1               5                   10                  15

Glu Lys Val Thr Ile Thr Cys Ser Ala Ser Ser Ser Val Ser Tyr Met
            20                  25                  30

Asn Trp Tyr Gln Gln Lys Pro Gly Ser Ser Pro Lys Ile Trp Ile Tyr
        35                  40                  45

Gly Ile Ser Asn Leu Ala Ser Gly Val Pro Ala Arg Phe Ser Gly Ser
    50                  55                  60

Gly Ser Gly Thr Ser Phe Ser Phe Thr Ile Asn Ser Met Glu Ala Glu
65                  70                  75                  80

Asp Val Ala Thr Tyr Tyr Cys Gln Gln Arg Ser Gly Tyr Pro Leu Thr
                85                  90                  95

Phe Gly Ala Gly Thr Lys Leu Glu Leu Lys
            100                 105


<210> SEQ ID NO 108
<211> LENGTH: 117
<212> TYPE: PRT
<213> ORGANISM: Artificial Sequence
<220> FEATURE:
<223> OTHER INFORMATION: Synthetic

<400> SEQUENCE: 108

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Gly Trp Phe Ser Tyr Tyr Leu Asp Tyr Trp Gly Gln Gly Thr Thr
            100                 105                 110

Leu Thr Val Ser Ser
        115


<210> SEQ ID NO 109
<211> LENGTH: 107
<212> TYPE: PRT
<213> ORGANISM: Artificial Sequence
<220> FEATURE:
<223> OTHER INFORMATION: Synthetic
```

<400> SEQUENCE: 109

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Ser Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Asp Asn Thr Trp
                85                  90                  95

Thr Phe Gly Gly Gly Thr Lys Leu Glu Ile Lys
            100                 105
```

<210> SEQ ID NO 110
<211> LENGTH: 117
<212> TYPE: PRT
<213> ORGANISM: Artificial Sequence
<220> FEATURE:
<223> OTHER INFORMATION: Synthetic

<400> SEQUENCE: 110

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Ile Tyr Trp Val Lys Gln Ser His Gly Lys Ser Leu Glu Trp Ile
        35                  40                  45

Gly Gly Ile Asn Pro Asn Asn Gly Asp Thr Ile Tyr Asn Gln Asn Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Asp Tyr Gly Gly Ile Ala Tyr Trp Gly Gln Gly Thr Leu
            100                 105                 110

Val Thr Val Ser Ala
        115
```

<210> SEQ ID NO 111
<211> LENGTH: 113
<212> TYPE: PRT
<213> ORGANISM: Artificial Sequence
<220> FEATURE:
<223> OTHER INFORMATION: Synthetic

<400> SEQUENCE: 111

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Phe Gln Gln Lys Pro Gly Gln
        35                  40                  45

Ser Pro Lys Leu Leu Ile Tyr Trp Ala Ser Thr Arg Glu Ser Gly Val
    50                  55                  60
```

```
Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Arg Tyr Pro Leu Thr Phe Gly Ala Gly Thr Lys Leu Glu Leu
            100                 105                 110

Lys


<210> SEQ ID NO 112
<211> LENGTH: 122
<212> TYPE: PRT
<213> ORGANISM: Artificial Sequence
<220> FEATURE:
<223> OTHER INFORMATION: Synthetic

<400> SEQUENCE: 112

Glu Val Gln Leu Gln Gln Ser Gly Pro Glu Leu Val Arg Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Gly Ile Asn Pro Asn Asn Gly Asp Thr Thr Tyr Asn Gln Arg Phe
    50                  55                  60

Lys Gly Arg Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Pro Arg Glu Asp Tyr Arg Asn Asp Glu Lys Ile Pro Phe Asp Tyr Trp
            100                 105                 110

Gly Gln Gly Thr Thr Leu Thr Val Ser Ser
        115                 120


<210> SEQ ID NO 113
<211> LENGTH: 113
<212> TYPE: PRT
<213> ORGANISM: Artificial Sequence
<220> FEATURE:
<223> OTHER INFORMATION: Synthetic

<400> SEQUENCE: 113

Asp Ile Val Met Ser Gln Ser Pro Ser Ser Leu Thr Val Ser Val Gly
1               5                   10                  15

Glu Asn Ile Thr Met Ser Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Phe Pro Leu Thr Phe Gly Ala Gly Thr Lys Leu Asp Leu
            100                 105                 110

Lys
```

<210> SEQ ID NO 114
<211> LENGTH: 118
<212> TYPE: PRT
<213> ORGANISM: Artificial Sequence
<220> FEATURE:
<223> OTHER INFORMATION: Synthetic

<400> SEQUENCE: 114

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Phe Met Thr Trp Val Lys Gln Asn His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Ala Val Asp Lys Ser Ser Ser Thr Ala His
65                  70                  75                  80

Met Glu Leu Leu Ser Leu Thr Ser Glu Asp Ser Ala Val Tyr Tyr Cys
                85                  90                  95

Gly Arg Phe Tyr Arg Asn Gly Asp Phe Asp Val Trp Gly Ala Gly Thr
            100                 105                 110

Thr Val Thr Val Ser Ser
        115
```

<210> SEQ ID NO 115
<211> LENGTH: 107
<212> TYPE: PRT
<213> ORGANISM: Artificial Sequence
<220> FEATURE:
<223> OTHER INFORMATION: Synthetic

<400> SEQUENCE: 115

```
Asp Ile Val Met Thr Gln Ser His Lys Phe Met Ser Thr Ser Val Gly
1               5                   10                  15

Asp Arg Ile Ser Ile Thr Cys Lys Ala Ser Gln Asp Val Asn Ile Ala
            20                  25                  30

Val Ala Trp Tyr Gln Gln Lys Pro Gly Gln Ser Pro Glu Val Leu Ile
        35                  40                  45

Tyr Ser Ala Ser Tyr Arg Phe Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr His Cys Gln Gln His Tyr Ser Ile Pro Tyr
                85                  90                  95

Thr Phe Gly Gly Gly Thr Lys Leu Glu Ile Lys
            100                 105
```

<210> SEQ ID NO 116
<211> LENGTH: 118
<212> TYPE: PRT
<213> ORGANISM: Artificial Sequence
<220> FEATURE:
<223> OTHER INFORMATION: Synthetic

<400> SEQUENCE: 116

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30
```

```
Gly Val His Trp Val Arg Gln Pro Pro Gly Lys Gly Leu Glu Trp Leu
        35                  40                  45

Gly Ala Ile Trp Ala Gly Gly Ser Ile Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Gly Pro Arg Tyr Asp Arg Ala Met Asp Tyr Trp Gly Gln Gly Thr
            100                 105                 110

Ser Val Thr Val Ser Ser
        115


<210> SEQ ID NO 117
<211> LENGTH: 108
<212> TYPE: PRT
<213> ORGANISM: Artificial Sequence
<220> FEATURE:
<223> OTHER INFORMATION: Synthetic

<400> SEQUENCE: 117

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Asn Ile Asn Ser Val Glu Ser
65                  70                  75                  80

Glu Asp Ile Ala Asp Tyr Tyr Cys Gln Gln Ser Asn Ser Trp Pro Thr
                85                  90                  95

Tyr Thr Phe Gly Gly Gly Thr Lys Leu Glu Ile Lys
            100                 105


<210> SEQ ID NO 118
<211> LENGTH: 119
<212> TYPE: PRT
<213> ORGANISM: Artificial Sequence
<220> FEATURE:
<223> OTHER INFORMATION: Synthetic

<400> SEQUENCE: 118

Glu Val Lys Leu Leu Glu Ser Gly Gly Gly Leu Val Gln Pro Glu Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Leu Asp Ser Ser Thr Ile Asn Tyr Ala Pro Ser Leu
    50                  55                  60

Glu Asp Lys Phe Ile Ile Ser Arg Asp Asn Ala Lys Ser Thr Leu Tyr
65                  70                  75                  80

Leu Gln Met Ser Lys Val Arg Ser Glu Asp Ser Ala Leu Tyr Tyr Cys
                85                  90                  95

Ala Arg Glu Phe Tyr Gly Gly Ser Tyr Leu Asp Tyr Trp Gly Gln Gly
```

```
            100                 105                 110

Thr Thr Leu Thr Val Ser Ser
        115


<210> SEQ ID NO 119
<211> LENGTH: 107
<212> TYPE: PRT
<213> ORGANISM: Artificial Sequence
<220> FEATURE:
<223> OTHER INFORMATION: Synthetic

<400> SEQUENCE: 119

Asp Ile Gln Met Thr Gln Ser Pro Ala Ser Leu Ser Val Ser Val Gly
1               5                   10                  15

Glu Thr Val Thr Ile Thr Cys Arg Ala Ser Asp Asn Ile Tyr Asn Asn
            20                  25                  30

Leu Ala Trp Tyr Gln Gln Lys Gln Gly Lys Ser Pro Gln Leu Leu Val
        35                  40                  45

Tyr Val Ala Thr Asn Leu Ala Asp Gly Val Pro Ser Arg Phe Ser Gly
    50                  55                  60

Ser Gly Ser Gly Thr Gln Tyr Ser Leu Lys Ile Asp Ser Leu Gln Ser
65                  70                  75                  80

Glu Asp Phe Gly Thr Tyr Tyr Cys Gln His Phe Trp Gly Thr Pro Trp
                85                  90                  95

Thr Phe Gly Gly Gly Thr Lys Leu Glu Ile Lys
            100                 105


<210> SEQ ID NO 120
<211> LENGTH: 117
<212> TYPE: PRT
<213> ORGANISM: Artificial Sequence
<220> FEATURE:
<223> OTHER INFORMATION: Synthetic

<400> SEQUENCE: 120

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ser Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Gly Trp Phe Ser Tyr Tyr Phe Asp Tyr Trp Gly Gln Gly Ser Thr
            100                 105                 110

Leu Thr Val Ser Ser
        115


<210> SEQ ID NO 121
<211> LENGTH: 107
<212> TYPE: PRT
<213> ORGANISM: Artificial Sequence
<220> FEATURE:
<223> OTHER INFORMATION: Synthetic

<400> SEQUENCE: 121
```

```
Asp Met Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Asn Val Trp
                85                  90                  95

Thr Phe Gly Gly Gly Thr Lys Leu Glu Ile Lys
            100                 105


<210> SEQ ID NO 122
<211> LENGTH: 120
<212> TYPE: PRT
<213> ORGANISM: Artificial Sequence
<220> FEATURE:
<223> OTHER INFORMATION: Synthetic

<400> SEQUENCE: 122

Gln Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Ser Ser Tyr
            20                  25                  30

Ser Val His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Asn Phe
    50                  55                  60

Lys Ala Lys Ala Thr Leu Thr Ala Asp Glu Ser Ser Ser Thr Ala Tyr
65                  70                  75                  80

Met Gln Leu Arg Ser Leu Thr Ser Glu Asp Ser Ala Val Tyr Phe Cys
                85                  90                  95

Ala Arg Asp Gly Tyr Pro Tyr Tyr Tyr Ala Leu Asp Tyr Trp Gly Gln
            100                 105                 110

Gly Thr Ser Val Thr Val Ser Ser
        115                 120


<210> SEQ ID NO 123
<211> LENGTH: 107
<212> TYPE: PRT
<213> ORGANISM: Artificial Sequence
<220> FEATURE:
<223> OTHER INFORMATION: Synthetic

<400> SEQUENCE: 123

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Pro Leu Ile
        35                  40                  45

Tyr Ser Ala Ser Tyr Arg Tyr Ser Gly Val Pro Asp Arg Phe Thr Gly
    50                  55                  60

Gly Gly Ser Gly Thr Asp Phe Thr Leu Thr Ile Ser Asn Val Gln Ser
```

```
65                  70                  75                  80

Glu Asp Leu Ala Glu Tyr Phe Cys Gln Gln Tyr His Arg Tyr Pro Trp
                85                  90                  95

Thr Phe Gly Gly Gly Thr Lys Leu Glu Ile Lys
            100                 105


<210> SEQ ID NO 124
<211> LENGTH: 121
<212> TYPE: PRT
<213> ORGANISM: Artificial Sequence
<220> FEATURE:
<223> OTHER INFORMATION: Synthetic

<400> SEQUENCE: 124

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Ser Tyr
            20                  25                  30

Asp Ile Ser Trp Val Lys Gln Arg Pro Gly Gln Gly Leu Glu Trp Ile
        35                  40                  45

Gly Trp Ile Tyr Pro Gly Asp Gly Ser Thr Glu Tyr Asn Glu Lys Phe
    50                  55                  60

Lys Ala Lys Ala Thr Leu Thr Ala Asp Lys Ser Ser Ser Thr Ala Tyr
65                  70                  75                  80

Met Gln Leu Ser Ser Leu Thr Ser Glu Asn Ser Ala Val Tyr Phe Cys
                85                  90                  95

Ala Arg Arg Ala Thr Thr Pro Thr Gly Tyr Ala Leu Asp Tyr Trp Gly
            100                 105                 110

Gln Gly Thr Ser Val Thr Val Ser Ser
        115                 120


<210> SEQ ID NO 125
<211> LENGTH: 107
<212> TYPE: PRT
<213> ORGANISM: Artificial Sequence
<220> FEATURE:
<223> OTHER INFORMATION: Synthetic

<400> SEQUENCE: 125

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys His Gly Lys Ser Pro Gln Leu Leu Val
        35                  40                  45

Tyr Gly Ala Ile Asn Leu Ala Asp Gly Val Pro Ser Arg Phe Thr Gly
    50                  55                  60

Ser Gly Ser Asp Thr Gln Tyr Ser Leu Lys Ile Asn Ser Leu Gln Ser
65                  70                  75                  80

Glu Asp Phe Gly Asn Tyr Tyr Cys Gln His Phe Trp Asp Ile Pro Trp
                85                  90                  95

Thr Phe Gly Gly Gly Thr Lys Leu Glu Ser Lys
            100                 105


<210> SEQ ID NO 126
<211> LENGTH: 8
<212> TYPE: PRT
<213> ORGANISM: Artificial Sequence
<220> FEATURE:
```

<223> OTHER INFORMATION: Synthetic

<400> SEQUENCE: 126

Gly Phe Asn Ile Lys Asp Thr Tyr
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic

<400> SEQUENCE: 127

Gly Phe Ser Leu Thr Ser Tyr Gly
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic

<400> SEQUENCE: 128

Gly Phe Ser Leu Ile Ser Tyr Gly
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic

<400> SEQUENCE: 129

Gly Tyr Ser Ile Thr Ser Asp Tyr Ala
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic

<400> SEQUENCE: 130

Gly Tyr Ser Phe Thr Gly Tyr Phe
1               5

<210> SEQ ID NO 131
<211> LENGTH: 10
<212> TYPE: PRT
<213> ORGANISM: Artificial Sequence
<220> FEATURE:
<223> OTHER INFORMATION: Synthetic

<400> SEQUENCE: 131

Gly Phe Ser Leu Ser Thr Ser Gly Met Gly
1               5                   10

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Tyr Ser Phe Thr Ser Tyr Trp
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic

<400> SEQUENCE: 133

Gly Tyr Ala Phe Thr Ser Tyr Trp
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Asp Pro Ala Ser Gly Lys Thr
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic

<400> SEQUENCE: 135

Ile Trp Ser Gly Gly Ser Thr
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic

<400> SEQUENCE: 136

Ile Trp Ala Gly Gly Ser Thr
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic

<400> SEQUENCE: 137

Ile Ser Tyr Ser Gly Thr Thr
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic

<400> SEQUENCE: 138

Ile Asp Pro Ala Asn Gly Asn Ser
1               5

<210> SEQ ID NO 139
<211> LENGTH: 8
<212> TYPE: PRT
<213> ORGANISM: Artificial Sequence
<220> FEATURE:
<223> OTHER INFORMATION: Synthetic

<400> SEQUENCE: 139

Ile Asn Pro Tyr Asn Gly Asp Thr
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic

<400> SEQUENCE: 140

Ile Asp Pro Ala Asn Gly Asp Thr
1               5

<210> SEQ ID NO 141
<211> LENGTH: 8
<212> TYPE: PRT
<213> ORGANISM: Artificial Sequence
<220> FEATURE:
<223> OTHER INFORMATION: Synthetic

<400> SEQUENCE: 141

Ile Asp Pro Ala Asn Gly Asn Thr
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic

<400> SEQUENCE: 142

Ile Tyr Trp Asp Asp Asp Lys
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic

<400> SEQUENCE: 143

Ile His Pro Ser Asp Ser Glu Thr
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic

<400> SEQUENCE: 144

Ile Tyr Pro Gly Asp Gly Ala Thr
1               5

<210> SEQ ID NO 145
<211> LENGTH: 8
<212> TYPE: PRT
<213> ORGANISM: Artificial Sequence
<220> FEATURE:
<223> OTHER INFORMATION: Synthetic

<400> SEQUENCE: 145

Ile Asp Pro Ala Ser Gly Asn Thr
1               5

<210> SEQ ID NO 146
<211> LENGTH: 14
<212> TYPE: PRT
<213> ORGANISM: Artificial Sequence
<220> FEATURE:
<223> OTHER INFORMATION: Synthetic

<400> SEQUENCE: 146

Cys Ala Ser Gly Tyr Asp Val Asn Tyr Glu Leu Asp Tyr Trp
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Synthetic

<400> SEQUENCE: 147

Cys Ala Lys Tyr Arg Tyr Asp Ser Phe Ala Tyr Trp
1               5                   10

<210> SEQ ID NO 148
<211> LENGTH: 13
<212> TYPE: PRT
<213> ORGANISM: Artificial Sequence
<220> FEATURE:
<223> OTHER INFORMATION: Synthetic

<400> SEQUENCE: 148

Cys Gly Arg Asp Tyr Gly Ile Leu Leu Ile Asp Tyr Trp
1               5                   10

<210> SEQ ID NO 149
<211> LENGTH: 17
<212> TYPE: PRT
<213> ORGANISM: Artificial Sequence
<220> FEATURE:
<223> OTHER INFORMATION: Synthetic

<400> SEQUENCE: 149

Cys Ala Gly Arg Arg Gly Ala Tyr Tyr Gly Asn Tyr Glu Glu Asp Tyr
1               5                   10                  15

Trp

<210> SEQ ID NO 150
<211> LENGTH: 17
<212> TYPE: PRT
<213> ORGANISM: Artificial Sequence
<220> FEATURE:
<223> OTHER INFORMATION: Synthetic

<400> SEQUENCE: 150

Cys Ala Arg Ser Tyr Tyr Asp Tyr Asp Gly Gly Gly Cys Phe Asp Tyr
1 5 10 15

Trp

<210> SEQ ID NO 151
<211> LENGTH: 7
<212> TYPE: PRT
<213> ORGANISM: Artificial Sequence
<220> FEATURE:
<223> OTHER INFORMATION: Synthetic

<400> SEQUENCE: 151

Cys Gly Leu Arg Thr Tyr Trp
1 5

<210> SEQ ID NO 152
<211> LENGTH: 16
<212> TYPE: PRT
<213> ORGANISM: Artificial Sequence
<220> FEATURE:
<223> OTHER INFORMATION: Synthetic

<400> SEQUENCE: 152

Cys Ala Arg Ser Tyr Tyr Tyr Gly Thr Thr Ser Trp Phe Ala Ser Trp
1 5 10 15

<210> SEQ ID NO 153
<211> LENGTH: 17
<212> TYPE: PRT
<213> ORGANISM: Artificial Sequence
<220> FEATURE:
<223> OTHER INFORMATION: Synthetic

<400> SEQUENCE: 153

Cys Ala Arg Trp Asp Phe Gly Asn Tyr Val Asp Tyr Ala Met Asp Tyr
1 5 10 15

Trp

<210> SEQ ID NO 154
<211> LENGTH: 17
<212> TYPE: PRT
<213> ORGANISM: Artificial Sequence
<220> FEATURE:
<223> OTHER INFORMATION: Synthetic

<400> SEQUENCE: 154

Cys Ala Arg Arg Gly Pro Leu Ile Thr Thr Asp Gly Thr Phe Asp Val
1 5 10 15

Trp

<210> SEQ ID NO 155
<211> LENGTH: 17
<212> TYPE: PRT
<213> ORGANISM: Artificial Sequence
<220> FEATURE:
<223> OTHER INFORMATION: Synthetic

<400> SEQUENCE: 155

Cys Gly Arg Gly Leu Tyr Gly Lys Gly Tyr Tyr Tyr Ala Met Asp Tyr
1 5 10 15

Trp

<210> SEQ ID NO 156
<211> LENGTH: 14
<212> TYPE: PRT
<213> ORGANISM: Artificial Sequence
<220> FEATURE:
<223> OTHER INFORMATION: Synthetic

<400> SEQUENCE: 156

Cys Ala Arg Ser Ser Gly Tyr Asp Trp Tyr Phe Asp Val Trp
1 5 10

<210> SEQ ID NO 157
<211> LENGTH: 14
<212> TYPE: PRT
<213> ORGANISM: Artificial Sequence
<220> FEATURE:
<223> OTHER INFORMATION: Synthetic

<400> SEQUENCE: 157

Cys Ala Arg Ser Gly Gly Tyr Asp Trp Tyr Phe Asp Val Trp
1 5 10

<210> SEQ ID NO 158
<211> LENGTH: 15
<212> TYPE: PRT
<213> ORGANISM: Artificial Sequence
<220> FEATURE:
<223> OTHER INFORMATION: Synthetic

<400> SEQUENCE: 158

Cys Thr Arg Tyr Tyr Tyr Gly Ser Ser Gly Phe Phe Asp Val Trp
1 5 10 15

<210> SEQ ID NO 159
<211> LENGTH: 15
<212> TYPE: PRT
<213> ORGANISM: Artificial Sequence
<220> FEATURE:
<223> OTHER INFORMATION: Synthetic

<400> SEQUENCE: 159

Cys Ala Arg Ser Tyr Tyr Thr Tyr Asp Gly Phe Phe Asp Val Trp
1 5 10 15

<210> SEQ ID NO 160
<211> LENGTH: 17
<212> TYPE: PRT
<213> ORGANISM: Artificial Sequence
<220> FEATURE:
<223> OTHER INFORMATION: Synthetic

<400> SEQUENCE: 160

Cys Ala Arg Thr Tyr Tyr Tyr Gly Ser Ser Tyr Glu Ala Met Asp Tyr
1 5 10 15

Trp

<210> SEQ ID NO 161
<211> LENGTH: 6
<212> TYPE: PRT
<213> ORGANISM: Artificial Sequence
<220> FEATURE:
<223> OTHER INFORMATION: Synthetic

<400> SEQUENCE: 161

Gln Asn Ile Asn Val Trp
1 5

<210> SEQ ID NO 162
<211> LENGTH: 10
<212> TYPE: PRT
<213> ORGANISM: Artificial Sequence
<220> FEATURE:
<223> OTHER INFORMATION: Synthetic

<400> SEQUENCE: 162

Lys Ser Val Ser Thr Ser Gly Tyr Ser Tyr
1 5 10

<210> SEQ ID NO 163
<211> LENGTH: 5
<212> TYPE: PRT
<213> ORGANISM: Artificial Sequence
<220> FEATURE:
<223> OTHER INFORMATION: Synthetic

<400> SEQUENCE: 163

Ser Ser Val Ser Tyr
1 5

<210> SEQ ID NO 164
<211> LENGTH: 5
<212> TYPE: PRT
<213> ORGANISM: Artificial Sequence
<220> FEATURE:
<223> OTHER INFORMATION: Synthetic

<400> SEQUENCE: 164

Ser Ile Val Asn Tyr
1 5

<210> SEQ ID NO 165
<211> LENGTH: 6
<212> TYPE: PRT
<213> ORGANISM: Artificial Sequence
<220> FEATURE:
<223> OTHER INFORMATION: Synthetic

<400> SEQUENCE: 165

Gln Ser Val Ser Asn Asp
1 5

<210> SEQ ID NO 166
<211> LENGTH: 6
<212> TYPE: PRT
<213> ORGANISM: Artificial Sequence
<220> FEATURE:
<223> OTHER INFORMATION: Synthetic

<400> SEQUENCE: 166

Gln Asp Ile Asn Asn Asn
1 5

<210> SEQ ID NO 167
<211> LENGTH: 6
<212> TYPE: PRT
<213> ORGANISM: Artificial Sequence
<220> FEATURE:
<223> OTHER INFORMATION: Synthetic

<400> SEQUENCE: 167

Glu Asp Ile Tyr Asn His
1 5

<210> SEQ ID NO 168
<211> LENGTH: 6
<212> TYPE: PRT
<213> ORGANISM: Artificial Sequence
<220> FEATURE:
<223> OTHER INFORMATION: Synthetic

<400> SEQUENCE: 168

Gln Asp Leu Tyr Ser Phe
1 5

<210> SEQ ID NO 169
<211> LENGTH: 6
<212> TYPE: PRT
<213> ORGANISM: Artificial Sequence
<220> FEATURE:
<223> OTHER INFORMATION: Synthetic

<400> SEQUENCE: 169

Gln Asp Val Gly Thr Ser
1 5

<210> SEQ ID NO 170
<211> LENGTH: 6
<212> TYPE: PRT
<213> ORGANISM: Artificial Sequence
<220> FEATURE:
<223> OTHER INFORMATION: Synthetic

<400> SEQUENCE: 170

Gln Asp Val Asp Thr Ala
1 5

<210> SEQ ID NO 171
<211> LENGTH: 12
<212> TYPE: PRT
<213> ORGANISM: Artificial Sequence
<220> FEATURE:
<223> OTHER INFORMATION: Synthetic

<400> SEQUENCE: 171

Gln Ser Leu Leu Tyr Ser Ser Asn Gln Lys Asn Tyr
1 5 10

<210> SEQ ID NO 172
<211> LENGTH: 10
<212> TYPE: PRT
<213> ORGANISM: Artificial Sequence
<220> FEATURE:
<223> OTHER INFORMATION: Synthetic

<400> SEQUENCE: 172

Glu Ser Val Asp Ser Tyr Gly Asn Ser Phe
1 5 10

<210> SEQ ID NO 173
<211> LENGTH: 10
<212> TYPE: PRT
<213> ORGANISM: Artificial Sequence
<220> FEATURE:
<223> OTHER INFORMATION: Synthetic

<400> SEQUENCE: 173

Glu Thr Val Asp Ser Tyr Gly Asn Ser Phe
1 5 10

<210> SEQ ID NO 174

<211> LENGTH: 11
<212> TYPE: PRT
<213> ORGANISM: Artificial Sequence
<220> FEATURE:
<223> OTHER INFORMATION: Synthetic

<400> SEQUENCE: 174

Cys Gln Gln Gly Gln Ser Tyr Pro Tyr Thr Phe
1 5 10

<210> SEQ ID NO 175
<211> LENGTH: 11
<212> TYPE: PRT
<213> ORGANISM: Artificial Sequence
<220> FEATURE:
<223> OTHER INFORMATION: Synthetic

<400> SEQUENCE: 175

Cys Gln His Ser Arg Glu Leu Pro Tyr Thr Phe
1 5 10

<210> SEQ ID NO 176
<211> LENGTH: 11
<212> TYPE: PRT
<213> ORGANISM: Artificial Sequence
<220> FEATURE:
<223> OTHER INFORMATION: Synthetic

<400> SEQUENCE: 176

Cys Phe Gln Gly Ser Gly Tyr Pro Phe Thr Phe
1 5 10

<210> SEQ ID NO 177
<211> LENGTH: 11
<212> TYPE: PRT
<213> ORGANISM: Artificial Sequence
<220> FEATURE:
<223> OTHER INFORMATION: Synthetic

<400> SEQUENCE: 177

Cys Gln Gln Trp Ser Ser Tyr Pro Tyr Thr Phe
1 5 10

<210> SEQ ID NO 178
<211> LENGTH: 11
<212> TYPE: PRT
<213> ORGANISM: Artificial Sequence
<220> FEATURE:
<223> OTHER INFORMATION: Synthetic

<400> SEQUENCE: 178

Cys Gln Gln Gly Tyr Ser Ser Pro Leu Thr Phe
1 5 10

<210> SEQ ID NO 179
<211> LENGTH: 11
<212> TYPE: PRT
<213> ORGANISM: Artificial Sequence
<220> FEATURE:
<223> OTHER INFORMATION: Synthetic

<400> SEQUENCE: 179

Cys Val Gln Ser Val Gln Phe Pro Tyr Thr Phe
1 5 10

<210> SEQ ID NO 180
<211> LENGTH: 11

```
<212> TYPE: PRT
<213> ORGANISM: Artificial Sequence
<220> FEATURE:
<223> OTHER INFORMATION: Synthetic

<400> SEQUENCE: 180

Cys Gln Gln Tyr Trp Ser Thr Pro Tyr Thr Phe
1               5                   10


<210> SEQ ID NO 181
<211> LENGTH: 11
<212> TYPE: PRT
<213> ORGANISM: Artificial Sequence
<220> FEATURE:
<223> OTHER INFORMATION: Synthetic

<400> SEQUENCE: 181

Cys Leu Gln Tyr Asp Ala Phe Pro Trp Thr Phe
1               5                   10


<210> SEQ ID NO 182
<211> LENGTH: 11
<212> TYPE: PRT
<213> ORGANISM: Artificial Sequence
<220> FEATURE:
<223> OTHER INFORMATION: Synthetic

<400> SEQUENCE: 182

Cys Gln Gln Tyr Ser Ser Tyr Pro Tyr Thr Phe
1               5                   10


<210> SEQ ID NO 183
<211> LENGTH: 11
<212> TYPE: PRT
<213> ORGANISM: Artificial Sequence
<220> FEATURE:
<223> OTHER INFORMATION: Synthetic

<400> SEQUENCE: 183

Cys Gln Gln Tyr Tyr Ser Tyr Pro Trp Thr Phe
1               5                   10


<210> SEQ ID NO 184
<211> LENGTH: 11
<212> TYPE: PRT
<213> ORGANISM: Artificial Sequence
<220> FEATURE:
<223> OTHER INFORMATION: Synthetic

<400> SEQUENCE: 184

Cys Gln Gln Ser Asn Glu Asp Pro Trp Thr Phe
1               5                   10


<210> SEQ ID NO 185
<211> LENGTH: 10
<212> TYPE: PRT
<213> ORGANISM: Artificial Sequence
<220> FEATURE:
<223> OTHER INFORMATION: Synthetic

<400> SEQUENCE: 185

Cys Gln Gln Asp Tyr Ser Ser Pro Thr Phe
1               5                   10


<210> SEQ ID NO 186
<211> LENGTH: 11
<212> TYPE: PRT
```

-continued

```
<213> ORGANISM: Artificial Sequence
<220> FEATURE:
<223> OTHER INFORMATION: Synthetic

<400> SEQUENCE: 186

Cys Gln Gln Asp Tyr Ser Ser Pro Pro Thr Phe
1               5                   10
```

COMPOSITIONS AND METHODS FOR THE DETECTION AND TREATMENT OF SARS-CoV-2 VIRUS INFECTION

CROSS-REFERENCE TO RELATED APPLICATIONS

The present invention is filed under 35 U.S.C. § 371 as the U.S. national phase of International Application No. PCT/US2021/040836, filed Jul. 8, 2021, which designated the U.S. and claims the right of priority of U.S. Provisional Application No. 63/049,409, filed Jul. 8, 2020, and to U.S. Provisional Application No. 63/183,955, filed May 4, 2021. The entire disclosures of the above-identified priority applications are hereby fully incorporated herein by reference.

STATEMENT REGARDING FEDERALLY SPONSORED RESEARCH OR DEVELOPMENT

This invention was made with government support under Award No. 75D30119P05589 from the Centers for Disease Control and Prevention. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 6, 2023, is named 064489-070_SeqListing.txt and is 144 kilobytes in size.

FIELD OF THE INVENTION

The invention is generally directed to compositions and methods of use thereof for the diagnosis, detection, and treatment of SARS-CoV-2 infections.

BACKGROUND OF THE INVENTION

The novel coronavirus, SARS-CoV-2, has caused a global pandemic of COVID-19 respiratory disease, with millions infected, hundreds of thousands of deaths, and many survivors dealing with multiple long-term adverse health effects.

Coronaviruses, including SARS-CoV-2 and two other zoonotic infections to have recently appeared called severe acute respiratory syndrome-1 (SARS-1) and Middle East Respiratory Syndrome (MERS). These viruses are spherical, enveloped, RNA viruses displaying prominent glycosylated spikes known as the ectodomain and are composed of two subunits (S1 and S2). The S1 subunit contains the key receptor binding domain (RBD), responsible for binding to the human angiotensin converting enzyme 2 (ACE2) receptor that mediates viral entry. The ectodomain is a trimeric assembly in which part of the S1 subunit can adopt two different conformations, "up" and "down," thought to be important in ACE2 recognition.

Because of its key role in viral infectivity, the RBD is a logical target for antibody development. Antibodies to the SARS-CoV-1 RBD were found to strongly inhibit viral infection (thereby designated as neutralizing), and some antibodies have been reported against SARS-CoV-2 with the same or similar properties. However, it has also been observed that other antibodies enhance ACE2 binding and thus speed viral uptake by cells, presumably by binding in such a way as to increase binding affinity with the receptor either directly or allosterically. The critical nature of this interaction has been further highlighted by the dominance of the D614G mutation, which strongly stabilizes the RBD-ACE2 interaction.

Furthermore, epidemiological control of virus spread among the human population requires fast and accurate testing. Current genome-detecting assays based on reverse transcription polymerase chain reaction (RT-PCR) are relatively expensive and can only be made fast using expensive and technically demanding equipment. Direct detection and quantification of viral particles in patient and environmental samples with sensitivity to rival that of RT-PCR would represent a breakthrough in the ability to identify and help those infected. Such detection requires, first and foremost, a molecule capable of binding selectively and tightly to the virus.

SUMMARY

Compositions that selectively bind to coronaviruses, including but not limited to SARS-COV-2 and methods of use thereof are provided. One embodiment provides a panel of 37 antibodies and antigen-binding fragments thereof that were developed against SARS-CoV-2, as derived from these sequences [including F(ab), F(ab')$_2$, single-chain variable (scF$_v$) fragments, and others]. The disclosed compositions are useful in diagnostic and therapeutic applications.

One embodiment is based in part on a variety of antibodies to SARS-CoV-2 spike protein (S protein) and their use in the detection, diagnosis, and treatment during active COVID-19 infection. Another embodiment provides monoclonal antibodies (mAbs) from BALB/c mice immunized with mammalian recombinant S1, mFc-RBD, and mFc-RBD displayed on virus-like particles. Characterization of the antibodies using multiple methods (ELISA, bio-layer interferometry (BLI), split-GFP assay for receptor binding, and immunofluorescence) with active virus and tissue from infected patients revealed some of the mAbs of this disclosure to be SARS-CoV-2-specific and others to be strongly reactive with both SARS-CoV-1 and SARS-CoV-2. Immunoassays were developed using optimal mAb pairings with high sensitivity for spike protein, viral culture supernatant, and infected tissue samples. Thus, the mAbs of this disclosure are capable of recognizing spike protein in a variety of environments with potential uses in immunoassay development and as immunodiagnostic reagents for clinical sample and tissue confirmation of SASRS-CoV-2.

Still another embodiment provides an antibody or antigen-binding fragments thereof that bind, preferably specifically, to a SARS-CoV-2 spike protein. Optionally, the antibody is a monoclonal antibody, antibody fragment, chimeric antibody, humanized antibody, single-chain antibody or antibody that competitively inhibits the binding of an anti-SARS-CoV protein antibody or antigen-binding fragment thereof to its respective antigenic epitope. In one embodiment, the disclosed antibodies can optionally be produced in Chinese hamster ovary (CHO) cells or in bacterial cells and preferably inhibit, reduce or prevent the binding of coronaviruses, including but not limited to SARS-CoV-2 spike protein to cell surface proteins in a subject. In some embodiments, the disclosed antibodies and antigen-binding fragments thereof reduce or inhibit the growth or proliferation of or induce the death of a cell infected with a coronavirus to which they bind.

In another embodiment, the disclosed antibodies and antigen-binding fragments thereof are detectably labeled, attached to a solid support, or the like, such as a lateral flow assay device which provides for point-of-care detection of SARS-CoV-2 and/or diagnosis.

Yet another embodiment provides vectors comprising nucleic acids, including but not limited to DNA, encoding any of the herein described antibodies and antigen-binding fragments thereof. Host cells comprising any such vector are also provided. By way of example, the host cells may be CHO cells, bacterial cells (such as *E. coli*) used for recombinant protein expression, or yeast cells. A process for producing any of the herein described antibodies is further provided and comprises culturing host cells under conditions suitable for expression of the desired antibody and recovering the desired antibody from the cell culture.

One embodiment provides a composition, for example a pharmaceutical composition, including an anti-SARS-CoV-2 antibody or antigen-binding fragment thereof, in combination with a carrier. Optionally, the carrier is a pharmaceutically acceptable carrier. Another embodiment provides an article of manufacture including a container and a composition contained within the container, wherein the composition of matter comprises an anti-SARS-CoV-2 antibody or antigen-binding fragment thereof as described herein. The article may optionally include a label affixed to the container, or a package insert included with the container, that refers to the use of the composition for the therapeutic treatment or diagnostic detection of a SARS-CoV-2 infection.

Still another embodiment provides the use of an anti-SARS-CoV-2 polypeptide antibody or antigen-fragment thereof as described herein, for the preparation of a medicament useful in the treatment of a condition which is responsive to the anti-SARS-CoV-2 protein antibody.

Yet another embodiment provides any isolated antibody having one or more of the complementarity determining regions (CDRs), including a CDR-kappa1, CDR-kappa2, CDR-kappa3, CDR-H1, CDR-H2, or CDR-H3 sequence disclosed herein.

Another embodiment provides a method of therapeutically treating a mammal having a SARS-CoV-2 infection by administering to the mammal a therapeutically effective amount of an antibody that binds to the SARS-CoV-2 spike protein, thereby resulting in the effective therapeutic treatment of the infection in the mammal. In these therapeutic methods, the antibody may be a monoclonal antibody, antibody fragment, chimeric antibody, humanized antibody, or single-chain antibody. Antibodies employed in these methods may optionally be conjugated to a growth inhibitory agent or cytotoxic agent such as a toxin.

Another embodiment provides a method of determining the presence of a SARS-CoV-2 spike protein in a sample suspected of containing the SARS-CoV-2 spike protein, by exposing the sample to an antibody that binds to the SARS-CoV-2 spike protein and determining binding of the antibody to the SARS-CoV-2 spike protein in the sample, wherein the presence of such binding is indicative of the presence of the SARS-CoV-2 spike protein in the sample. Optionally, the sample may contain cells (which may be fibroblasts, epithelial cells, mucosal cells, and the like) suspected of expressing the SARS-CoV-2 spike protein. The antibody employed in these methods may optionally be detectably labeled, attached to a solid support, or the like.

This disclosure is further directed to mAbs and related binding proteins that bind specifically to the spike protein of the SARS-CoV-2 virus and to the use of those mAbs and related binding proteins in epitope blocking ELISAs. Thus, one embodiment provides methods for detecting SARS-CoV-2 virus spike protein in a biological sample by contacting the sample with an antigen which contains an epitope of a spike protein and determining whether an antibody in the sample binds to the epitope. Preferably the binding determination is made in an epitope blocking ELISA. These methods thereby provide highly sensitive and specific epitope blocking ELISAs (EB ELISA) for detecting SARS-CoV-2 spike subtypes.

A further embodiment provides a method of diagnosing the presence of a SARS-CoV-2 infection in a mammal, by detecting the level of expression of a gene encoding a SARS-CoV-2 spike protein in a test sample of tissue cells obtained from the mammal, wherein detection of expression of the SARS-CoV-2 spike protein in the test sample is indicative of the presence of SARS-CoV-2 infection in the mammal from which the test sample was obtained.

Another embodiment provides a method of diagnosing the presence of a SARS-CoV-2 infection in a mammal, by contacting a test sample comprising tissue cells obtained from the mammal with an antibody that binds to a SARS-CoV-2 spike protein and detecting the formation of a complex between the antibody and the SARS-CoV-2 spike protein in the test sample, wherein the formation of a complex is indicative of the presence of a SARS-CoV-2 infection in the mammal. Optionally, the antibody employed is detectably labeled, attached to a solid support, or the like. In these methods, the test sample of tissue cells may be obtained from an individual suspected of having a viral infection.

Another embodiment provides a method of binding an antibody to a cell that expresses a SARS-CoV-2 spike protein, by contacting a cell that expresses a SARS-CoV-2 spike protein with the antibody of this disclosure under conditions which are suitable for binding of the antibody to the SARS-CoV-2 spike protein and allowing binding therebetween. In preferred embodiments, the antibody is labeled with a molecule or compound that is useful for qualitatively and/or quantitatively determining the location and/or amount of binding of the antibody to the cell.

Other embodiments of this disclosure include the use of a SARS-CoV-2 spike protein, a nucleic acid encoding a SARS-CoV-2 spike protein, or a vector or host cell comprising that nucleic acid, or an anti-SARS-CoV-2 spike protein antibody in the preparation of a medicament useful for (i) the therapeutic treatment or diagnostic detection of a SARS-CoV-2 infection, or (ii) the therapeutic treatment or prevention of a SARS-CoV-2 infection-related disorder.

Another embodiment provides a method for inhibiting the production of additional viral particles in a SARS-CoV-2-infected cell, wherein the growth of the SARS-CoV-2 infected cell is at least in part dependent upon the expression of a SARS-CoV-2 spike protein (wherein the SARS-CoV-2 spike protein may be expressed either within the infected cell itself or a cell that produces polypeptide(s) that have a growth potentiating effect on the infected cells), by contacting the SARS-CoV-2 spike protein with an antibody that binds to the SARS-CoV-2 spike protein, thereby antagonizing the growth-potentiating activity of the SARS-CoV-2 spike protein and, in turn, inhibiting the growth of the infected cell. Preferably the growth of the infected cell is completely inhibited. More preferably, binding of the antibody to the SARS-CoV-2 spike protein induces the death of the infected cell. Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells or bacterial cells.

Yet another embodiment provides a method of therapeutically treating a viral infection in a mammal, wherein the infection is at least in part dependent upon the expression of a SARS-CoV-2 spike protein, by administering to the mammal a therapeutically effective amount of an antibody or antigen-binding fragment thereof that binds to the SARS-CoV-2 spike protein, thereby antagonizing the activity of the SARS-CoV-2 spike protein and resulting in the effective therapeutic treatment of the infection in the mammal. Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells or bacterial cells.

One embodiment provides a bispecific antibody that binds to SARS-CoV-2 spike protein and a cell-surface protein of an immune cell. The immune cell can be a T cell, for example a cytotoxic T cell, a macrophage, a dendritic cell, or a neutrophil.

Further embodiments of the present invention will be evident to the skilled artisan upon a reading of the present specification.

BRIEF DESCRIPTION OF THE DRAWINGS

FIGS. 3A-3B are graphs showing single-concentration (FIG. 3A) and representative (mAb 3G7) dose-dependent (FIG. 3B) antibody-mediated inhibition or enhancement of ecto-Spike binding to human ACE2 receptor as measured by BLI. FIG. 3C is a histogram showing in vitro neutralization of SARS-CoV-2 virus by mAbs. FIG. 3D is a histogram showing binding of antibodies to biotinylated peptide (amino acids 486-501) plated on streptavidin-coated plates as measured by ELISA. Dashed line represents absorbance of negative control wells. FIG. 3E is a representative immunochemistry image showing mAb staining of SARS-CoV-2 in infected COVID-19 patient lung tissue by IHC (antigen retrieval method) (mAb 3D5, 1:25 dilution, 40× magnification).

FIG. 4 is a chart showing epitope binding patterns of a subset of selected antibodies. Values represent signals from biolayer interferometry (BLI) in which two antibodies (or the same antibody twice) is added to the instrument probe functionalized with immobilized spike ectodomain. The reported value represents the observed signal after the second antibody is added (arbitrary units). Thus, if the first antibody occupies the same binding sites as the second, little to no increase in signal is observed after the second addition. Asterisks mark the antibodies identified as superior neutralizers in FIG. 3C.

DETAILED DESCRIPTION OF THE INVENTION

I. Definitions

Figure 1A:
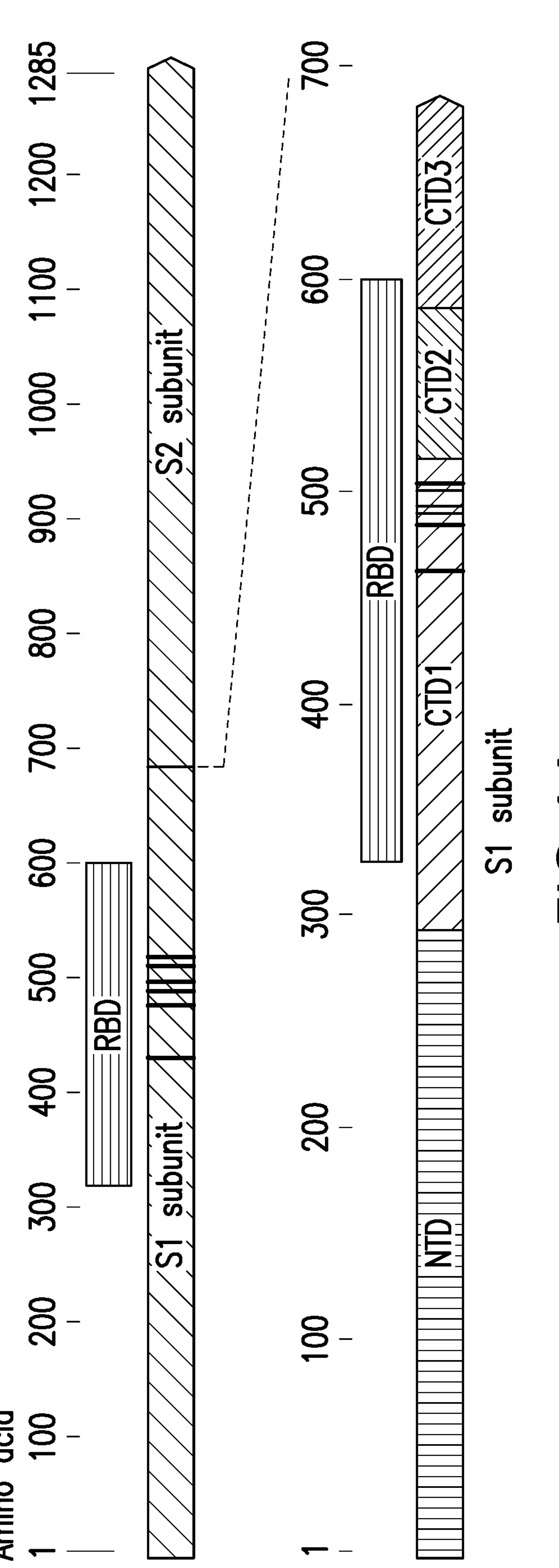
FIG. 1A is a diagram showing recombinant spike subunit 1 protein (His-S1, residues 1-701) or S1 Receptor Binding Domain (mouse FcS1-RBD, residues 391-600, PDBID: 6vxx) antigens.
Figure 1A:
Figures 1B, 1C:
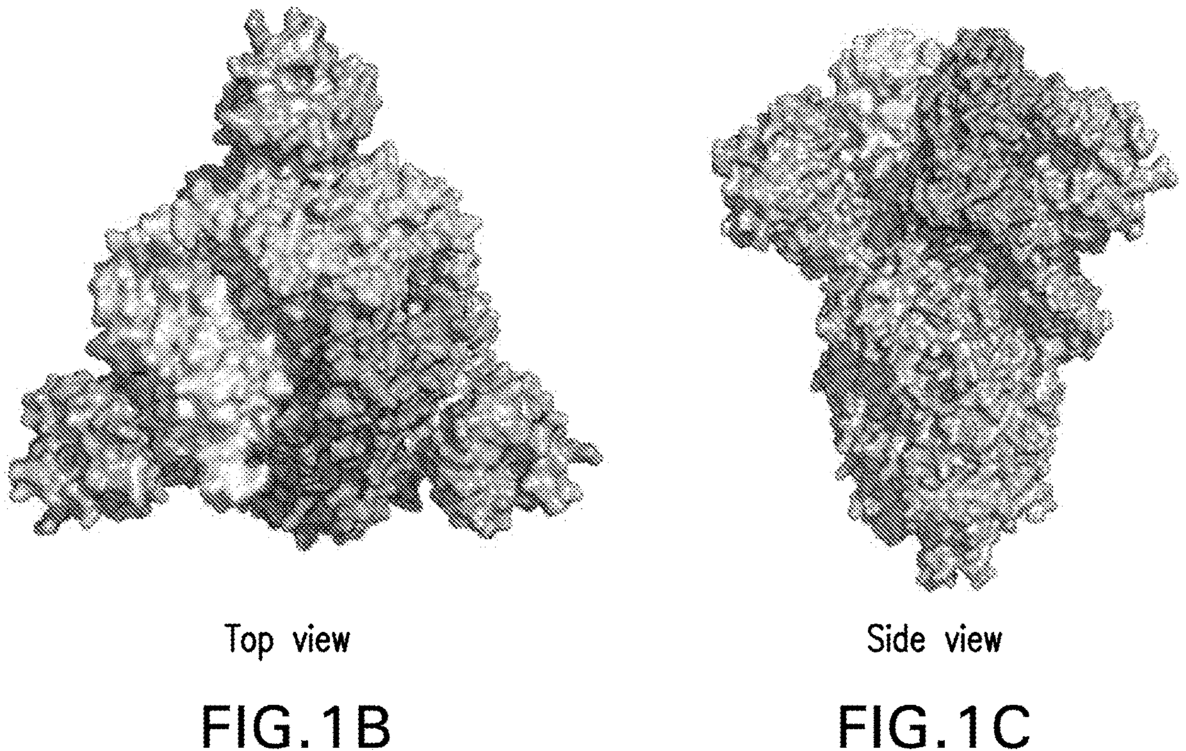
FIGS. 1B-1C are structural models of recombinant spike protein.

As used herein, a molecule is said to be able to "immunospecifically bind" a second molecule if such binding exhibits the specificity and affinity of an antibody to its cognate antigen. Antibodies are said to be capable of immunospecifically binding to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. In some embodiments, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, a molecule is said to "physiospecifically bind" a second molecule if such binding exhibits the specificity and affinity of a receptor to its cognate binding ligand. A molecule can be capable of physiospecifically binding to more than one other molecule.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, MD (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site and exhibit an ability to immunospecifically bind antigen. Such fragments include Fab', $F(ab')_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor, or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

As used herein the term "modulate" relates to a capacity to alter an effect, result, or activity (e.g., signal transduction). Such modulation can be agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. In some embodiments, such modulation will provide at least a 10% change in a measurable immune system activity, at least a 50% change in such activity, or at least a 2-fold, 5-fold, 10-fold, or at least a 100-fold change in such activity.

The term "substantially," as used in the context of binding or exhibited effect, is intended to denote that the observed effect is physiologically or therapeutically relevant. Thus, for example, a molecule can substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the "activating" or "stimulatory" signals encompass signals that result in enhancing an activity or enhancing signal transduction.

As used herein, "suppressive" signals refer to signals that suppress immune activity.

The term "derivative" refers to an antibody or antigen-binding fragment thereof that immunospecifically binds to the same target of a parent or reference antibody, but which differs in amino acid sequence from the parent or reference antibody or antigen binding fragment thereof by including one, two, three, four, five or more amino acid substitutions, additions, deletions or modifications relative to the parent or reference antibody or antigen binding fragment thereof. In some embodiments, such derivatives will have substantially the same immunospecificity and/or characteristics, or the same immunospecificity and characteristics as the parent or reference antibody or antigen binding fragment thereof. The amino acid substitutions or additions of such derivatives can include naturally occurring (i.e., DNA-encoded) or non-naturally occurring amino acid residues. The term "derivative" encompasses, for example, chimeric or humanized variants, as well as variants having altered CH1, hinge, CH2, CH3 or CH4 regions, to form, for example antibodies, etc., having variant Fc regions that exhibit enhanced or impaired effector or binding characteristics.

As used herein, a "chimeric antibody" is a molecule in which different portions of the antibody are derived from different immunoglobulin molecules such as antibodies having a variable region derived from a non-human antibody and a human immunoglobulin constant region.

As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they should be substantially identical to human immunoglobulin constant regions, i.e., at least about 85-99%, or about 95% or more identical. Hence, all parts of a humanized immunoglobulin, except possibly the CDR's, are substantially identical to corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human.

The term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating," "treatment" and "therapeutic use" refer to the elimination, reduction, or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, an "immune cell" refers to any cell from the hemopoietic origin including, but not limited to, T cells, B cells, monocytes, dendritic cells, and macrophages.

As used herein, "inflammatory molecules" refer to molecules that result in inflammatory responses including, but not limited to, cytokines and metalloproteases such as including, but not limited to, IL-1β, TNF-α, TGF-beta, IFN-γ, IL-18, IL-17, IL-6, IL-23, IL-22, IL-21, and MMPs.

As used herein, "valency" refers to the number of binding sites available per molecule.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

As used herein, the terms "individual," "host," "subject," and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index based on its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±12 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water, and emulsions such as an oil/water or water/oil emulsion, and various types of wetting agents.

II. SARS-CoV2 Binding Moieties

Previous beta coronavirus outbreaks from SARS-CoV-1 (2003) and MERS-CoV (2008) have highlighted the utility of antibody response in the quick diagnosis of infection and informed on current SARS-CoV-2 vaccine design, especially concerning the epitope motifs to target for virus neutralization. Of great interest is the ~300 amino acid receptor binding domain (RBD) of the S1 subunit of the spike protein (FIG. 1A). The S1 RBD contains the five contact residues (L455, F486, Q493, S494, N501) (Shang, J, et al., *Nature* 2020, 581, 221-224; Wan, Y., et al. *J. Virol.* 2020, 94, e00127-00120. previously shown to be important for viral entry through interactions with the human angiotensin converting enzyme 2 (hACE2) receptor present on many cell types, especially lung epithelial cells. Upon viral exposure, humoral immunity results in antibody development that, when targeted to this region, can block viral entry.

Disclosed herein are multiple fully-defined nanomolar-affinity mouse mAbs created by an accelerated immunization and hybridoma screening process, twelve of which are capable of efficient virus neutralization in vitro and two which robustly stain lung tissue from COVID-19 patients.

One embodiment provides antibody or antigen-binding fragments thereof that bind, preferably specifically, to a SARS-CoV-2 spike protein. Optionally, the antibody is a monoclonal antibody, antibody fragment, chimeric antibody, humanized antibody, single-chain antibody or antibody that competitively inhibits the binding of an anti-SARS-CoV protein antibody or antigen-binding fragment thereof to its respective antigenic epitope. In one embodiment, the disclosed antibodies can optionally be produced in Chinese hamster ovary (CHO) cells or in bacterial cells and preferably inhibit, reduce, or prevent the binding of coronaviruses, including but not limited to SARS-CoV-2 spike protein to cell surface proteins in a subject. In some embodiments, the disclosed antibodies and antigen-binding fragments thereof reduce or inhibit the growth or proliferation of or induce the death of a cell infected with a coronavirus to which they bind.

In another embodiment, the disclosed antibodies and antigen-binding fragments thereof are detectably labeled, attached to a solid support, or the like, such as a lateral flow assay device which provides for point-of-care detection of SARS-CoV-2 and/or diagnosis.

Yet another embodiment provides vectors comprising nucleic acids, including but not limited to DNA, encoding any of the herein described antibodies and antigen-binding fragments thereof. Host cells comprising any such vector are also provided. By way of example, the host cells may be CHO cells, bacterial cells (such as *E. coli*) used for recombinant protein expression, or yeast cells. A process for producing any of the herein described antibodies is further provided and comprises culturing host cells under conditions suitable for expression of the desired antibody and recovering the desired antibody from the cell culture.

A. Exemplary Antibodies

This disclosure includes the following amino acid sequences:

| SEQ ID NO | Description | Sequence |
|---|---|---|
| 1 | 3C4 clone heavy chain and 3E4 clone heavy chain | EVQLQQSGAELVKPGASVKLSCTASGFNIKDTYIHWVKQRPE QGLEWIGRIDPASGKTEYDPNFQGKATMTADTSSNTAYLQLS SLTSEDTAVYYCASGYDVNYELDYWGQGTSVTVSS |
| 2 | 3C4 clone light chain and 3E4 clone heavy chain | DIQMNQSPSSLSASLGDTITITCHASQNINVWLSWYQQKPGNI PKLLIYKASNLHTGVPSRFSGSGSGTGFTLTISSLQPEDIATYY CQQGQSYPYTFGGGTKLEIK |
| 3 | 4F11 clone heavy chain | QAVVTQESALTTSPGETVTLTCRSSTGAVTTSNYANWVQEKP DHLFTGLIGGTNNRAPGVPARFSGSLIGDKAALTITGAQTEDE AIYFCALWYSNISLFVIFGSGTKVTVL |
| 4 | 4F11 clone light chain | DIVMSQSPSSLAVSVGEKVTMSCKSSQSLLYSSNQKNYLAW YQQKPGQSPKLLIYWASTRESGVPDRFTGSGSGTDFTLTISSV KAEDLAVYYCQQYYSYPWTFGGGTKLEIK |
| 5 | 3G1 clone heavy chain | QVQLKQSGPGLVQPSQSLSITCTVSGFSLTSYGVHWVRQSPGK GLEWLGVIWSGGSTDYNAAFISRLSISKDNSKSQVFFKMNSLQ ANDTAIYYCAKYRYDSFAYWGQGTLVTVSA |
| 6 | 3G1 clone light chain | DIVLTQSPASLAVSLGQRATISCRASKSVSTSGYSYMYWYQQ KPGQPPKLLIYLASNLESGVPARFSGSGSGTDFTLNIHPVEEE DAATYYCQHSRELPYTFGGGTKLEIK |
| 7 | 3A6 clone heavy chain | QVQLKESGPGLVAPSQSLSITCTVSGFSLISYGVHWVRQPPGK GLEWLGVIWAGGSTNYNSALMSRLSINKDNSKSQVFLKINSL QTDDTAMYYCGRDYGILLIDYWGQGTTLTVSS |
| 8 | 3A6 clone light chain | ENVLTQSPAIMSASPGEKVTMTCSASSSVSYMHWYQQKSSTS PKLWIHDTSKLASGVPGRFSGSGSGNSYSLTVSSMEAEDVAT YYCFQGSGYPFTFGSGTKLEIK |
| 9 | 3B3 clone heavy chain | DVQLQESGPGLVKPSQSLSLTCTVTGYSITSDYAWIWIRQFPG NKLEWMAYISYSGTTSYNPSLKSRISITRDTSKNQFFLQLNSVT TEDTATYYCAGRRGAYYGNYEEDYWGRGTSVTVSS |
| 10 | 3B3 clone light chain | QIVLTQSPAIMSASPGEKVTMTCSSSSIVNYMYWYQQKPGSSP RLLIYDTSTLASGVPVRFSGSGSGTSYSLTISRMEAEDAATYY CQQWSSYPYTFGGGTKLEIK |
| 11 | 3D7 clone heavy chain | EVQLQQSGAELVKPGASVKLSCTASGFNIKDTYMYWVKQRP EQGLEWIGRIDPANGNSKYDPKFQGKATITADTSSNTAYLQLS SLTSEDTAVYYCARSYYDYDGGGCFDYWGQGTTLTVSS |
| 12 | 3D7 clone light chain | RIVMTQTPKFLPVSAGDRVTITCKASQSVSNDVAWYQQKPGQ SPKPLIYYASNRYTGVPDRFTGSGYGTDFTFTISTVQTEDLAIY FCQQGYSSPLTFGAGTKLELK |
| 13 | 3E5 clone heavy chain | EVQLQQSGPELVKPGASVKISCKASGYSFTGYFMNWVKQSH GKSLEWIGRINPYNGDTFYNQKFKGKATLTVDKSSNTAHMEL LSLTSEDSAVYYCGLRTYWGQGTLVTVSA |
| 14 | 3E5 clone light chain | DILMTQSPSSMSVSLGDTVNITCHASQDINNNIGWLQQRPGKS FKGLIYHGTNLEDGVPSRFSGSGSGTDYSLTISSLESEDFADYY CVQSVQFPYTFGGGTKLEIK |
| 15 | 3B4 clone heavy chain | EVKLQQSGAELVKPGASVKLSCTASGFNIKDTYMHWVKQRP EQGLEWIGRIDPANGDTKYDPNFQVKATITADTSSNTASLQFS SLTSEDTAVYYCARSYYYGTTSWFASWGQGTLVTVSA |
| 16 | 3B4 clone light chain | DIQMTQSSSSFSVSLGDRVTITCKASEDIYNHLAWYQQKPGNA PRLLISGAPSLETGVPSRFSGSGSGKDYTLSITSLQTEDVATYY CQQYWSTPYTFGGGTKLEIK |
| 17 | 3D1 clone heavy chain | EVQLQQSGAELVKPGASVKLSCTASGFNIKDTYMYWVKQR PEQGLEWIGRIDPANGNTKYDPKFQGKATIAADTSSNTAYM QLSSLTSEDTAVYYCARWDFGNYVDYAMDYWGQGTSVTV SS |
| 18 | 3D1 clone light chain | DIKMIQSPSSMYVSLGERVTITCKASQDLYSFLSWFQQKPGKS PKTLIYRANRLVDGVPSRFSGSGSGQDYSLTISSLEYEDMGIY YCLQYDAFPWTFGGGTKLEIK |

-continued

| SEQ ID NO | Description | Sequence |
|---|---|---|
| 19 | 3A2 clone heavy chain | QVTLKESGPGILQPSQTLSLTCSFSGFSLSTSGMGVSWIRQPSG KGLEWLAHIYWDDDKRYNPSLKSRLTISKDTSSSQVFLKITSV DTVDTATYYCARRGPLITTDGTFDVWGAGTTVTVSS |
| 20 | 3A2 clone light chain | DIVMTQSRKFMSTSVGDRVSITCKASQDVGTSVAWYQQKPG QSPKLLIYWASTRHTGVPDRFTGSGSGTDFTLTINSVQSEDLA DYFCQQYSSYPYTFGGGTKLEMK |
| 21 | 3C6 clone heavy chain | QVTLKESGPGILQPSQTLSLTCSFSGFSLSTSGMGVSWIRQPSG KGLEWLAHIYWDDDKRYNPSLKSRLTISKDTSSNQVFLKIISV DTVDTATYYCARRGPLITTDGTFDVWGAGTTVTVSS |
| 22 | 3C6 clone light chain | DIVMTQSHKFLSTSVGDRVTITCKASQDVDTAVAWYQQKPG QSPKLLIYWASIRHTGVPDRFTGSGSGTDFTLTISNVQSDDLA DYFCQQYSSYPYTFGGGTKLEIE |
| 23 | 3H5 clone heavy chain | EVQLQQSGPELVKPGASVKISCKASGYSFTGYFMNWVKQSH GKSLEWIGRINPYNGDTFYNQKFKGKATLTVDKSSSTAHMEL LSLTSEDSAVYYCGRGLYGKGYYYAMDYWGQGTSVTVSS |
| 4 | 3H5 clone light chain | DIVMSQSPSSLAVSVGEKVTMSCKSSQSLLYSSNQKNYLAWY QQKPGQSPKLLIYWASTRESGVPDRFTGSGSGTDFTLTISSVK AEDLAVYYCQQYYSYPWTFGGGTKLEIK |
| 24 | 3G7 clone heavy chain | QVQLQQPGTELVRPGASVKLSCKASGYSFTSYWMNWVKQRP GQGLEWIGMIHPSDSETRLNQKFKDKATLTVDKSSSTAYMQL SSPTSEDSAVYYCARSSGYDWYFDVWGAGTTVTVSS |
| 25 | 3G7 clone light chain | DIVLTQSPASLAVSLGQRATISCRASESVDSYGNSFMHWHQQ KPGQPPKLLIYRASNLESGIPARFSGSGSRTDFTLTINPVEADD VATYYCQQSNEDPWTFGGGTKLEIK |
| 19 | 3A7 clone heavy chain | QVTLKESGPGILQPSQTLSLTCSFSGFSLSTSGMGVSWIRQPSG KGLEWLAHIYWDDDKRYNPSLKSRLTISKDTSSSQVFLKITSV DTVDTATYYCARRGPLITTDGTFDVWGAGTTVTVSS |
| 20 | 3A7 clone light chain | DIVMTQSRKFMSTSVGDRVSITCKASQDVGTSVAWYQQKPG QSPKLLIYWASTRHTGVPDRFTGSGSGTDFTLTINSVQSEDLA DYFCQQYSSYPYTFGGGTKLEMK |
| 26 | 3C2 clone heavy chain | QVQLQQSGAELARPGASVKLSCKASGYAFTSYWMEWVKQR PGQGLEWIGSIYPGDGATRYTQKFKGKATLTADKSSSTAYME FSSLASEDSAVYFCARSGGYDWYFDVWGAGTTVTVSS |
| 27 | 3C2 clone light chain | DIVLTQSPASLAVSLGQRATISCRASETVDSYGNSFMHWYQQ KPGQPPKLLIYRASNLESGIPVRFSGSGSRTDFTLTINPVEADD VATYYCQQSNEDPWTFGGGTKLEIK |
| 28 | 3D5 clone heavy chain | EVQLQQSGAELVKPGASVTLSCTASGFNIKDTYMHWVKQRP EQGLEWIGRIDPANGNTKYDPKFQGKATITADTSSNTAYLQLS SLTSEDTAVYYCTRYYYGSSGFFDVWGAGTTVTVSS |
| 29 | 3D5 clone light chain | SIVMTQTPKFLLVSAGDRVTITCKASQSVSNDVAWYQQKPGQ SPKVLIYYASNRYTGVPDRFTGSGYGTDFTFTISTVQAEDLAV YFCQQDYSSPTFGAGTKLELK |
| 30 | 3F6 clone heavy chain | EVQLQQSGAELVKSGASVKLSCTASGFNIKDTYMHWVKQRP EQGLEWIGRIDPASGNTKYDPKFQGKATITSDTSSNTAYLQLS SLTSEDTAVYFCARSYYTYDGFFDVWGAGTTATVSS |
| 31 | 3F6 clone light chain | NIVMTQTPKFLLVSAGDRVTITCKASQSVSNDVAWYQQKPGQ SPKLLIYYASNRYTGVPDRFTGSGYGTDFTFTISTVQAEDLAV YFCQQDYSSPPTFGGGTKLEIK |
| 32 | 9F2 clone heavy chain | EVQLQQSGAELVKPGASVKLSCTASGFNIKDTYMYWVKQRP EQGLEWIGMIDPANGNTKYDPKFQGKATITADTSSNTAYLQL RSLTSEDTAVYYCARTYYYGSSYEAMDYWGQGTSVTVSS |
| 33 | 9F2 clone light chain | SIVMTQTPKFLLVSAGDRVTITCKASQSVSNDVAWYQQKPGQ SPKLLIYYASNRYTGVPDRFTGSGYGTDFTFTISTVQAEDLAV YFCQQDYSSPTFGGGTKLEIK |

-continued

| SEQ ID NO | Description | | Sequence |
|---|---|---|---|
| 34 | 1-3A1 | heavy chain | DVQLQESGPDLVKPSQSPSLTCTVTGYSITGDYSWHWIRQFPGNKLE WMGYIHYSGSADYNPSLKSRISITRDTSKNQFFLQLNSVTTEDTATYF CARWGNGKNAMDYWGQGTSVTVSS |
| 35 | 1-3A1 | light chain | DIQMTQSPASLSASVGETVTITCRASENIYSYLAWYQQKQGKSPQLL VYNTKTLAEGVPSRFSGSGSDTQFSLKINSLQPEDFGYYYCQHHYGS PPTFGGGTKLEIK |
| 36 | 1-3B1 | heavy chain | DVQLQESGPGLVKPSQSLSLTCSVTGYSITSGYYWNWIRQFPGNKLE WMGYIIYDGTNNYNPSLKNRISITRDTSKNQFFLKLNSVTSEDTATY YCARVDYDVGHWFAYWGQGTLVTVSA |
| 37 | 1-3B1 | light chain | ENVLTQSPAIMSASLGEKVTMSCRASSSVNYMYWYQQKSDASPKL WIYYTSNLAPGVPARFSGSGSGNSYSLTISSMEGEDAATYYCHQFTT SPWTFGGGTKLEIK |
| 9 | 1-3B3 | heavy chain | DVQLQESGPGLVKPSQSLSLTCTVTGYSITSDYAWIWIRQFPGNKLE WMAYISYSGTTSYNPSLKSRISITRDTSKNQFFLQLNSVTTEDTATYY CAGRRGAYYGNYEEDYWGRGTSVTVSS |
| 10 | 1-3B3 | light chain | QIVLTQSPAIMSASPGEKVTMTCSSSSIVNYMYWYQQKPGSSPRLLIY DTSTLASGVPVRFSGSGSGTSYSLTISRMEAEDAATYYCQQWSSYPY TFGGGTKLEIK |
| 30 | 1-3B6 | heavy chain | EVQLQQSGAELVKSGASVKLSCTASGFNIKDTYMHWVKQRPEQGLE WIGRIDPASGNTKYDPKFQGKATITSDTSSNTAYLQLSSLTSEDTAVY FCARSYYTYDGFFDVWGAGTTATVSS |
| 31 | 1-3B6 | light chain | NIVMTQTPKFLLVSAGDRVTITCKASQSVSNDVAWYQQKPGQSPKL LIYYASNRYTGVPDRFTGSGYGTDFTFTISTVQAEDLAVYFCQQDYS SPPTFGGGTKLEIK |
| 38 | 1-3C3 | heavy chain | EVQLQQSGPELVKPGASVKISCKTSGYTFTEYTMHWVKQSHGKSLE WIGGINPNNGGTSYNQKFKGKATLTVDKSSSTAYMELRSLTSEDSA VYYCARRQDGNYWFAYWGQGTLVTVSA |
| 39 | 1-3C3 | light chain | EIVLTQSPTTMAASPGEKITITCSASSSISSNYLHWYQQKPGFSPKLLI YRTSNLASGVPARFSGSGSGTSYSLTIGTMEAEDVATYYCQQGSSIPR ITFGAGTKLELK |
| 40 | 1-3D2 | heavy chain | QVQLQQSGAELAKPGASVKMSCKASGYTFSTYWIHWVQQRPGQGL EWIGYINPYTDYTEYNQKFKDKATLTADKSSNTAYMQLSSLTSEDS AVYYCARRYGNYDAWFTYWGQGTLVTVSA |
| 41 | 1-3D2 | light chain | DIVMTQSHKFMSTSVGDRVSITCKASQDVGTAVAWYQQKPGQSPK VLIYWASTRHTGVPDRFTGSGSGTDFTLTISNVQSEDLADYFCQQYR TFGGGTKLEIK |
| 32 | 1-3D3 | heavy chain | EVQLQQSGAELVKPGASVKLSCTASGFNIKDTYMYWVKQRPEQGLE WIGMIDPANGNTKYDPKFQGKATITADTSSNTAYLQLRSLTSEDTAV YYCARTYYYGSSYEAMDYWGQGTSVTVSS |
| 33 | 1-3D3 | light chain | SIVMTQTPKFLLVSAGDRVTITCKASQSVSNDVAWYQQKPGQSPKL LIYYASNRYTGVPDRFTGSGYGTDFTFTISTVQAEDLAVYFCQQDYS SPTFGGGTKLEIK |
| 32 | 1-3E1 | heavy chain | EVQLQQSGAELVKPGASVKLSCTASGFNIKDTYMYWVKQRPEQGLE WIGMIDPANGNTKYDPKFQGKATITADTSSNTAYLQLRSLTSEDTAV YYCARTYYYGSSYEAMDYWGQGTSVTVSS |
| 33 | 1-3E1 | light chain | SIVMTQTPKFLLVSAGDRVTITCKASQSVSNDVAWYQQKPGQSPKL LIYYASNRYTGVPDRFTGSGYGTDFTFTISTVQAEDLAVYFCQQDYS SPTFGGGTKLEIK |
| 42 | 1-3F1 | heavy chain | EVQLQQSGAELVKPGASVKLSCTASGFNIKDTYMHWVKQRPEQGLE WIGRIDPANGNTKYDPKFKDKAIITADTSSNTAYLQFSSLTSEDTAVY YCVSGYYYYGSPYGAMDYWGQGTSVTVSS |
| 43 | 1-3F1 | light chain | QIVLTQSPAIMSASPGEKVTISCSATSSVSYMYWYQQKPGSSPKPWIY HTSNLASGVPARFSGSGSGTSYSLTISNMEAEDAATYYCQQYHGYPL TFGAGTKLELK |
| 44 | 1-3F2 | heavy chain | QVQLQQPGAELVKPGASVKMSCKASGYTFTSYSLHWVKQTPGQGL EWIGAVYPGNDDTSYNQNFKGKATLTADKSSNTAYMQLSSLTSEDS AVYYCARDGYFAMDYWGQGTSVTVSS |

-continued

| SEQ ID NO | Description | | Sequence |
|---|---|---|---|
| 45 | 1-3F2 | light chain | DIVMSQSPSSLAVSVGEKVTMSCKSSQSLLYSTNQKNYLAWYQQKP GQSPKLLIYWASTRESGVPDRFTGSGSGTDFTLTISSVKAEDLAVYY CHQYYSYPWTFGGGTKLEIK |
| 46 | 1-3F4 | heavy chain | EVQLQQSGAELVKPGASVKLSCTASGFNIKDTYMHWVKQRPEQGLE WIGRIDPANDNTKYDPKFQGKATITADTSSNTAYLQLTSLTSEDTAV YYCTRYYDYVYAMDYWGQGTSVTVSS |
| 47 | 1-3F4 | light chain | DIQMTQSPASQSASLGESVTITCLASQTIGTWLAWYQQKPGKSPQLLI YAATSLADGVPSRFSGSGSGTKFSFRISSLQAEDFVSYYCQQLYSTPL TFGGGTKLEIK |
| 19 | 1-3F5 | heavy chain | QVTLKESGPGILQPSQTLSLTCSFSGFSLSTSGMGVSWIRQPSGKGLE WLAHIYWDDDKRYNPSLKSRLTISKDTSSSQVFLKITSVDTVDTATY YCARRGPLITTDGTFDVWGAGTTVTVSS |
| 20 | 1-3F5 | light chain | DIVMTQSRKFMSTSVGDRVSITCKASQDVGTSVAWYQQKPGQSPKL LIYWASTRHTGVPDRFTGSGSGTDFTLTINSVQSEDLADYFCQQYSS YPYTFGGGTKLEMK |
| 28 | 1-3G2 | heavy chain | EVQLQQSGAELVKPGASVTLSCTASGFNIKDTYMHWVKQRPEQGLE WIGRIDPANGNTKYDPKFQGKATITADTSSNTAYLQLSSLTSEDTAV YYCTRYYYGSSGFFDVWGAGTTVTVSS |
| 29 | 1-3G2 | light chain | SIVMTQTPKFLLVSAGDRVTITCKASQSVSNDVAWYQQKPGQSPKV LIYYASNRYTGVPDRFTGSGYGTDFTFTISTVQAEDLAVYFCQQDYS SPTFGAGTKLELK |
| 48 | 1-3G4 | heavy chain | EVQLQQSGPELVKPGASVKMSCKASGYTFTDYYMKWVKQSHGKSL EWIGDINPNNGDTFYNQKFKGKATLTVDKSSSTAYMQLNSLTSEDS AVYYCARGGYYRFAYWGQGTLVTVSA |
| 49 | 1-3G4 | light chain | DIVMTQSPSSLTVTAGEKVTMSCKSSQSLLNSGNQKNYLTWYQQKP GQPPKLLIYWASTRESGVPDRFTGSGSGTDFTLTISSVQAEDLAVYY CQNDYSYPLTFGAGTKLELK |
| 50 | 1-3G6 | heavy chain | EVQLQQSGAELVKPGASVKLSCTASGFNIKDTNMHWVKQRPEQGLE WIGRIDPANGDTKYDPKFQGKATITADTSSNTAYLQLSSLTSEDTAV YYCARLNYDGYYDYAMDYWGQGTSVTVSS |
| 51 | 1-3G4 | light chain | DIKMTQSPSSMYASLGERVTITCKASQDINSFLSWFQQKPGKSPKTLI YRANRLVDGVPSRFSGSGSGQDYSLTISSLEYEDMGIYYCLQYDEFP FTFGSGTKLEIK |
| 52 | 1-3H2 | heavy chain | QVQLQQSGAELMKPGASVKISCKATGNTFSNYWIEWVKQRPGHGL EWIGEILPGSDSTNYNEKFKGKATFTADTSSKTAYMQLSSLTSEDSA VYYCARNRFYWYFDVWGAGTTVTVSS |
| 53 | 1-3H2 | light chain | DVVMTQTPLSLPVSLGDQASISCRSSQSLVHSNGNTYLHWYLQKPG QSPKLLIYKVSNRFSGVPDRFSGSGSGTDFTLKISRVEAEDLGIYFCSQ STHVPWTFGGGTKLEIK |
| 54 | 1-3H4 | heavy chain | EVQLQQSGAELVKPGASIKLSCTASGFNIKDTYMYWVKQRPEQGLE WIGRIDPANGNSKYDPKFQGKATITADTSSNTAYLHLSSLTSEDTAV YYCARSYYDYDGGGCFDYWGQGTTLTVSS |
| 55 | 1-3H4 | light chain | RIVMTQTPKFLPVSVGDRVTITCKASQSVSNDVAWYQQKPGQSPKP LIYYASNRYTGVPDRFTGSGYGTDFTFTISTVQTEDLAIYFCQQGYSS PLTFGAGTKLELK |
| 56 | 1-3H6 | heavy chain | EVQLVESGGGLVQPKGSLKLSCAASGFTFNTYAMNWVRQAPGKGL EWVARIRSKSDNFAMYYADSVKDRFTISRDDSQSMLYLQMSNLKTE DTAMYYCASYDGYRAWFAYWGQGTLVTVSA |
| 57 | 1-3H6 | light chain | DVVMTQTPLSLPVSLGDQASISCRSSQSLVHSNGNTYLHWYLQKPG QSPKLLIYKVSNRFSGVPDRFSGSGSGTDFTLKISRVEAEDLGVYFCS QSTHVPWTFGGGTKLEIK |
| 58 | 1-8C2 | heavy chain | EVKLEESGGGLVQPGGSMKLSCVASGFTFSNYWMNWVRQSPEKGL EWVAEIRLKSNNYATHYAESVKGRFTISRDDSKSSVYLQMNNLRAE DTGIYYCTSRAYWGQGTLVTVSA |

-continued

| SEQ ID NO | Description | | Sequence |
|---|---|---|---|
| 59 | 1-8C2 | light chain | DIVMTQSHKFMSTSVGDRVSITCKASQDVGTAVAWYQQKPGQSPKL LIYWASTRHTGVPDRFTGSGSGTDFTLTISNVQSEDLADYFCQQYSS YPYTFGGGTKLEIK |
| 60 | 1-8D1 | heavy chain | QVQLQQPGAELVKPGASVKLSCKASGYTFISYWMHWVKQRPGQGL EWIGEINPSNGRSNYNEKFKSKATLTVDKSSSTAYMQLSSLTSEDSA VYYCARGDYDGSYWYFDVWGAGTTVTVSS |
| 61 | 1-8D1 | light chain | DIVLTQSPASLAVSLGQRATISCRASESVDNYGISFMNWFQQKPGQP PKLLIYAASNQGSGVPARFSGSGSGTDFSLNIHPMEEDDTAMYFCQQ SKEVPPTFGGGTKLEIK |
| 62 | 1-5A1 | heavy chain | QVQLQQPGAELVKPGASVKMSCKASGYTFTSYNIHWVKQTPEQGLE WIGAIYPENGDTSYNQKFKGKATLTADKSSSTAYMQLSSLTSEDSAV YYCTRDGYDGGAHYGLDYWGQGTSVTVSS |
| 63 | 1-5A1 | light chain | DIVLTQSPASLAVSLGQRATISCRASKSVSTSGYSFIHWYQQKPRQPP KFLIYLASNLESGVPARFSGSGSGTDFTLNIHPVEEEDAATYYCHHTR ELPWTFGGGTKLEIK |
| 64 | 3-13A1 | heavy chain | EVQLQQSGPELVKPGASVKISCKTSGYTFTEYTIYWVKQSHGKSLEW IGGINPNNGDTIYNQNFKGKATLTVDKSSSTAYMELRSLTSEDSAVY YCARDDYGGIAYWGQGTSVTVSS |
| 65 | 3-13A1 | light chain | DIVMSQSPSSLAVSVGEKVTMSCKSSQSLLYSSNQKNYLAWFQQKP GQSPKLLIYWASTRESGVPDRFTGSGSGTDFTLTISSVKAEDLAVYY CQQYYRYPLTFGGGTKLEIK |
| 66 | 5-1A5 | heavy chain | EVKLVESGGGLVKPGGSLKLSCAASGFTLSNYAMSWVRQTPEKRLE WVASISSGGSIYYLDSVKGRFTISRDNARNILYLQMSILRSGDTAMY YCVSGSGNYVDSPMDYWGQGTSVTVSS |
| 67 | 5-1A5 | light chain | QVVLTQSPAIMSASLGEEITLTCSASSSVSYMNWYQQKSGTSPKLLIY STSNLASGVPSRFSGSGSGTFYSLTISSVEAEDAADFYCHQWSSWTF GGGTKLEIK |
| 68 | 5-1E5 | heavy chain | EVQLQQSGAELVRSGASVKLSCTASGLNFKDYYMHWVKQRPEQGL EWIGWIDPENGDTDYAPKFQGKATMTADTSSNTAYLQLSSLTSEDT AVYFCNAALGYWGQGTTLTVSS |
| 69 | 5-1E5 | light chain | DAVMTQTPLSLPVSLGDQASISCRSSQSLENSNGNTYLNWYLQKPG QSPQLLIYRVSNRFSGVLDRFSGSGSGTDFTLKISRVEAEDLGVYFCF QVTHVPYTFGGGTKLEIK |
| 70 | 5-1F2 | heavy chain | QIQLVQSGPELKKPGETVKISCKASGYTFTOYSIHWVKQAPGKGLK WMGWINTETGEPTCADDFKGRFAFSLETSASTAYLQINNLKNEDTST YFCLRYWGIYVEWYFDLWGAGTTVTVSS |
| 71 | 5-1F2 | light chain | DVLMTQTPLSLPVRLGDQASISCRSSQSILHSNGNTYLEWYLQKPGQ FPKLLIYKVSNRFSGVPDRFSGSGSGTDFTLKISRVESEDLGVYYCFQ GSHVPLTFGAGTKLELK |
| 72 | 5-1F6 | heavy chain | QVQLQQPGAELVRPGASVNLSCKASGYTFTNYWINWVRQRPGQGL EWIGNIYPSDVYTNYNQKFKDKATLTVDKSSSTAYMQLSSPTSDDSA VYYCTRIYYYISSYAGAMDYWGQGTSVTVSS |
| 73 | 5-1F6 | light chain | NIVLTQSPRSMSMSVGERVTLSCKASENVGTYVSWYQQKPEQSPKL LIYGASNRYTGVPDRFTGSGSATDFSLTISSVQAEDLADYHCGQSFSY PLTFGAGTKLELK |
| 74 | 5-1F8 | heavy chain | QIQLVQSGPELKKPGETVKISCKASGYTFTDYSMQWVKQAPGKGLK WMGWINTETGEPTYTODFKGRFAFSLETSASTAYLQINILKNEDTAT YFCARPHYDYYWYFDVWGAGTTVTVSS |
| 75 | 5-1F8 | light chain | DVLMTQIPLSLPVSLGNQASISCRSSQNIVHSDGNTYLEWYLQKPGQ SPKILIYKVSNRFSGVPDRFSGSGSGTDFTLKISRVEAEDLGVYYCFQ GSHAPPTFGAGTKLELK |
| 76 | 5-2B6 | heavy chain | QVQLQQPGAELVKPGASVKMSCKASGYTFTSTWMHWVKQRPGQG LEWIGTIDPSDSYASYNQKFKGKATLTVHTSSSTAYMQLSSLTSEDS AVYYCTANLDYWGQGTTLTVSS |
| 77 | 5-2B6 | light chain | DVVVTQTPLSLPVSFGDQVSISCRSSQSLANSYGNTYLSWYLHKPGQ SPQLLIYGISNRFSGVPDRFSGSGSGTDFTLKISTIKPEDLGMYYCLQG THQPYTFGGGTKLEIK |

-continued

| SEQ ID NO | Description | | Sequence |
|---|---|---|---|
| 78 | 5-2D2 | heavy chain | DVKLVESGGGLVKLGGSLKLSCAASGFTFSSYYMSWVRQTPEKRLELVAAINSNGGSTYYPDTVKGRFTISRDNAKNTLYLQMSSLKSEDTALYYCARHPLGLPSWFAYWGQGTLVTVSA |
| 79 | 5-2D2 | light chain | DIVMTQSQKFMSTSVGDRVSVTCKASQNVGTNVAWYQQKPGQSPKALIYSASYRYSGVPDRFTGSGSGTDFTLTISNVQSEDLAEYFCQQYNSYPRTFGGGTKLEIK |
| 80 | 5-3D2 | heavy chain | QVQLQQSGPELVKPGASVRISCKASGYTFTSYYIHWVKQRPGQGLEWIGWIYPGNVNTKYNEKFKGKATLTADKSSSTAYMQLSSLTSEDSAVYFCARRGIYYRYDDYAMDYWGQGTSVTVSS |
| 81 | 5-3D2 | light chain | NIVLTQSPASLAVSLGQRATISCRASESVDSYGNSFMHWYQQKPGQPPKLLIYLASNLESGVPARFSGSGSRTDFTLTIDPVEADDAATYYCQQNNEDPWTFGGGTKLEIK |
| 82 | 5-3G1 | heavy chain | EVQLQQSGAELVKPGASVKLSCTASGFNIKDAYMHWMKQRPEQGLEWIGRIDPANGNTKYDPKFQGKATITADTSSNTAYLQLSSLTSEDTAVYYCARKGGYYLYYHAMDCWGQGTSVTVSS |
| 83 | 5-3G1 | light chain | DIVLTQSPASLAVSLGQRATISCKASQSVDYDGDSFMNWYQQKPGQPPKLLIYAASNLESGIPARFSGSGSGTDFTLNIHPVEEEDAATYYCQQSNEDPPTFGSGTKLEIK |
| 84 | 5-5A2 | heavy chain | QVQIQQSGAELARPGASVKLSCKASGYTFTIYWMQWVKQRPGQGLEWIGSIYPGDGNTRYTQKFKGKATLTADKSSSTAYMQLSSLTSDDSAVYYCARSVTYDWYFDVWGAGTTVTVSS |
| 85 | 5-5A2 | light chain | DIVVTHSPASLAVSLGQRATISCRASESVDSYGNSFMHWYQQKPGQPPKLLIYRASNLESGIPARFSGSGSRTDFTLTINPVEADDVATYYCQQSNEVPWTFGGGTKLEIK |
| 86 | 5-5B2 | heavy chain | QVQLQQSGPELVKPGASVKISCKASGYAFSYSWMNWVKQRPGQGLEWIGRIYPGDGDTNYNGKFKGKATLTADKSSSTAYMQLSSLTSVDSAVYFCTRWDYDGYYENTMDYWGQGTSVTVSS |
| 87 | 5-5B2 | light chain | DIKMTQSPSSMYASLGERVTITCKASQDINSYLSWFQQKPGKSPKTLIYRANRLVDGVPSRFSGSGSGQDYSLTISSLEYEDMGIYYCLQYDEFPYTFGGGTKLEIK |
| 88 | 5-5D2 | heavy chain | DVQLVASGGGLVQPGGSRKLSCAASGFTFSNFGMHWVRQAPEKGLEWVAYISSGSSTIYYTDTLKGRFTISRDNPKNTLFLHMTSLTSEDTAMYYCVRSAHGYYGWFAYWGQGTLVTVSA |
| 89 | 5-5D2 | light chain | DIVMSQSPSSLAVSVGEKVTMSCMSSQSLLYSTDQKNYLAWYQQKPGQSPKLLIYWASTRESGVPDRFTGSGSGTDFTLTISSVKAEDLAVYYCQQYYSYPWTFGGGTKLEIK |
| 88 | 5-5F2 | heavy chain | DVQLVASGGGLVQPGGSRKLSCAASGFTFSNFGMHWVRQAPEKGLEWVAYISSGSSTIYYTDTLKGRFTISRDNPKNTLFLHMTSLTSEDTAMYYCVRSAHGYYGWFAYWGQGTLVTVSA |
| 89 | 5-5F2 | light chain | DIVMSQSPSSLAVSVGEKVTMSCMSSQSLLYSTDQKNYLAWYQQKPGQSPKLLIYWASTRESGVPDRFTGSGSGTDFTLTISSVKAEDLAVYYCQQYYSYPWTFGGGTKLEIK |
| 90 | 5-5H1 | heavy chain | EVQLQQSGAELVKPGASVKLSCTASGFNIKDIYMHWVKQRPEQGLEWIGRIDPANGKTKYDPKFQGKATIIADTSSNTAYLQLSSLTSEDTAVYYCTRTPDYYGSYWGQGTLVTVSA |
| 91 | 5-5H1 | light chain | DIVLTQSPASLAVSLGQRATIFCKASQSVDYDGDSYMNWYQQKPGQPPKLLIYAASNLESGIPARFSGSRSGTDFTLNIHPVEEEDAATYYCQQSNEDPFTFGSGTKLEIR |
| 92 | 6-1B1 | heavy chain | EVQLQQSGPELVKPGSSVKISCKTSGYIFTEYTMYWVKQSHGKSLEWIGGNNPNTGDTTYNQKFKGKATLTVDKSSGTAYLELRSLTSEDSAVYYCARDRYDRAMDYWGQGTSVTVSS |
| 93 | 6-1B1 | light chain | DIQMTQSPSSLSASLGERVSLTCRASQEISGYLNWLQQKPDGTIKRLIYAASTLDSGVPKRFSGSRSGSDYSLTISSLESEDFADYYCLQYASYPLTFGAGTKLELK |

-continued

| SEQ ID NO | Description | | Sequence |
|---|---|---|---|
| 92 | 6-1F1 | heavy chain | EVQLQQSGPELVKPGSSVKISCKTSGYIFTEYTMYWVKQSHGKSLE WIGGNNPNTGDTTYNQKFKGKATLTVDKSSGTAYLELRSLTSEDSA VYYCARDRYDRAMDYWGQGTSVTVSS |
| 93 | 6-1F1 | light chain | DIQMTQSPSSLSASLGERVSLTCRASQEISGYLNWLQQKPDGTIKRLI YAASTLDSGVPKRFSGSRSGSDYSLTISSLESEDFADYYCLQYASYPL TFGAGTKLELK |
| 94 | 6-3B1 | heavy chain | QVTLKESGPGILQPSQTLSLTCSFSGFSLSTSGMGVSWIRQPSGKGLE WLAHMYWDDDKRYNPSLKSRLTISKSTSSNQVFLKITSVDTADTAT YYCARREIHDFDGWFAYWGQGTLVTVSA |
| 95 | 6-3B1 | light chain | DIVMTQSQKFMSTSVGDRVSVTCKASQNVGSSVAWYQQKPGQSPK ALVYSASSRYSGVPDRFTGSGSGTDFTLTISNVQSEDLAEYFCQQYN NYPLTFGAGTKLELK |
| 96 | 6-3C1 | heavy chain | EVQLQQSGPELVKPGASVKMSCKASGYTFTSYVMHWVKQICPGQGL EWIGYINRYNDGTEYNEKFKGKATLTSDKSSSTAYMELSSLTSEDSA VYYCARSDYGYDYTMDYWGQGTSVTVSS |
| 97 | 6-3C1 | light chain | DIVLTQSPASLAVSLGQRATISCRASESVDNYGISFMNWFQQKPGQP PKLLIYTASNQGSGVPARFSGSGSGTDFSLNIHPMEEDDAAMYFCQQ TKEVPYTFGGGTKLEIK |
| 98 | 6-4B2 | heavy chain | EVQLQQSGAELVRPGALVKLSCNASGFNIKDYFMNWVKQRPEQGL EWIGWIDPENGNSIYDPKFQGKASITADTSSNTAYLQLSSLTSEDTAV YYCATRDGGAWFAYWGQGTLVTVSA |
| 98 | 6-4B2 | heavy chain | EVQLQQSGAELVRPGALVKLSCNASGFNIKDYFMNWVKQRPEQGL EWIGWIDPENGNSIYDPKFQGKASITADTSSNTAYLQLSSLTSEDTAV YYCATRDGGAWFAYWGQGTLVTVSA |
| 99 | 6-4B2 | light chain | GIVMTQSQKFMSASVGDRVSVTCKASQNVVTNVAWYQQKPGQSPK ALIYSASYRYSGVPDRFTGSGSGTDFTLTISNVQSEDLAEYFCQQYNS YPLTFGSGTNLEIK |
| 99 | 6-4B2 | light chain | GIVMTQSQKFMSASVGDRVSVTCKASQNVVTNVAWYQQKPGQSPK ALIYSASYRYSGVPDRFTGSGSGTDFTLTISNVQSEDLAEYFCQQYNS YPLTFGSGTNLEIK |
| 98 | 6-4C1 | heavy chain | EVQLQQSGAELVRPGALVKLSCNASGFNIKDYFMNWVKQRPEQGL EWIGWIDPENGNSIYDPKFQGKASITADTSSNTAYLQLSSLTSEDTAV YYCATRDGGAWFAYWGQGTLVTVSA |
| 99 | 6-4C1 | light chain | GIVMTQSQKFMSASVGDRVSVTCKASQNVVTNVAWYQQKPGQSPK ALIYSASYRYSGVPDRFTGSGSGTDFTLTISNVQSEDLAEYFCQQYNS YPLTFGSGTNLEIK |
| 100 | 7-1D1 | heavy chain | QVQLQQPGAELVKPGASVKMSCKAS GYTFTSYNIHWVKQTPGQGLEWIGAIYPGNGDISYNQKFKGKATLT ADKSSSTAYMHLSSLTSEDSAVYYCARDGDYVRGFAYWGQGTLVT VSA |
| 101 | 7-1D1 | light chain | NIVLTQSPASLAVSLGQRATISCRASESVDSYGYSFMHWYLQKPGQP PKLLIYLASNLESGVPARFSGSGSRTDFILIIEPVEADDAATYYCQQN NEDPWTLGGGTKLEIK |
| 102 | 7-3C4 | heavy chain | DVQLVESGGGLVKPGGSLKLSCAASGFAFSIYDMSWVRQIPEKRLE WVAYISSGGGSTDYLDTVKGRFTISRDNAKNTLYLQMSSLKSEDTA MYYCARHNWDFDYWGQGTPLTVSS |
| 103 | 7-3C4 | light chain | DIVMTQSHKFMSTSVGDRVSITCKASQDVGSAVAWYQQKAGQSPK LLIYSASYRYTGVPDRFTGSGSGTDFTFTISSVQAEDLAVYYCQQHS GTPLTFGAGTKLELK |
| 104 | 7-3F5 | heavy chain | QVQLQQSGPELVKPGASVKISCGASGYTFTNYFIHWVRQRPGQGLE WIGWIYPGDVNTQYNERFKDKAILTADKSSTTAYMQLTSLTSEDSA VYFCTRRQNFGSFFDYWGQGTTLTVSS |
| 105 | 7-3F5 | light chain | DIQMTQTTSSLSASLGDRVTISCRASQAINNYLNWYQQKPDGTVKLL IYYTSKLHSGVPSRFSGSGSGTHYSLTISNLEQEDIATYFCQQGDTLP YTFGGGTNLEIK |

-continued

| SEQ ID NO | Description | Sequence |
|---|---|---|
| 106 | 7-3H3 heavy chain | QVQLEQSGPELVRPGTSVKMSCKASGYAFTSYLIEWVKQRPGQGLEWIGVINPGSGGIKDNEKFRGKATLTADKSSNTAFLQLSSLTSDDSALYFCTRNLPGSGYFDVWGAGTTVTVSS |
| 107 | 7-3H3 light chain | EILLTQSPAIIAASPGEKVTITCSASSSVSYMNWYQQKPGSSPKIWIYGISNLASGVPARFSGSGSGTSFSFTINSMEAEDVATYYCQQRSGYPLTFGAGTKLELK |
| 108 | 7-5A2 heavy chain | QVQLKQSGPGLVQPSQSLSITCTVSGFSLTSYGVHWVRQSPGKGLEWLGVIWSGGSTOYNAAFISRLSISKDNSKSQVFFKMNSLQANDTAIYYCARGWFSYYLDYWGQGTTLTVSS |
| 109 | 7-5A2 light chain | DIQMTQSPASLSVSVGETVTITCRASESIYSNLAWYQQKQGKSPQLLVYAATNLADGVPSRFSGSGSGTQYSLKINSLQSEDFGSYYCQHFWDNTWTFGGGTKLEIK |
| 110 | 7-5A3 heavy chain | EVQLQQSGPELVKPGASVKISCKTSGYTFTEYTIYWVKQSHGKSLEWIGGINPNNGDTIYNQNFKGKATLTVDKSSSTAYMELRSLTSEDSAVYYCARDDYGGIAYWGQGTLVTVSA |
| ill | 7-5A3 light chain | DIVMSQSPSSLAVSVGEKVTMSCKSSQSLLYSSNQKNYLAWFQQKPGQSPKLLIYWASTRESGVPDRFTGSGSGTDFTLTISSVKAEDLAVYYCQQYYRYPLTFGAGTKLELK |
| 112 | 7-5A4 heavy chain | EVQLQQSGPELVRPGASVKISCKTSGYTFTEYTIHWVKQSHGKSLEWIGGINPNNGDTTYNQRFKGRATLTVDKSSSTAYMELRSLTSEDSAVYYCPREDYRNDEKIPFDYWGQGTTLTVSS |
| 113 | 7-5A4 light chain | DIVMSQSPSSLTVSVGENITMSCKSSQSLLYSNNQKNYLAWYQQKPGQSPKLLIYWASTRESGVPDRFTGSGSGTDFTLTISSVKAEDLAVYYCQQYYSFPLTFGAGTKLDLK |
| 114 | 7-5B1 heavy chain | EVQLQQSGPELVKPGASVKISCKASGYSFTDYFMTWVKQNHGKSLEWIGRINPYNGDTFYNQKFKGKATLAVDKSSSTAHMELLSLTSEDSAVYYCGRFYRNGDFDVWGAGTTVTVSS |
| 115 | 7-5B1 light chain | DIVMTQSHKFMSTSVGDRISITCKASQDVNIAVAWYQQKPGQSPEVLIYSASYRFTGVPDRFTGSGSGTDFTFTISSVQAEDLAVYHCQQHYSIPYTFGGGTKLEIK |
| 116 | 7-5B3 heavy chain | QVQLKESGPGLVAPSQSLSITCTVSGFSLTSYGVHWVRQPPGKGLEWLGAIWAGGSINYNSALMSRLSISKDNSKSQVFLKMNSLQTDDTAMYYCARGPRYDRAMDYWGQGTSVTVSS |
| 117 | 7-5B3 light chain | DILLTQSPAILSVSPGERVSFSCRASQSIGTSIHWYQQRTNGSPRLLIKYASESISGIPSRFSGSGSGTDFTLNINSVESEDIADYYCQQSNSWPTYTFGGGTKLEIK |
| 118 | 7-5C3 heavy chain | EVKLLESGGGLVQPEGSLKLSCAASGFDFSRYWMSWVRQAPGKGLEWIGEINLDSSTINYAPSLEDKFIISRDNAKSTLYLQMSKVRSEDSALYYCAREFYGGSYLDYWGQGTTLTVSS |
| 119 | 7-5C3 light chain | DIQMTQSPASLSVSVGETVTITCRASDNIYNNLAWYQQKQGKSPQLLVYVATNLADGVPSRFSGSGSGTQYSLKIDSLQSEDFGTYYCQHFWGTPWTFGGGTKLEIK |
| 110 | 7-5C4 heavy chain | EVQLQQSGPELVKPGASVKISCKTSGYTFTEYTIYW`VKQSHGKSLEWIGGINPNNGDTIYNQNFKGKATLTVDKSSSTAYMELRSLTSEDSAVYYCARDDYGGIAYWGQGTLVTVSA |
| ill | 7-5C4 light chain | DIVMSQSPSSLAVSVGEKVTMSCKSSQSLLYSSNQKNYLAWFQQKPGQSPKLLIYWASTRESGVPDRFTGSGSGTDFTLTISSVKAEDLAVYYCQQYYRYPLTFGAGTKLELK |
| 120 | 7-5D1 heavy chain | QVQLKQSGPGLVQPSQSLSITCTVSGFSLSSYGVHWVRQSPGKGLEWLGVIWSGGSTDYNAAFISRLSISKDNSKSQVFFKMNSLQSNDTAIYYCARGWFSYYFDYWGQGSTLTVSS |
| 121 | 7-5D1 light chain | DMQMTQSPASLSVSVGETVTITCRASENIYSNLAWYQQKQGKSPQLLVYAATNLADGVPSRFSGSGSGTQYSLKINSLQSEDFGSYYCQHFWGNVWTFGGGTKLEIK |
| 122 | 7-5D4 heavy chain | QVQLQQSGAELVKPGASVKMSCKASGYTFSSYSVHWVKQTPGQGLEWIGAIYPGNGDTSYNQNFKAKATLTADESSSTAYMQLRSLTSEDSAVYFCARDGYPYYYALDYWGQGTSVTVSS |

-continued

| SEQ ID NO | Description | | Sequence |
|---|---|---|---|
| 123 | 7-5D4 | light chain | DIVMTQSQKFMSTSVGDRVSVTCKASQNVDTNVAWYQQKPGQSPK PLIYSASYRYSGVPDRFTGGGSGTDFTLTISNVQSEDLAEYFCQQYHR YPWTFGGGTKLEIK |
| 118 | 7-5E2 | heavy chain | EVKLLESGGGLVQPEGSLKLSCAASGFDFSRYWMSWVRQAPGKGL EWIGEINLDSSTINYAPSLEDKFIISRDNAKSTLYLQMSKVRSEDSALY YCAREFYGGSYLDYWGQGTTLTVSS |
| 119 | 7-5E2 | light chain | DIQMTQSPASLSVSVGETVTITCRASDNIYNNLAWYQQKQGKSPQLL VYVATNLADGVPSRFSGSGSGTQYSLKIDSLQSEDFGTYYCQHFWG TPWTFGGGTKLEIK |
| 110 | 7-5F1 | heavy chain | EVQLQQSGPELVKPGASVKISCKTSGYTFTEYTIYWVKQSHGKSLEW IGGINPNNGDTIYNQNFKGKATLTVDKSSSTAYMELRSLTSEDSAVY YCARDDYGGIAYWGQGTLVTVSA |
| 111 | 7-5F1 | light chain | DIVMSQSPSSLAVSVGEKVTMSCKSSQSLLYSSNQKNYLAWFQQKP GQSPKLLIYWASTRESGVPDRFTGSGSGTDFTLTISSVKAEDLAVYY CQQYYRYPLTFGAGTKLELK |
| 124 | 7-5G1 | heavy chain | QVQLQQSGPELVKPGALVKISCKASGYTFTSYDISWVKQRPGQGLE WIGWIYPGDGSTEYNEKFKAKATLTADKSSSTAYMQLSSLTSENSA VYFCARRATTPTGYALDYWGQGTSVTVSS |
| 125 | 7-5G1 | light chain | DIQMTQSPASLSVSVGETVTITCRASENIYSNLAWYQQKHGKSPQLL VYGAINLADGVPSRFTGSGSDTQYSLKINSLQSEDFGNYYCQHFWDI PWTFGGGTKLESK |
| 110 | 7-5H3 | heavy chain | EVQLQQSGPELVKPGASVKISCKTSGYTFTEYTIYWVKQSHGKSLEW IGGINPNNGDTIYNQNFKGKATLTVDKSSSTAYMELRSLTSEDSAVY YCARDDYGGIAYWGQGTLVTVSA |
| 111 | 7-5H3 | light chain | DIVMSQSPSSLAVSVGEKVTMSCKSSQSLLYSSNQKNYLAWFQQKP GQSPKLLIYWASTRESGVPDRFTGSGSGTDFTLTISSVKAEDLAVYY CQQYYRYPLTFGAGTKLELK |

This disclosure also includes the following CDR sequences:

| mAb | heavy chain | | | light chain | | |
|---|---|---|---|---|---|---|
| clone | CDR1 | CDR2 | CDR3 | CDR1 | CDR2 | CDR3 |
| 3C4, 3E4 | GFNIKDTY (SEQ ID NO: 126) | IDPASGKT (SEQ ID NO: 134) | CASGYDVNYELDYW (SEQ ID NO: 146) | QNINVW (SEQ ID NO: 161) | KAS | CQQGQSYPYTF (SEQ ID NO: 174) |
| 3G1 | GFSLTSYG (SEQ ID NO: 127) | IWSGGST (SEQ ID NO: 135) | CAKYRYDSFAYW (SEQ ID NO: 147) | KSVSTSGYSY (SEQ ID NO: 162) | LAS | CQHSRELPYTF (SEQ ID NO: 175) |
| 3A6 | GFSLISYG (SEQ ID NO: 128) | IWAGGST (SEQ ID NO: 136) | CGRDYGILLIDYW (SEQ ID NO: 148) | SSVSY (SEQ ID NO: 163) | DTS | CFQGSGYPFTF (SEQ ID NO: 176) |
| 3B3 | GYSITSDYA (SEQ ID NO: 129) | ISYSGTT (SEQ ID NO: 137) | CAGRRGAYYGNYEEDY W (SEQ ID NO: 149) | SIVNY (SEQ ID NO: 164) | DTS | CQQWSSYPYTF (SEQ ID NO: 177) |
| 3D7 | GFNIKDTY (SEQ ID NO: 126) | IDPANGNS (SEQ ID NO: 138) | CARSYYDYDGGGCFDY W (SEQ ID NO: 150) | QSVSND (SEQ ID NO: 165) | YAS | CQQGYSSPLTF (SEQ ID NO: 178) |
| 3E5 | GYSFTGYF (SEQ ID NO: 130) | INPYNGDT (SEQ ID NO: 139) | CGLRTYW (SEQ ID NO: 151) | QDINNN (SEQ ID NO: 166) | HGT | CVQSVQFPYTF (SEQ ID NO: 179) |
| 3B4 | GFNIKDTY (SEQ ID NO: 126) | IDPANGDT (SEQ ID NO: 140) | CARSYYYGTTSWFASW (SEQ ID NO: 152) | EDIYNH (SEQ ID NO: 167) | GAP | CQQYWSTPYTF (SEQ ID NO: 180) |

-continued

| mAb | heavy chain | | | light chain | | |
|---|---|---|---|---|---|---|
| clone | CDR1 | CDR2 | CDR3 | CDR1 | CDR2 | CDR3 |
| 3D1 | GFNIKDTY (SEQ ID NO: 126) | IDPANGNT (SEQ ID NO: 141) | CARWDFGNYVDYAMD YW(SEQ ID NO: 153) | QDLYSF (SEQ ID NO: 168) | RAN | CLQYDAFPWTF (SEQ ID NO: 181) |
| 3A2 | GFSLSTSGMG (SEQ ID NO: 131) | IYWDDDK (SEQ ID NO: 142) | CARRGPLITTDGTFDVW (SEQ ID NO: 154) | QDVGTS (SEQ ID NO: 169) | WAS | CQQYSSYPYTF (SEQ ID NO: 182) |
| 3C6 | GFSLSTSGMG (SEQ ID NO: 131) | IYWDDDK (SEQ ID NO: 142) | CARRGPLITTDGTFDVW (SEQ ID NO: 154) | QDVDTA (SEQ ID NO: 170) | WAS | CQQYSSYPYTF (SEQ ID NO: 182) |
| 3H5 | GYSFTGYF (SEQ ID NO: 130) | INPYNGDT (SEQ ID NO: 139) | CGRGLYGKGYYYAMD YW(SEQ ID NO: 155) | QSLLYSSNQK NY (SEQ ID NO: 171) | WAS | CQQYYSYPWTF (SEQ ID NO: 183) |
| 3G7 | GYSFTSYW (SEQ ID NO: 132) | IHPSDSET (SEQ ID NO: 143) | CARSSGYDWYFDVW (SEQ ID NO: 156) | ESVDSYGNSF (SEQ ID NO: 172) | RAS | CQQSNEDPWTF (SEQ ID NO: 184) |
| 3A7 | GFSLSTSGMG (SEQ ID NO: 131) | IYWDDDK (SEQ ID NO: 142) | CARRGPLITTDGTFDVW (SEQ ID NO: 154) | QDVGTS (SEQ ID NO: 169) | WAS | CQQYSSYPYTF (SEQ ID NO: 182) |
| 3C2 | GYAFTSYW (SEQ ID NO: 133) | IYPGDGAT (SEQ ID NO: 144) | CARSGGYDWYFDVW (SEQ ID NO: 157) | ETVDSYGNSF (SEQ ID NO: 173) | RAS | CQQSNEDPWTF (SEQ ID NO: 184) |
| 3D5 | GFNIKDTY (SEQ ID NO: 126) | IDPANGNT (SEQ ID NO: 141) | CTRYYYGSSGFFDVW (SEQ ID NO: 158) | QSVSND (SEQ ID NO: 165) | YAS | CQQDYSSPTF (SEQ ID NO: 185) |
| 3F6 | GFNIKDTY (SEQ ID NO: 126) | IDPASGNT (SEQ ID NO: 145) | CARSYYTYDGFFDVW (SEQ ID NO: 159) | QSVSND (SEQ ID NO: 165) | YAS | CQQDYSSPPTF (SEQ ID NO: 186) |
| 9F2 | GFNIKDTY (SEQ ID NO: 126) | IDPANGNT (SEQ ID NO: 141) | CARTYYYGSSYEAMDY W (SEQ ID NO: 160) | QSVSND (SEQ ID NO: 165) | YAS | CQQDYSSPTF (SEQ ID NO: 185) |

Antibodies 3A2 and 3A7 (and probably others in this panel) bind an epitope located in the S11 RBD with high affinity. Antibodies 3G7, 3F1, and 3H46 likely neutralize viral infectivity based on targeting of a different epitope.

In vitro RBD/hACE2 binding enhancement, and the ability to stain virus in heat-treated histological samples but not heat-inactivated virus, as well as binning and sequence data tell us that mAbs 3D2 and 3D7 bind another epitope that may only be exposed after extreme degradation and that might serve as target to be avoided due to potential antibody-dependent enhancement of infectivity.

An important embodiment of this IP is the creation of "cooperative pairs" of antibodies, defined as those that can simultaneously bind the same SARS-CoV-2 spike protein with high affinity. These pairs are especially useful for diagnostic detection of the virus, because they will not interfere with each other in sandwich-type assays. An example of these pairs are 3A7 and 3D7; 3A7 and 3F2.

1. Human and Humanized Antibodies

In some embodiments, the antibodies are humanized antibodies. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', $F(ab')_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all, of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a nonhuman antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

The antibody can be bound to a substrate or labeled with a detectable moiety or both bound and labeled. The detectable moieties contemplated with the present compositions include fluorescent, enzymatic and radioactive markers.

2. Single-Chain Antibodies

In some embodiments, the antibodies are single-chain antibodies. Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

3. Monovalent Antibodies

In some embodiments, the antibodies are monovalent antibodies. In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the $F(ab')_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The $F(ab')_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

4. Hybrid Antibodies

In some embodiments, the antibodies are hybrid antibodies. In hybrid antibodies, one heavy and light chain pair is homologous to that found in an antibody raised against one epitope, while the other heavy and light chain pair is homologous to a pair found in an antibody raised against another epitope. This results in the property of multifunctional valency, i.e., ability to bind at least two different epitopes simultaneously. Such hybrids can be formed by fusion of hybridomas producing the respective component antibodies, or by recombinant techniques. Such hybrids may, of course, also be formed using chimeric chains.

5. Conjugates or Fusions of Antibody Fragments

In some embodiments, the antibodies are conjugates or fusions of antibody fragments. The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor, Monrovia, CA). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

B. Pharmaceutical Compositions

Pharmaceutical compositions including the disclosed antibodies or antigen binding fragments are provided. Pharmaceutical compositions containing the antibodies or antigen binding fragments can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g, age, immune system health, etc.), the disease, and the treatment being affected.

For the disclosed antibodies or antigen binding fragments, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed antibodies or antigen binding fragments, generally dosage levels of 0.001 to 20 mg/kg of body weight daily are administered to mammals. Generally, for intravenous injection or infusion, dosage may be lower.

In certain embodiments, the antibodies or antigen binding fragments is administered locally, for example by injection directly into a site to be treated. Typically, the injection causes an increased localized concentration of the antibodies or antigen binding fragments composition which is greater than that which can be achieved by systemic administration. The antibodies or antigen binding fragments compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical Administration

The disclosed antibodies or antigen binding fragments can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology.

Transdermal formulations may require the inclusion of penetration enhancers.

3. Controlled Delivery Polymeric Matrices

The antibodies or antigen binding fragments disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release,* 5:13-22 (1987); Mathiowitz, et al., *Reactive Polymers,* 6:275-283 (1987); and Mathiowitz, et al., *J. Appl. Polymer Sci.,* 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Manufacture

A. Methods of Making Antibodies

The disclosed antibodies can be generated in cell culture, in phage, or in various animals, including but not limited to cows, rabbits, goats, mice, rats, hamsters, guinea pigs, sheep, dogs, cats, monkeys, chimpanzees, and apes. Therefore, in one embodiment, an antibody is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles And Practice* (Academic Press, 1993); *Current Protocols In Immunology* (John Wiley & Sons, most recent edition).

The disclosed antibodies can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., *Mol. Immunol.* 30:105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to proteins, polypeptides, or fusion proteins of SARS-CoV-2. See, e.g., *Antibody Engineering: A Practical Approach* (Oxford University Press, 1996).

For example, suitable antibodies with the desired biologic activities can be identified using in vitro assays including but not limited to: proliferation, migration, adhesion, soft agar growth, angiogenesis, cell-cell communication, apoptosis, transport, signal transduction, and in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic peptide. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A monoclonal antibody is obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

Antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

Methods of making antibodies using protein chemistry are also known in the art. One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, CA). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo as described above. Once isolated, these independent peptides or polypeptides may be linked to form an antibody or antigen binding fragment thereof via similar peptide condensation reactions.

For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method consists of a two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

IV. Method of Use

The disclosed antibodies and antigen binding fragments bind to SARS-CoV-2 spike protein and are useful in the detection, diagnosis, and treatment during active COVID-19 infection. In one embodiment, the antibodies are SARS-CoV-2-specific and can be used to detect and diagnose infection with SARS-CoV-2.

In another embodiment, the antibodies are strongly reactive with both SARS-CoV-1 and SARS-CoV-2 and can be used to detect and diagnose infection with SARS-CoV-1 and SARS-CoV-2.

The antibodies can inhibit, reduce or prevent the binding of coronaviruses, including but not limited to SARS-CoV-2 spike protein to cell surface proteins in a subject. In some embodiments, the disclosed antibodies and antigen-binding fragments thereof reduce or inhibit the growth or proliferation of or induce the death of a cell infected with a coronavirus to which they bind.

A. Treating Coronavirus

One embodiment provides a method for treating coronavirus infection in a subject in need thereof by administering to the subject any one of the disclosed antibody or antigen-binding fragments thereof in an amount effective to treat the coronavirus infection. The infection can be SARS-CoV-1 or SARS-CoV-2.

The infection can be acute or chronic. An acute infection is typically an infection of short duration. During an acute infection, immune cells begin expressing immunomodulatory receptors. Accordingly, in some embodiments, the method includes increasing an immune stimulatory response against an acute infection.

Another embodiment provides a method for inhibiting the production of additional viral particles in a SARS-CoV-2- infected cell, wherein the growth of the SARS-CoV-2 infected cell is at least in part dependent upon the expression of a SARS-CoV-2 spike protein (wherein the SARS-CoV-2 spike protein may be expressed either within the infected cell itself or a cell that produces polypeptide(s) that have a growth potentiating effect on the infected cells), by contacting the SARS-CoV-2 spike protein with an antibody that binds to the SARS-CoV-2 spike protein, thereby antagonizing the growth-potentiating activity of the SARS-CoV-2 spike protein and, in turn, inhibiting the growth of the infected cell. Preferably the growth of the infected cell is completely inhibited. More preferably, binding of the antibody to the SARS-CoV-2 spike protein induces the death of the infected cell.

In some embodiments, the disclosed antibodies are used to prevent coronavirus infection in subjects that are at a high risk for coronavirus infection. Exemplary at-risk subjects include but are not limited to immunocompromised individuals, children, the elderly, or subjects with diabetes, obesity, asthma, heart disease, lung disease, cancer, or coronary disease. In one embodiment, high-risk subjects are prophylactically administered the disclosed antibodies in an amount effective to prevent coronavirus infection should they be exposed.

B. Detecting and diagnosing coronavirus Another embodiment provides a method of determining the presence of a SARS-CoV-2 spike protein in a sample suspected of containing the SARS-CoV-2 spike protein, by exposing the sample to an antibody that binds to the SARS-CoV-2 spike protein and determining binding of the antibody to the SARS-CoV-2 spike protein in the sample, wherein the presence of such binding is indicative of the presence of the SARS-CoV-2 spike protein in the sample. Optionally, the sample may contain cells (which may be fibroblasts, epithelial cells, mucosal cells, and the like) suspected of expressing the SARS-CoV-2 spike protein. The antibody employed in these methods may optionally be detectably labeled, attached to a solid support, or the like.

This disclosure is further directed to mAbs and related binding proteins that bind specifically to the spike protein of the SARS-CoV-2 virus and to the use of those mAbs and related binding proteins in epitope blocking ELISAs. Thus, one embodiment provides methods for detecting SARS-CoV-2 virus spike protein in a biological sample by contacting the sample with an antigen which contains an epitope of a spike protein and determining whether an antibody in the sample binds to the epitope. Preferably the binding determination is made in an epitope blocking ELISA. These methods thereby provide highly sensitive and specific epitope blocking ELISAs (EB ELISA) for detecting SARS-CoV-2 spike subtypes.

A further embodiment provides a method of diagnosing the presence of a SARS-CoV-2 infection in a mammal, by detecting the level of expression of a gene encoding a SARS-CoV-2 spike protein in a test sample of tissue cells obtained from the mammal, wherein detection of expression of the SARS-CoV-2 spike protein in the test sample is indicative of the presence of SARS-CoV-2 infection in the mammal from which the test sample was obtained.

Another embodiment provides a method of binding an antibody to a cell that expresses a SARS-CoV-2 spike protein, by contacting a cell that expresses a SARS-CoV-2 spike protein with the antibody of this disclosure under conditions which are suitable for binding of the antibody to the SARS-CoV-2 spike protein and allowing binding therebetween. In preferred embodiments, the antibody is labeled with a molecule or compound that is useful for qualitatively and/or quantitatively determining the location and/or amount of binding of the antibody to the cell.

Other embodiments of this disclosure include the use of a SARS-CoV-2 spike protein, a nucleic acid encoding a SARS-CoV-2 spike protein, or a vector or host cell comprising that nucleic acid, or an anti-SARS-CoV-2 spike protein antibody in the preparation of a medicament useful for (i) the therapeutic treatment or diagnostic detection of a SARS-CoV-2 infection, or (ii) the therapeutic treatment or prevention of a SARS-CoV-2 infection-related disorder.

Yet another embodiment provides a method of therapeutically treating a viral infection in a mammal, wherein the infection is at least in part dependent upon the expression of a SARS-CoV-2 spike protein, by administering to the mammal a therapeutically effective amount of an antibody or antigen-binding fragment thereof that binds to the SARS-CoV-2 spike protein, thereby antagonizing the activity of the SARS-CoV-2 spike protein and resulting in the effective therapeutic treatment of the infection in the mammal. Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells or bacterial cells.

One embodiment provides a bispecific antibody that binds to SARS-CoV-2 spike protein and a cell-surface protein of an immune cell. The immune cell can be a T cell, for example a cytotoxic T cell, a macrophage, a dendritic cell, or a neutrophil.

Immunoassays were developed using optimal mAb pairings with high sensitivity for spike protein, viral culture supernatant, and infected tissue samples. Thus, the mAbs of this disclosure are capable of recognizing spike protein in a variety of environments with potential uses in immunoassay development and as immunodiagnostic reagents for clinical sample and tissue confirmation of SASRS-CoV-2.

In another embodiment, the disclosed antibodies and antigen-binding fragments thereof are detectably labeled, attached to a solid support, or the like, such as a lateral flow assay device which provides for point-of-care detection of SARS-CoV-2 and/or diagnosis.

V. Combination Therapies

The antibodies or antigen binding fragments disclosed herein can be administered to a subject in need thereof alone or in combination with one or more additional therapeutic agents. In some embodiments, the antibodies or antigen binding fragments and the additional therapeutic agent are administered separately, but simultaneously. The antibodies or antigen binding fragments and the additional therapeutic agent can also be administered as part of the same composition. In other embodiments, the antibodies or antigen binding fragments and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6, 7, 14, 21, 28, 35, or 48 days prior to a first administration of second agent. The disclosed antibodies or antigen binding fragments can be the first or the second therapeutic agent.

The antibodies or antigen binding fragments and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules include, but are not limited to, cytokines, chemotherapeutic agents, radionuclides, other immunotherapeutic, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the disclosed antibodies or antigen binding fragments can be co-administered with one or more additional agents that function to enhance or promote an immune response or reduce or inhibit an immune response.

VI. Kits

The disclosed antibodies and antigen binding fragments can be packaged in a hermetically sealed container, such as an ampoule or sachet, indicating the quantity. The agent can be supplied as a dry sterilized lyophilized powder or water free concentrate in a hermetically sealed container and can be reconstituted, e.g., with water or saline to the appropriate concentration for administration to a subject. For example, the agent can be supplied as a dry sterile lyophilized powder in a hermetically sealed container at a unit dosage of at least 5 mg, or at least 10 mg, at least 15 mg, at least 25 mg, at least 35 mg, at least 45 mg, at least 50 mg, or at least 75 mg. The lyophilized agent can be stored at between 2 and 8° C. in their original container and are typically administered within 12 hours, or within 6 hours, or within 5 hours, or within 3 hours, or within 1 hour after being reconstituted.

In an alternative embodiment, agent can be supplied in liquid form in a hermetically sealed container indicating the quantity and concentration. In some embodiments, the liquid form of the agent supplied in a hermetically sealed container including at least 1 mg/ml, or at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml of the agent.

Pharmaceutical packs and kits including one or more containers filled with agent are also provided. Additionally, one or more other prophylactic or therapeutic agents useful for the treatment of a disease can also be included in the pharmaceutical pack or kit. The pharmaceutical pack or kit can also include one or more containers filled with one or more of the ingredients of the disclosed pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

Kits designed for the above-described methods are also provided. Embodiments typically include one or more of the disclosed antibodies and antigen binding fragments. In particular embodiments, a kit also includes one or more other prophylactic or therapeutic agents useful for the treatment of cancer, in one or more containers. In other embodiments, a kit also includes one or more anti-inflammatory agents useful for the treatment inflammatory and autoimmune diseases, in one or more containers.

EXAMPLES

Figure 1D:
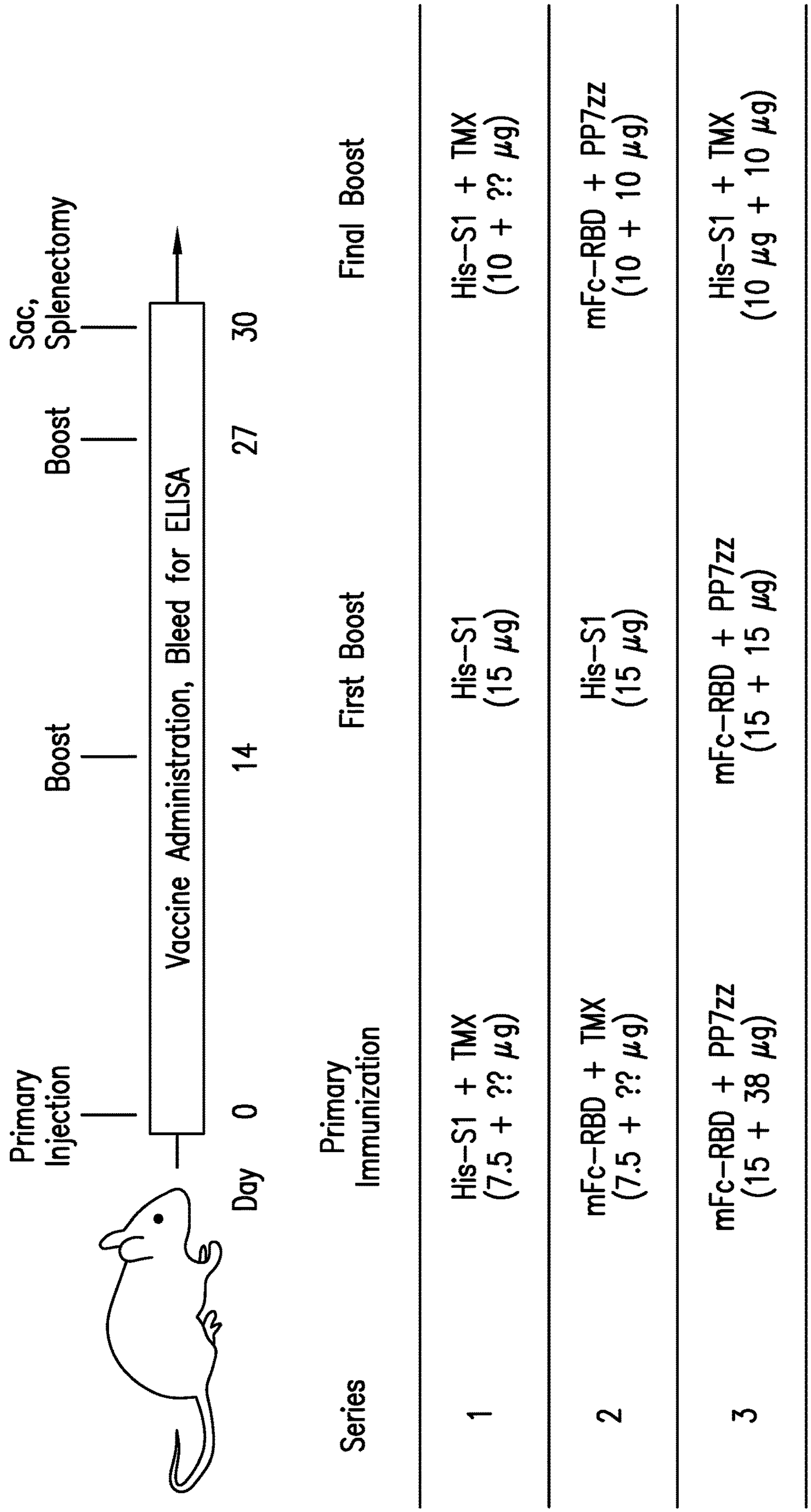
FIG. 1D is a schematic showing the vaccine schedule and strategy.
Figure 1E:
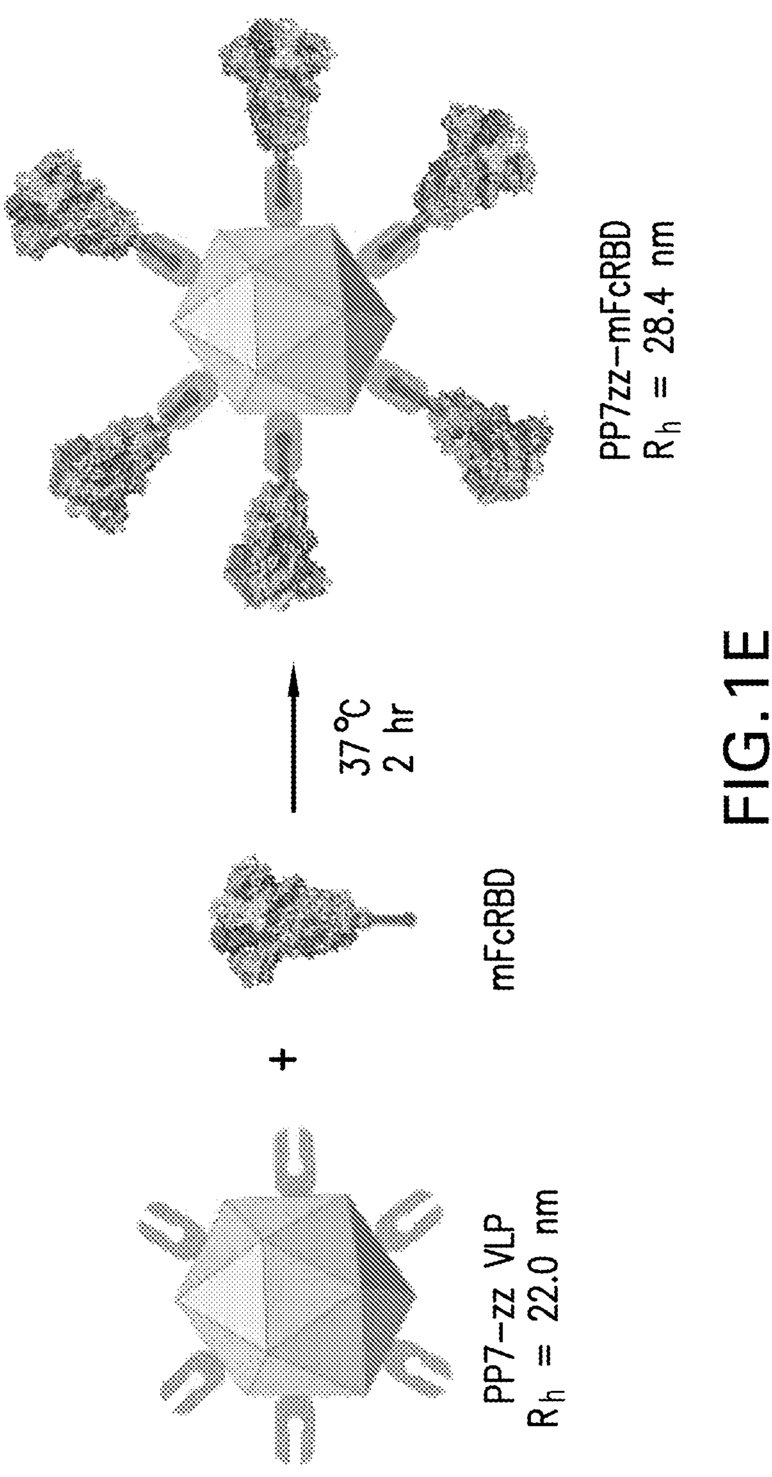
FIG. 1E shows the VLP display of Fc-tagged antigens using the PP7 particle displaying 120 ZZ-domains per particle; a 1:1 mass ratio of mFc-S1 and VLP provides a Fc:ZZ molar ratio of 0.82. Rh=hydrodynamic radius measured by dynamic light scattering in phosphate buffer.

Example 1. SARS-CoV-2 Spike Protein Subunit Vaccine Strategy and Humoral Immune Response in Mice In order to target the key S1 RBD of SARS-CoV-2, three polypeptide variations of this motif were employed: a commercially available S1 domain (residues 1-685) with C-terminal hexahistidine tag (Sino Biological, designated His-S1), a commercial RBD sequence (residues 319-541) (Wang, Q. H. et al. *Cell* 2020, 181, 894-904). fused at the C-terminus with a mouse IgG1 Fc domain (Sino Biological, designated mFc-RBD), and the noncovalent complex of mFc-RBD with the PP7 bacteriophage virus-like particle (VLP) engineered to express two sequential Fc-binding Z-domains at 120 places on the VLP exterior surface (Zhao, L., et al. *ACS Nano* 2019, 13, 4443-4454). The last species provides a large (FIG. 1E) polyvalent display of RBD domains which could productively engage immune cells and stimulate affinity maturation. The use of Fc-tagged antigens is well known to increase antigen uptake and processing, (Levin, D. et al. *Trends Biotechnol.* 2015, 33, 27-34) including many examples with viral antigens (Liu, C. et al. *J. Clin. Invest.* 1996, 98, 2001-2007; He, Y. et al. *Biochemical and Biophysical Research Communications* 2004, 324, 773-781; Lu, L., et al. *J. Virol.* 2011, 85, 10542-10553; Loureiro, S. et al. *Journal of Virology* 2011, 85, 3010-3014; Konduru, K. et al., *The Journal of Immunology* 2013, 190, 205.218-205.218). While the virus-like particles used here are regarded as self-adjuvanting, (Bachmann, M. F. et al. *Nat. Rev. Immunol.* 2010, 10, 787-796; Mohsen, M. O. et al. *Vaccines* 2018, 6, 37) the recombinant S1 and RBD proteins were usually augmented by TiterMax Gold emulsion adjuvant.

Figure 1F:
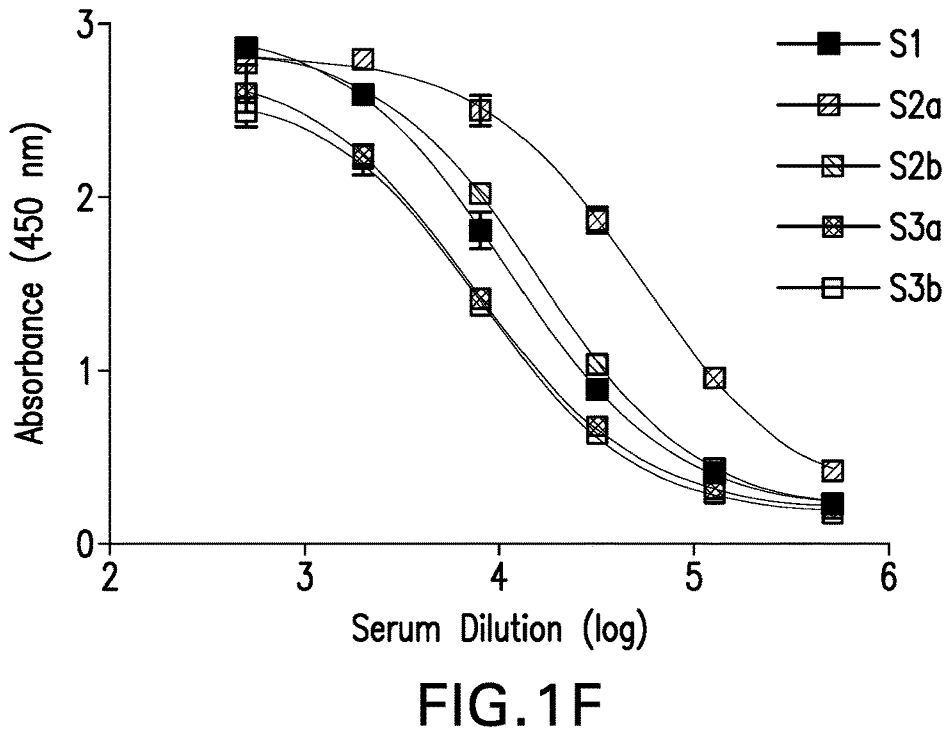
FIG. 1F is a line graph showing ELISA responses for serum dilutions against plated His-S1 protein from the sacrificed mice at day 30.
Figure 1G:
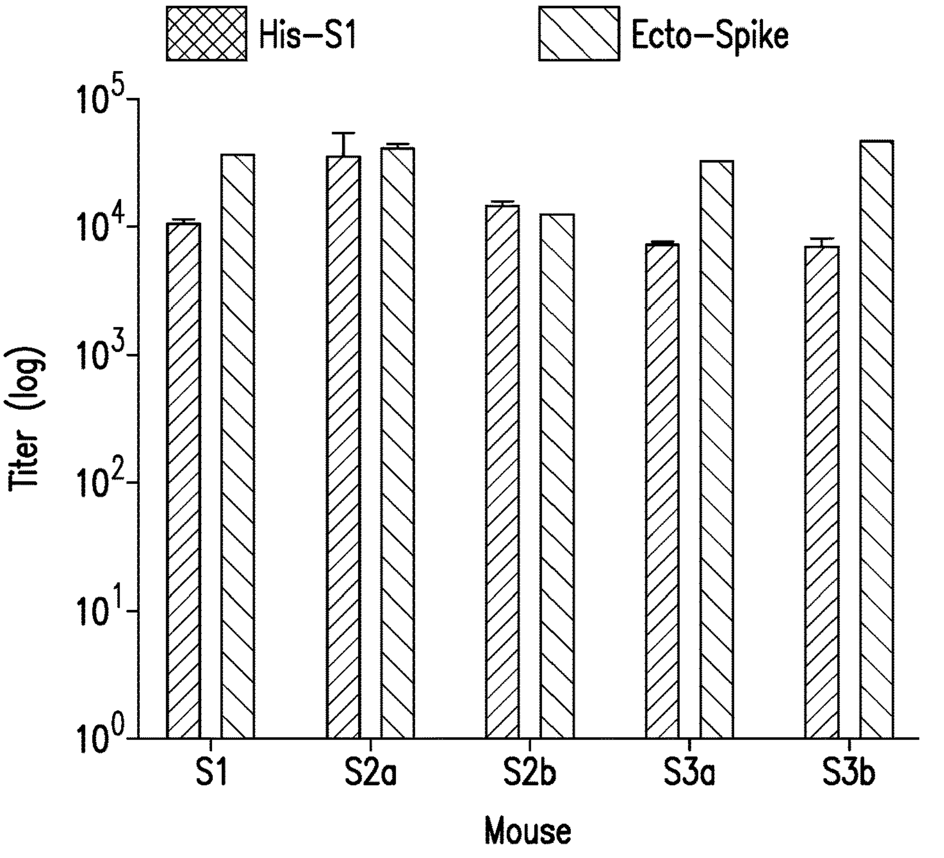
FIG. 1G is a line graph showing titer values from ELISA analysis as in panel d, against plated His-S1 or spike ectodomain protein. S1, S2, and S3 designate immunization series in panel b; a and b designate different mice.

Three vaccination procedures with Balb/c mice (FIG. 1D) were employed and characterized by the use of only the recombinant His-S1 domain (Series 1), a combination of all three immunogens beginning with mFc-RBD (Series 2), and the VLP-displayed mFc-RBD with a final focusing boost of His-S1 (Series 3). Six-week old female Balb/c mice (n=3 per group) were immunized with primary antigen and adjuvant on day 0 followed by boosts on days 14 and 27. Blood was collected for ELISA on days 0, 14, 30. The timing of boost injections (days 14 and 27) and harvesting of splenocytes (day 30) was considerably compressed from normal practice, and individual mice or pairs of mice were chosen for maximum immune response, rather than larger cohorts as one would use to determine reproducibility and mechanistic trends. Representative serum antibody titers, shown in FIG. 1F-1G, were found to be in a range indicating robust antibody development, as often observed in more classical hybridoma vaccine strategies requiring 6 weeks or more.

Figure 2A:
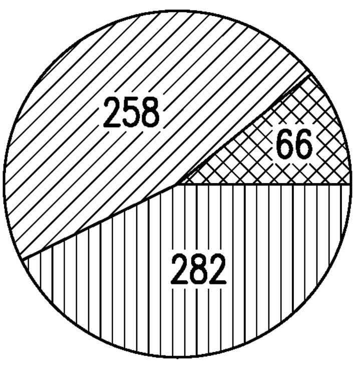
FIG. 2A is a pie chart showing total number of IgG-secreting hybridomas chosen from Series 1-3 immunization schedules.

Example 2. Characterization of Anti-SARS-CoV-2 Hybridoma Clones and Monoclonal Antibodies Following proof of anti-spike seroreactivity, 5-20 million splenocytes were harvested from each mouse on day 30 and subjected to myeloma fusion. The resulting hybridomas were distributed in 3D culture and selected by robotic probe based on high IgG secretion as evidenced by FITC signal from anti-IgG secondary antibody distributed through the culture medium (FIG. 2A). Series 3 mice (immunized and boosted with VLP-displayed mFc-RBD) provided relatively few high-secreting hybridomas. Supernatants from all of the selected clones were then screened by ELISA against recombinant His-S1 polypeptide and a SARS-CoV-2 spike ectodomain protein which exists primarily as a noncovalent trimer, thought to better represent the native structure of the viral spike (FIG. 1A) (Walls, A. C. et al, *Cell* 2020, 181, 281-292.e286; Wrapp, D et al. *Science* 2020, 367, 1260-1263).

Figure 2B:
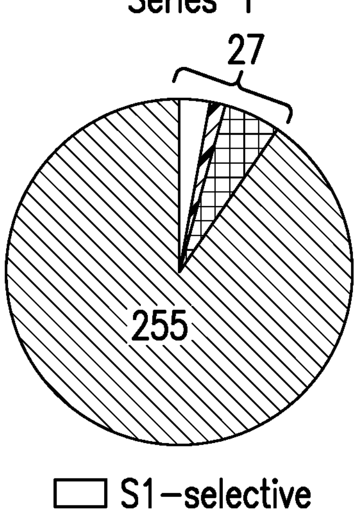
FIGS. 2B-2D are pie charts showing antigen specificity of antibody binding from the selected clones.
Figure 2C:
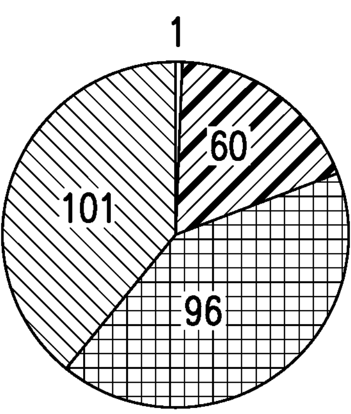
Figure 2D:
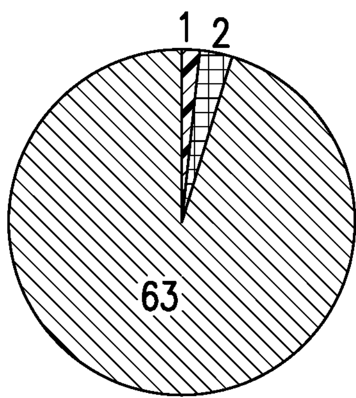

As shown in FIGS. 2B-2D, Series 2 (starting with mFc-RBD immunization) produced a far greater proportion of spike-binding antibodies than the other protocols, consistent with an overall superior immune response to the target antigen. In addition, Series 2 clones featured a significantly higher fraction of antibodies (38%) exhibiting strong binding to the plated ectodomain alone, with the rest binding approximately as well to both His-S1 and the ectodomain trimer. Only one of these (0.6%) selectively bound the His-tagged S1 protein. As none of the Series 2 immunization or boost injections contained the S2 subunit, these results suggested strong recognition of virus-relevant conformations or exposed epitopes in S1. The 157 spike-binding hybridomas from Series 2 were chosen to move forward.

Figure 2E:
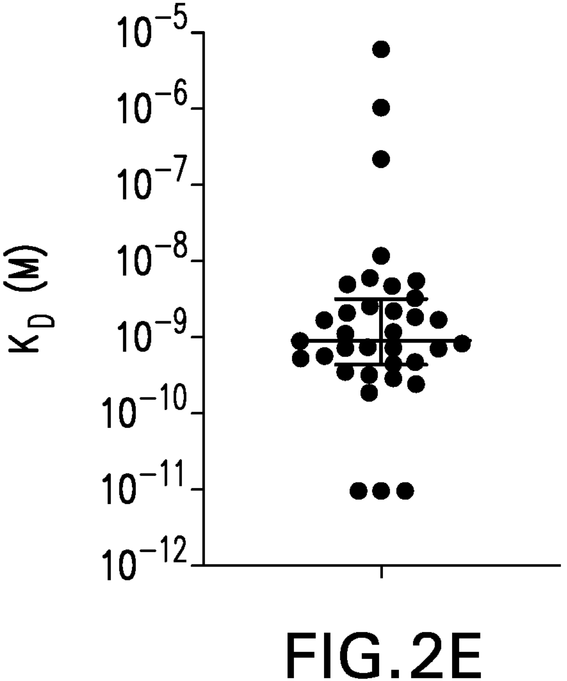
FIG. 2E is a scatter plot showing distribution of affinities of the 37 selected clones as measured by BLI.

The quantitative binding avidities of each of these 157 mAbs (reported here as the inverse of the observed adsorption constant, $1/K_{ads}$ to immobilized spike ectodomain) were determined by biolayer interferometry (BLI). From this panel, three antibodies (3H6, 3A7, 3G7) exhibited apparent dissociation constants of approximately 10 pM due to unusually slow off-rates. Thirty antibodies in total showed avidities by this assay of 6 nanomolar or better (FIG. 2E) and were taken forward for further characterization and functional testing. The majority of these antibodies were found to be IgG1 (k light chain). Overall, from an initial pool of more than 55 million B cells, we ultimately arrived at 37 clones with highly potent anti-SARS-CoV-2 characteristics, which were then produced in larger quantities for further testing.

The vast majority (33 out of 37) of these high-affinity antibodies bound both recombinant S1 subunit and ectodomain trimers, as determined by ELISA using plated antigen; only 3H6, 3G7, 3C3, and 3B1 showed a distinct preference for the ectodomain. Limits of detection for recombinant ectodomain by ELISA were determined by dilution of the spike protein concentration used to coat the microtiter well plate, followed by washing and exposure to a fixed concentration (1 μg/mL) of purified monoclonal antibody. The data fitted well in each case to a standard adsorption titration curve, providing a sensitivity estimate designated as $AC_{50}$ (half-maximal adsorbent concentration). The results were remarkably consistent, in which $AC_{50}$ varied between 90 and 210 ng/mL for all but two mAbs (3C3, 3H5).

Example 3. Functional Utility of SARS-CoV-2 mAbs

The ability of the selected mAbs to inhibit or increase the binding of the SARS-CoV-2 RBD to the human ACE2 receptor was assessed with a direct split-luciferase reporter of the RBD-ACE2 interaction. Antibody-promoted ACE2 binding is associated with the important phenomenon of antibody-dependent enhancement (ACE) of coronavirus infectivity (Yang, Z. et al, *Proc. Natl. Acad. Sci. U.S.A.* 2005, 102, 797-801; Walls, A. C. et al. *Nat. Struct. Mol. Biol.* 2016, 23, 899-905; Wan, Y. et al. *J. Virol.* 2020, 94, e2015-2019). This is thought to result either from direct stabilization or conformational advantage conferred upon the S1 RBD by a targeting antibody, or by mAb Fc domain interaction with Fcg receptors that assist viral entry; the assay used here is relevant to the former mechanism. Ten of 32 mAbs tested were found to inhibit RBD-hACE2 binding in dose-dependent fashion (FIG. 3A-3B), seven of these (3A2, 3F2, 3H2, 3B3, 3F5, 3A7, and 5B1) defined as potent (>80% inhibition). Nine mAbs with varying levels of RBD/hACE2 binding enhancement (3B4, 3C4, 3E4, 3B6, 3F6, 3G6, 3D7, 9B1 and 9F2) were also identified, and 16 with little or no effect on this interaction. By switching the RBD-luciferase antigen from SARS2 to SARS1, mAb cross-reactivity between the two coronaviruses was assessed, and it was discovered that most of the antibodies inhibited ACE2 receptor engagement by both SARS-CoV variants.

Figure 3A:
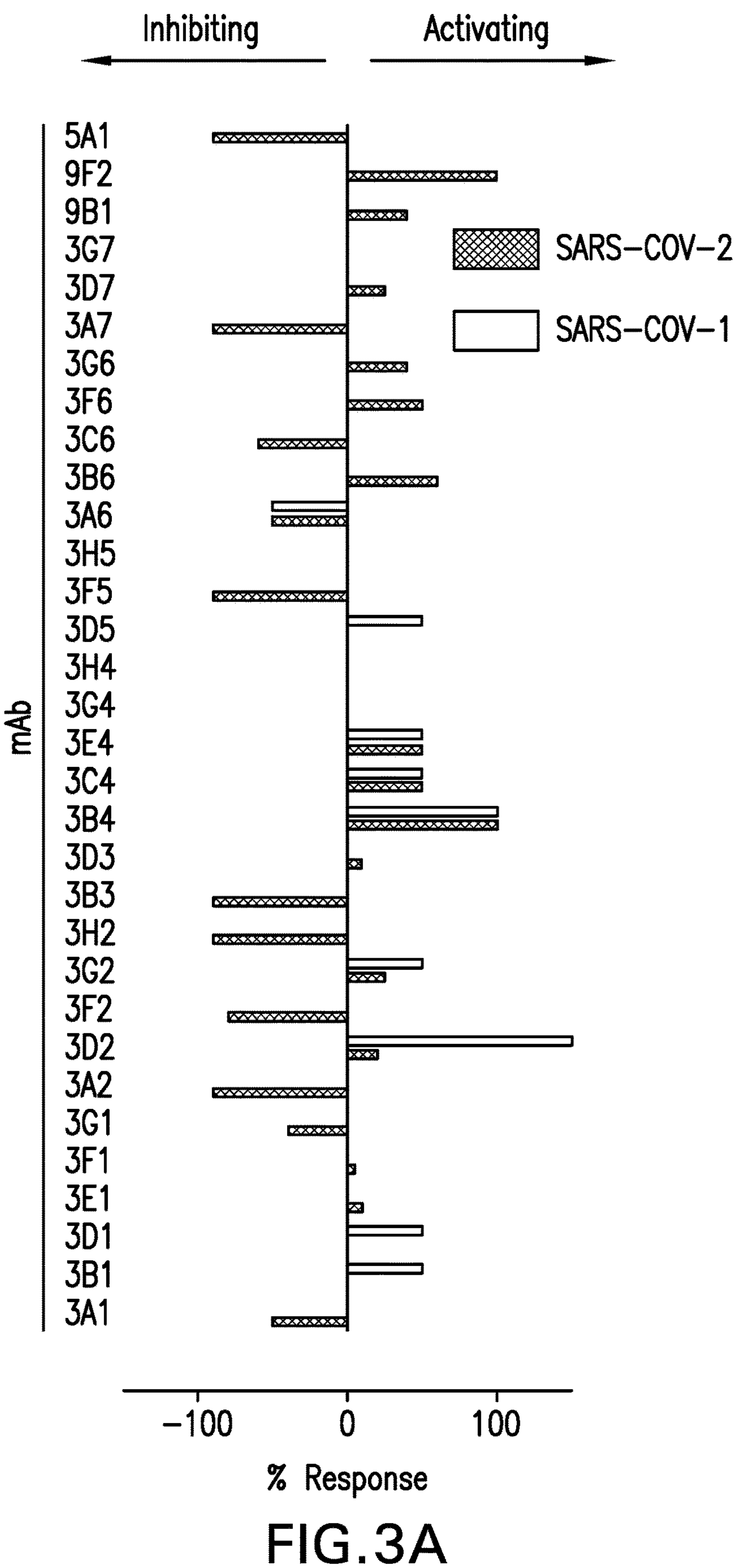

The ability of a subset of these antibodies to neutralize SARS-CoV-2 infectivity was assessed in vitro by two assays in which infectious SARS-CoV-2 was pre-mixed with varying concentrations of antibody, followed by passage in cultured mammalian cells. Initial screening was performed with a GFP reporter variant of the virus and Vero E6 cells (two days viral passage). An early patient isolate (SARS-CoV-2-WA P #4) was used and passaged for five days in cell culture. The clinical isolate proved to be far more sensitive to antibody, but the trends in the two assays were very similar. Eight antibodies were found to be strongly neutralizing under these conditions (3F5, 3B3, 3A7, 3A2, 3C2, 3H2, 3D3, 3F2), with neutralization titers ranging from 24 to 98 ng/mL in the second assay (FIG. 3C). Antibody 3F5 proved uniquely active, far outperforming the others with the GFP reporter strain and being the most potent (with 3B3) against the WA strain. Seven of the top eight antibodies (excepting only 3D3) also comprised the cohort that most strongly inhibited RBD-ACE2 binding (FIG. 3A). Seven antibodies were found to bind to a detectable degree to a synthetic biotinylated 15-mer peptide of the receptor binding motif covering amino acids 486-501, which contains four out of five key RBD-hACE2 contact residues (FIG. 3D) (Shang, J. et al, *Nature* 2020, 581, 221-224; Wan, Y.; et al. *J Virol.* 2020, 94, e00127-00120). These data therefore suggest that neutralization is associated with binding of the SARS-CoV-2 RBD domain, as for other neutralizing human antibodies recently reported. (Liu, L.; et al., *bioRxiv* 2020)

An important diagnostic application of mAbs is their use as immunohistochemical staining reagents for the analysis of potentially infected tissue. Most such histological samples are subjected to severe treatment involving fixation (protein crosslinking or embedding in a matrix) and heating just prior to analysis to expose antigen at the sample surface. The epitopes available in these materials may bear little relationship to those present on the active virus, and so independent testing of mAb candidates is required. Among the high-affinity mAb panel, two were identified, 3D2 and 3D7, that preferentially stained SARS-CoV-2 viral particles in lung tissue from infected patients (FIG. 3E). Interestingly, these clones appear to have functional characteristics opposite to those desired of a therapeutic molecule: they exhibited no detectable neutralization activity and enhanced binding of spike protein to the ACE2 receptor.

Example 4. Epitope Binding Patterns

The relative binding sites of a randomly chosen subset of 14 antibodies were assessed by competitive ELISA against plated spike ectodomain, summarized in FIG. 4. In this experiment, low signal is presumed to result from competitive binding to the same or allosterically related epitopes, as illustrated by the uniformly low values on the diagonal. The results cluster into four major groups, which correlate to a significant degree with functional performance. Thus, the strong neutralizers tested here are found exclusively in groups 1 and 3. Group 1 also contains tighter binders overall, with average $1/K_{ads}$=0.36 nM, compared to an average of 3.2 nM for the other groups. Antibodies in groups 2 and 4 were uniformly activators of spike-ACE2 binding (FIG. 3A), whereas groups 1 and 3 were almost exclusively (except for 3G7) inhibitors of that interaction. These unbiased correlations strongly support the assumption that binding site determines function.

Example 5. Amino Acid Sequence Similarities of Selected Clones

Figure 5A:
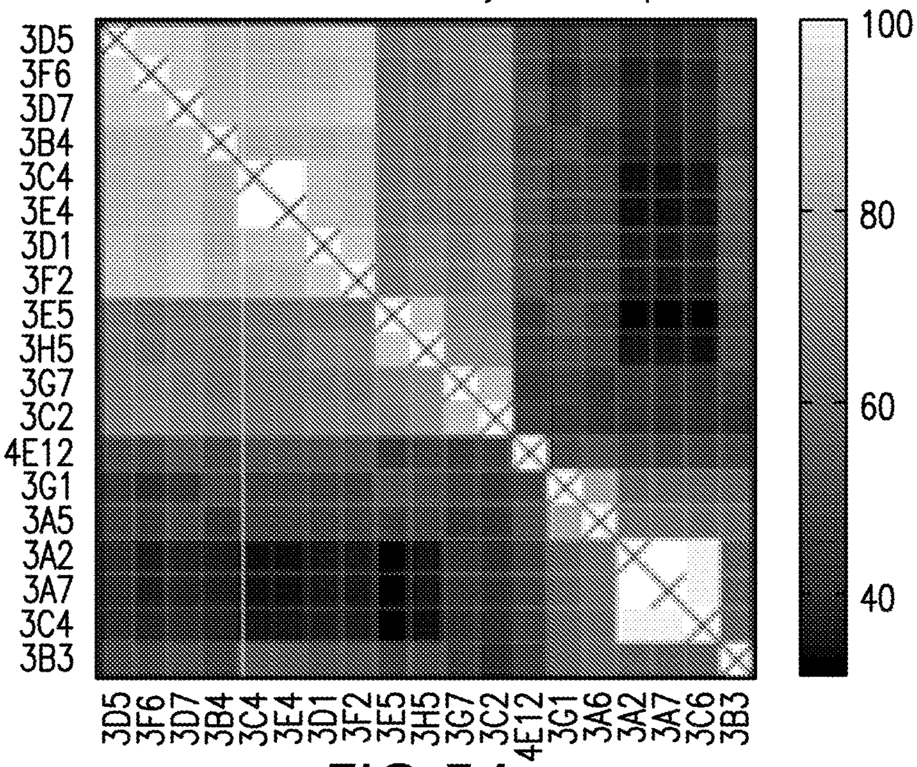
FIG. 5A-5B are heat maps showing amino acid sequence similarities of selected clones.
Figure 5B:
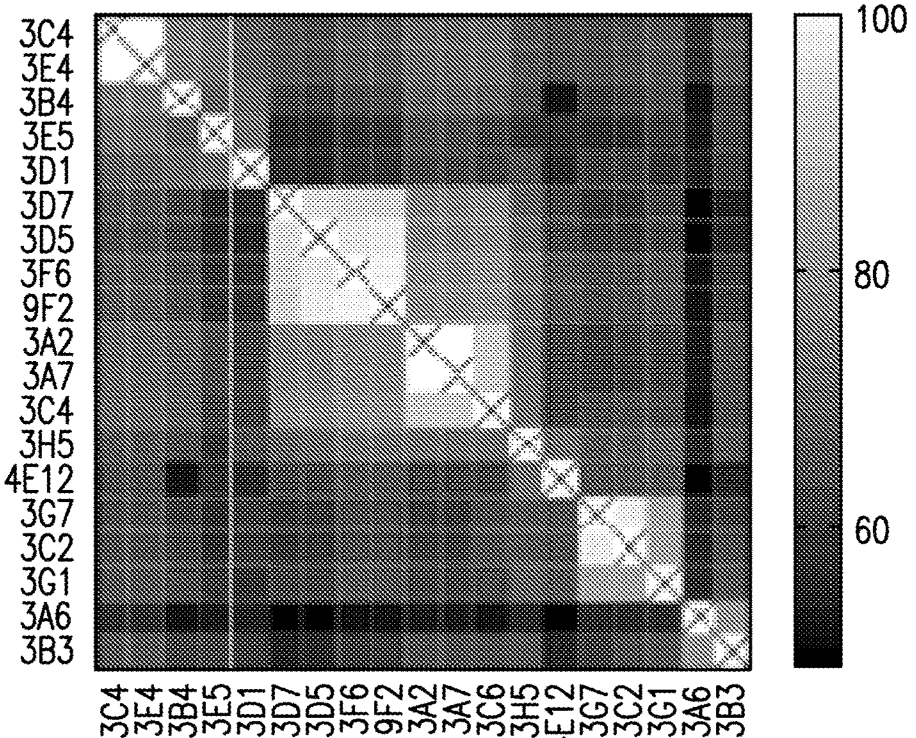

RNA isolated from hybridomas producing most of the selected antibodies were subjected to reverse transcription and high-throughput DNA sequencing, with results shown in FIG. 5, grouped by sequence similarity of heavy and light chain variable regions. Two pairs of antibodies (3A2 and 3A7, 3C4 and 3E4) have identical sequences, consistent with their very similar measured functions. Most striking is the clustering of group 1 antibodies (3A2/3A7, 3C6) and the other potent neutralizers and ACE2 binding inhibitors (3B3, 3A6, 3G1, 3C2, which were not subjected to the cross-reactive binning shown in FIG. 4), and the separate clustering of ACE2 binding enhancers.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize or be able to ascertain using no more than routine experimentation, many equivalents to the specific embodiments of the invention described herein. Such equivalents are intended to be encompassed by the following claims.

We claim:

1. An antibody or antigen-binding fragment thereof comprising a heavy chain variable region comprising SEQ ID NO:19, and a light chain variable region comprising SEQ ID NO:20.

2. The antibody or antigen-binding fragment thereof of claim 1, wherein the antibody or antigen-binding fragment thereof is a monoclonal antibody or antigen-binding fragment thereof or a humanized antibody or an antigen-binding fragment thereof.

3. The antibody or antigen-binding fragment thereof of claim 1, wherein the antibody or antigen-binding fragment thereof is conjugated to a solid support or resin.

4. A pharmaceutical composition comprising:

the antibody or antigen-binding fragment thereof of claim 1 in an amount effective to inhibit or reduce SARS-COV-2 spike protein binding to angiotensin converting enzyme 2 (ACE2) receptors under physiological conditions.

5. The pharmaceutical composition of claim 4, further comprising an excipient.

6. An immunoassay comprising the antibody or antigen-binding fragments thereof of claim 1.

7. The antibody or antigen-binding fragment thereof of claim 1, wherein the antibody or antigen-binding fragment thereof is labeled with a detectable label.

8. The antibody or antigen-binding fragment thereof of claim 7, wherein the detectable label is a fluorophore.

9. The antibody of claim 1, wherein the antibody or antigen binding fragment thereof specifically binds to a SARS-COV-2 spike protein or fragment thereof.

10. A method for treating coronavirus infection in a subject in need thereof comprising:

administering the antibody or antigen-binding fragment thereof of claim 1 to the subject in an amount effective to treat the coronavirus infection.

11. The method of claim 10, wherein the coronavirus is SARS-COV-2.

12. A method for detecting SARS-COV-2 in a sample, comprising:

contacting the sample with an antibody or antigen-binding fragment thereof according to claim 1; and detecting antibody or antigen-binding fragments thereof bound to SARS-CoV-2 in the sample, wherein the presence of bound antibody or antigen-binding fragments thereof in the sample indicates the sample contains SARS-COV-2.

13. A method for diagnosing a subject with a SARS-COV-2 infection, comprising:

performing the method of claim 12 on a sample obtained from the subject, wherein the detection of bound antibody or antigen-binding fragments thereof in the sample indicates the subject has a SARS-COV-2 infection.

14. The method of claim 13, wherein the method further includes the step of diagnosing the subject with a SARS-COV-2 infection if bound antibody or antigen-binding fragments thereof are detected in the sample.

15. A kit comprising:

a container containing the antibody or antigen-binding fragment thereof of claim 1, and optionally, instructions for administering the antibody or antigen-binding fragment thereof.

16. A method for treating coronavirus in a subject in need thereof comprising administering an effective amount of the antibody or antigen binding fragment according to claim 1.

17. The method of claim 16, wherein the antibody is a monoclonal antibody.

18. The method of claim 16, wherein the antibody is a recombinant antibody.

19. The antibody or antigen-binding fragment thereof of claim 7, wherein the antibody or antigen-binding fragment thereof labeled with a detectable label binds the spike protein of SARS-COV-2 and is useful for the diagnostic detection of a SARS-COV-2 infection.

20. The pharmaceutical composition of claim 4, wherein the composition is administered to a subject in need thereof in an amount effective to treat or prevent a coronavirus infection by inhibiting or reducing SARS-COV-2 spike protein binding to ACE2 receptors.

* * * * *